(12) United States Patent
Sellar et al.

(10) Patent No.: US 7,771,930 B2
(45) Date of Patent: Aug. 10, 2010

(54) CANCER

(75) Inventors: Grant Clark Sellar, Edinburgh (GB); Hani Gabra, Edinburgh (GB)

(73) Assignee: Cancer Research Technology Limited, London (GB)

( * ) Notice: Subject to any disclaimer, the term of this patent is extended or adjusted under 35 U.S.C. 154(b) by 940 days.

(21) Appl. No.: 10/482,199

(22) PCT Filed: Jun. 20, 2002

(86) PCT No.: PCT/GB02/02928

§ 371 (c)(1),
(2), (4) Date: Jun. 21, 2004

(87) PCT Pub. No.: WO03/002765

PCT Pub. Date: Jan. 9, 2003

(65) Prior Publication Data

US 2004/0241682 A1 Dec. 2, 2004

Related U.S. Application Data

(60) Provisional application No. 60/330,792, filed on Oct. 31, 2001, provisional application No. 60/305,137, filed on Jul. 16, 2001.

(30) Foreign Application Priority Data

Jun. 27, 2001 (GB) .................................. 0115673.6

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS 5,861,283 A    1/1999   Levitt et al.

FOREIGN PATENT DOCUMENTS

| EP | 0 727 486 | 8/1996 |
| EP | 1 077 259 | 2/2001 |
| WO | WO 96/30052 | 10/1996 |
| WO | WO 99/14327 | 3/1999 |
| WO | WO 99/14328 | 3/1999 |
| WO | WO 99/46281 | 9/1999 |
| WO | WO 00/61754 | 10/2000 |
| WO | WO 00/73479 | 12/2000 |
| WO | WO 00/77252 | 12/2000 |
| WO | WO 01/19845 | 3/2001 |

OTHER PUBLICATIONS

Teodoridis et al., Cancer Res, 2005, 65:19:pp. 8961-8967.*
Kroese et al. Genetics in Medicine, vol. 6 (2004), p. 475-480.*
Ionnidis (Plost Med, 2005, 2(8):e124).*
Hattersley et al. (Lancet, 2005, vol. 366, pp. 1315-1323).*
Hegele et al. Arterioscler. Thromb. Vasc. Biol. 2002: 22:1058-1061.*
Clarke and Moss (1997) Eur J Neurosci 9:334-341.
Compton (1991) Nature 350:91-92.
Fathalla (1971) Lancet 2:163.
Furuta et al (2001) Am J Pathol 159(2):449-455.
Gabra et al (1995) Br J Cancer 72:367-375.
Gabra et al (1996) Cancer Res 56:950-954.
Gabra et al (1996) Int J Oncol 8:625-631.
Gabra et al (1998) Proc Amer Assoc Can Res 29:622-623 Abstract #4236.
GenBank Accession No. AC012234.6 (2000).
GenBank Accession No. AC027631.4 (2000).
GenBank Accession No. AP000843.3 (2000).
GenBank Accession No. NM_002545.2 (2003).
GenBank Accession No. NM_016522 (2003).
GenBank Accession No. NP_002536 (2003).
Gil et al (1998) J Neuroscience 18(22):9312-9325.
Govitrapong et al (1993) J Biol Chem 268(24):18280-18285.
Hachisuka et al (1996) Neurochem Int 28(4):373-379.
Hancox et al (1997) Mol Brain Res 44:273-285.
Herman et al (1996) Proc Natl Acad Sci USA 93:9821-9826.
Kannan et al (1995) EurJ Haematol 55:145-151.
Kim et al (1999) Mol Cells 90(3):270-276.
Knudson Jr (1971) Proc Natl Acad Sci USA 68(4):820-823.
Lane et al (1995) Brain Research 698:15-22.
Lodge et al (2001) Mol Cell Neurosci 17:746-760.
Loh and Smith (1990) Annu Rev Pharmacol Toxicol 30:123-147.
Loh and Smith (1996) NIDA Res Monogr 161:141-152.
Maekawa et al (1999) Biochem Biophys Res Commun 262:671-676.
Maekawa et al (2001) Clin Chem Lab Med 39(2):121-128.
Miyata et al (2000) J Comp Neurol 424:74-85.
Nakajima et al (1997) Neuroreport 8(14):3005-3008.
Pimenta et al (1996) Gene 170:189-195.
Rimessi et al (1994) Oncogene 9:3467-3474.
Satoh et al (1993) Mol Carcinogenesis 7:157-164.
Schofield et al (1989) EMBO J 8(2):489-495.
Sellar et al (1998) Br J Cancer 78:Poster P185.
Sellar et al (2002) Br J Cancer 86(S1):S24 Abstract # 5.5.
Sellar et al (2002) Proc Am Assoc Cancer Res 43:146 Abstract # 726.
Shark and Lee (1995) Gene 155:213-217.
Struyk et al (1995) J Neurosci 15(3):2141-2156.
Tanaka et al (1991) Nature 349:340-342.
Wick et al (1996) Mol Brain Res 36:322-328.
Wilson et al (1996) J Cell Sci 109:3129-3138.
Wu et al (1990) J Protein Chem 9(1):3-7 .
Yoshida et al (1994) Mol Carcinogenesis 9:114-121.
Private-Public Partnership Research Papers 1996 Field Five Explanation of Biological Defence Mechanism as the Basis of Health Retention, pp. 282-288 (1998).
Chen et al., Loss of OPCML expression and the correlation with CpG island methylation and LOH in ovarian serous carcinoma. Eur J Gynaecol Oncol. 2007;28(6):464-7. Abstract Only.

(Continued)

Primary Examiner—Sarae Bausch

(57) ABSTRACT

The invention provides methods of diagnosis, prognosis and treatment of cancer related to the OBCAM and NTM genes. The methods are particularly suited to ovarian and colorectal cancers.

2 Claims, 30 Drawing Sheets

OTHER PUBLICATIONS

Figure 1:
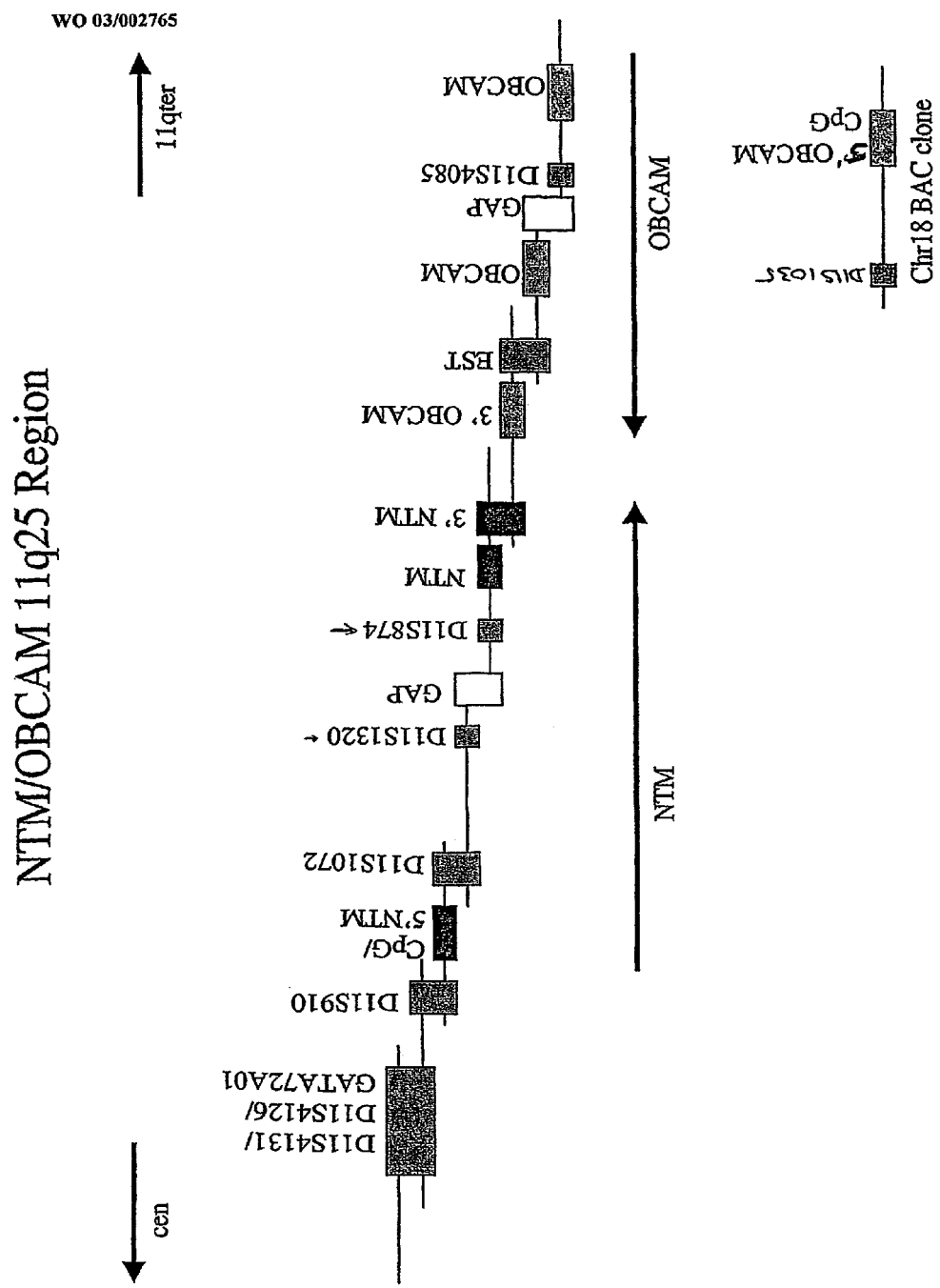

Czekierdowski et al., Opioid-binding protein/cell adhesion molecule-like (OPCML) gene and promoter methylation status in women with ovarian cancer. Neuro Endocrinol Lett. Oct. 2006;27(5):609-13. Abstract Only.

Hachisuka et al., Localization of opioid-binding cell adhesion molecule (OBCAM) in adult rat brain. Brain Res. Sep. 25, 1999;842(2):482-6.

Lippman et al., Opioid-binding cell adhesion molecule (OBCAM)-related clones from a rat brain cDNA library. Gene. Aug. 15, 1992;117(2):249-54.

Liu et al., [Correlations of CpG island methylator phenotype and OPCML gene methylation to carcinogenesis of hepatocellular carcinoma] Ai Zheng. Jun. 2006;25(6):696-700. Abstract Only.

Mei et al., RAS-mediated epigenetic inactivation of OPCML in oncogenic transformation of human ovarian surface epithelial cells. FASEB J. Mar. 2006;20(3):497-9. Epub Dec. 29, 2005.

Ntougkos et al., The IgLON family in epithelial ovarian cancer: expression profiles and clinicopathologic correlates. Clin Cancer Res. Aug. 15, 2005;11(16):5764-8.

Reed et al., Expression of cellular adhesion molecule 'OPCML' is down-regulated in gliomas and other brain tumours. Neuropathol Appl Neurobiol. Feb. 2007;33(1):77-85.

Sellar et al., OPCML at 11 q25 is epigenetically inactivated and has tumor-suppressor function in epithelial ovarian cancer. Nat Genet. Jul. 2003;34(3):337-43.

Tsou et al., Identification of a panel of sensitive and specific DNA methylation markers for lung adenocarcinoma. Mol Cancer. Oct. 29, 2007;6:70.

Wang et al., Comparison of gene expression profiles between primary tumor and metastatic lesions in gastric cancer patients using laser microdissection and cDNA microarray. World J Gastroenterol. Nov. 21, 2006;12(43):6949-54.

Zhang et al., [Deletion of OPCML gene and promoter methylation in ovarian epithelial carcinoma] Zhongguo Yi Xue Ke Xue Yuan Xue Bao. Apr. 2006;28(2):173-7. Abstract Only.

* cited by examiner

FIGURE 3

Ovarian LOH Rates:

|  | No. analysed | No. informative | No. LOH | %LOH |
|---|---|---|---|---|
| D11S1894 | 58 | 44 | 11 | 25 |
| D11S4150 | 54 | 50 | 18 | 36 |
| D11S912 | 60 | 53 | 18 | 34 |
| GATA69G01 | 64 | 24 | 8 | 33 |
| D11S1884 | 54 | 26 | 9 | 35 |
| D11S4126 | 63 | 30 | 11 | 37 |
| GATA72A01 | 62 | 24 | 6 | 25 |
| D11S4131 | 65 | 52 | 17 | 33 |
| D11S910 | 59 | 38 | 10 | 26 |
| D11S1320 | 60 | 39 | 11 | 28 |
| D11S874 | 65 | 38 | 11 | 29 |
| D11S4085 | 62 | 43 | 24 | 56 |

Colorectal LOH Rates:

|  | No. analysed | No. informative | No. LOH | %LOH |
|---|---|---|---|---|
| D11S1894 | 39 | 12 | 7 | 58 |
| D11S4150 | 38 | 25 | 9 | 36 |
| D11S912 | 39 | 26 | 11 | 42 |
| GATA69G01 | 38 | 9 | 3 | 33 |
| D11S1884 | 38 | 9 | 5 | 56 |
| D11S4126 | 39 | 28 | 7 | 25 |
| GATA72A01 | 39 | 16 | 7 | 44 |
| D11S4131 | 39 | 28 | 13 | 46 |
| D11S910 | 39 | 19 | 5 | 26 |
| D11S1320 | 39 | 20 | 10 | 50 |
| D11S874 | 39 | 19 | 10 | 51 |
| D11S4085 | 39 | 25 | 8 | 32 |

RESULTS

MOLECULAR ANALYSIS

66% (43/65) of the ovarian tumours and 69% (27/39) of the colorectal tumours had LOH involving at least 1 locus within the 11q24 region. 8 tumours in each group had LOH at all informative loci.

The figure below shows how the markers have been reordered and documents the number of cases with LOH as a percentage of the number of informative cases for each marker.

FIGURE 6

| Case | Neurotrimin | OBCAM | Overall |
|---|---|---|---|
| 295 | M | M | C |
| 303 | M | U | D |
| 300 | M | M | C |
| 290 | U | U | C |
| 269 | M | M | C |
| 296 | U | U | C |
| 393 |  | M |  |
| 311 |  | M |  |
| 386 | M | M | C |
| 304 | M | M | C |
| 307 | M | M | C |
| 308 | U | M | D |
| 389 | M | M | C |
| OVERALL | 8/11=73% | 11/13=85% | 9/11=82% |

OVERALL METHYLATION RATE = 11/13 = 85%

M = Methylated
U = Unmethylated

FIGURE 7 (page 1 of 3)

```
                                                                      Nucleotide
   PubMed    Nucleotide    Protein    Genome    Structure    PopSet    Taxonomy    OMIM 1: NM_002545  Homo sapiens         PubMed, Protein, Related Sequences, Taxonomy, OMIM, LinkOut
                opioid-binding
                protein/cell
                adhesion
                molecule-like
                (OPCML), mRNA LOCUS         NM_002545     3110 bp    mRNA             PRI       02-APR-2001
DEFINITION    Homo sapiens opioid-binding protein/cell adhesion molecule-like
              (OPCML), mRNA.
ACCESSION     NM_002545
VERSION       NM_002545.2  GI:13518022
KEYWORDS
SOURCE        human.
  ORGANISM    Homo sapiens
              Eukaryota; Metazoa; Chordata; Craniata; Vertebrata; Euteleostomi;
              Mammalia; Eutheria; Primates; Catarrhini; Hominidae; Homo.
REFERENCE     1  (bases 1 to 3110)
  AUTHORS     Smith,M.W., Clark,S.P., Hutchinson,J.S., Wei,Y.H., Churukian,A.C.,
              Daniels,L.B., Diggle,K.L., Gen,M.W., Romo,A.J., Lin,Y. et al.
  TITLE       A sequence-tagged site map of human chromosome 11
  JOURNAL     Genomics 17 (3), 699-725 (1993)
  MEDLINE     94063915
   PUBMED     8244387
REFERENCE     2  (bases 1 to 3110)
  AUTHORS     Struyk,A.F., Canoll,P.D., Wolfgang,M.J., Rosen,C.L., D'Eustachio,P.
              and Salzer,J.L.
  TITLE       Cloning of neurotrimin defines a new subfamily of differentially
              expressed neural cell adhesion molecules
  JOURNAL     J Neurosci 15 (3), 2141-2156 (1995)
  MEDLINE     95198094
   PUBMED     7891157
REFERENCE     3  (bases 1 to 3110)
  AUTHORS     Shark,K.B. and Lee,N.M.
  TITLE       Cloning, sequencing and localization to chromosome 11 of a cDNA
              encoding a human opioid-binding cell adhesion molecule (OBCAM)
  JOURNAL     Gene 155 (2), 213-217 (1995)
  MEDLINE     95237612
   PUBMED     7721093
  COMMENT     REVIEWED REFSEQ: This record has been curated by NCBI staff. The
              reference sequence was derived from L34774.1, U79251.1.
              On Apr 3, 2001 this sequence version replaced gi:4505504.
              Summary: This gene encodes a member of the IgLON subfamily in the
              immunoglobulin protein superfamily. The encoded protein is
              localized in the plasma membrane and may have an accessory role in
              opioid receptor function. This gene has an ortholog in rat and
              bovine. The opioid binding-cell adhesion molecule encoded by the
              rat gene binds opioid alkaloids in the presence of acidic lipids,
              exhibits selectivity for mu ligands and acts as a GPI-anchored
              protein. Since the encoded protein is highly conserved in species
              during evolution, it may have a fundamental role in mammalian
              systems.
              COMPLETENESS: complete on the 3' end.
FEATURES             Location/Qualifiers
     source          1..3110
                     /organism="Homo sapiens"
                     /db_xref="taxon:9606"
```

FIGURE 7 (page 2 of 3)

```
                    /chromosome="11"
                    /map="11"
     gene           1..3110
                    /gene="OPCML"
                    /note="OBCAM; OPCM"
                    /db_xref="LocusID:4978"
                    /db_xref="MIM:600632"
     CDS            51..1088
                    /gene="OPCML"
                    /note="opiate binding-cell adhesion molecule"
                    /codon_start=1
                    /db_xref="LocusID:4978"
                    /db_xref="MIM:600632"
                    /product="opioid-binding cell adhesion molecule precursor"
                    /protein_id="NP_002536.1"
                    /db_xref="GI:4505505"
                    /translation="MGVCGYLFLPWKCLVVVSLRLLFLVPTGVPVRSGDATFPKAMDN
                    VTVRQGESATLRCTIDDRVTRVAWLNRSTILYAGNDKWSIDPRVIILVNTPTQYSIMI
                    QNVDVYDEGPYTCSVQTDNHPKTSRVHLIVQVPPQIMNISSDITVNEGSSVTLLCLAI
                    GRPEPTVTWRHLSVKEGQGFVSEDEYLEISDIKRDQSGEYECSALNDVAAPDVRKVKI
                    TVNYPPYISKAKNTGVSVGQKGILSCEASAVPMAEFQWFKEETRLATGLDGMRIENKG
                    RMSTLTFFNVSEKDYGNYTCVATNKLGNTNASITLYGPGAVIDGVNSASRALACLWLS
                    GTLLAHFFIKF"
     sig_peptide    51..131
     mat_peptide    132..1016
                    /product="opioid-binding cell adhesion molecule"
     misc_feature   180..449
                    /note="IG_like; Region: Immunoglobulin like"
     misc_feature   474..671
                    /note="IG_like; Region: Immunoglobulin like"
     misc_feature   495..668
                    /note="IG; Region: Immunoglobulin"
     misc_feature   750..986
                    /note="IG_like; Region: Immunoglobulin like"
     misc_feature   759..944
                    /note="ig; Region: Immunoglobulin domain"
     misc_feature   759..959
                    /note="IG; Region: Immunoglobulin"
     polyA_signal   3074..3079
     polyA_site     3092
BASE COUNT      844 a    751 c    661 g    854 t
ORIGIN
        1 gaccaggact gtgcggctgc cggagtcctg ggaagttgtg gctgtcgaga atgggggtct
       61 gtgggtacct gttcctgccc tggaagtgcc tgtggtcgt gtctctcagg ctgctgttcc
      121 ttgtacccac aggagtgccc gtgcgcagcg gagatgcgca cttcccaaa gctatggaca
      181 acgtgacggt ccggcagggg gagagcgcca ccctcaggtg taccatagat gaccggtaa
      241 cccgggtggc ctggctaaac cgcagcacca tcctctacgc tgggaatgac aagtggtcca
      301 tagaccctcg tgtgatcatc ctggtcaata caccaaccca gtacagcatc atgatccaaa
      361 atgtggatgt gtatgacgaa ggtccgtaca cctgctctgt gcagacagac aatcatccca
      421 aaacgtcccg ggttcaccta atagtgcaag ttcctcctca gatcatgaat atctcctcag
      481 acatcactgt gaatgaggga agcagtgtga ccctgctgtg tcttgctatt ggcagaccag
      541 agccaactgt gacatggaga cacctgtcag tcaaggaagg ccagggcttt gtaagtgagg
      601 atgagtacct ggagatctct gacatcaagc gagaccagtc cggggagtac gaatgcagcg
      661 cgttgaacga tgtcgctgcg cccgatgtgc ggaaagtaaa aatcactgta aactatcctc
      721 cctatatctc aaaagccaag aacactggtg tttcagtcgg tcagaagggc atcctgagct
      781 gtgaagcctc tgcagtcccc atggctgaat tccagtggtt caaggaagaa accaggttag
      841 ccactggtct ggatggaatg aggattgaaa acaaaggccg catgtccact ctgactttct
      901 tcaatgtttc tgaaaaggat tatgggaact atacttgtgt ggccacgaac aagcttggga
      961 acaccaatgc cagcatcaca ttgtatgggc ctggagcagt cattgatggt gtaaactcgg
     1021 cctccagagc actggcttgt ctctggctat cagggaccct cttagccac ttcttcatca
     1081 agtttgata agaaatccta ggtcctctga gcaacgcctg cttctcatat cacagacttt
     1141 aatctacact gcggagagca aaccagcttg ggcttctttt tgttttttc tgttattcta
     1201 gatttgtttt cttttgttt ttgtttattt gtttgtttgc ttttatttcc agcttgaatg
     1261 agtgggggttg gggcggggt gggcagggtt ctaccacgtg taggataatc attcattggt
     1321 gtgtccaaaa atggggtctg ctcctgctac cttgaccctt ccctttcctc tgcttctctc
     1381 ctcatcatca ttcccaacaa catcctctgc cacacaacaa aaaacgtaag tttcatttgg
     1441 gcaaaaattg agcctcacaa taaacaccct gaagacacaa cttgacttat aacatagtgc
     1501 acagcaagag ctacatccaa gtgtcctatt atctgtgatt attttcttaa tgacaatgta
     1561 catatgcccc catccatgtt aattattatc taattccatt agggttcacg tctttctttt
     1621 ctgggacact atcctactat atccatatct atagatttca atatagatga ttgtgccatc
```

FIGURE 7 (page 3 of 3)

```
1681 ttctgtagcc cctccgctct actcattcct tccaccatct gcagagattt gaagttggg
1741 gctatgcatg aaacccaaca ctaaattttg caagtcaagt gaccaaaaaa gggggaggca
1801 ttttgaagat agaacctcta ttttaaaaag agaagttcaa ctcataaacg tgattgatag
1861 gtggctgatt tatttaggtt ttgtcaagct atctatcaaa gtaatggtac agttacccat
1921 ctactcaaat atctgattta tctcaccatc caattatcta cccacctgtc ttcctctcta
1981 gcaatctatt tactgtttat caatctatca atgtaattgt ctaacactcc tttctattct
2041 ctccctacta ctcactatca attcatcccc atatgaatct ctaaccatat tgtatctctc
2101 ccactgtatt catttataca ccatcagcag acattggcat cttcaaaatt atctttcaac
2161 ttctgtgaaa gccaacgatc tcacaggtta acaaaataca aagcaatac cctgtgttgt
2221 ggactcttta aaatctggta tcctatccac ccaagggaga cactaacaga taggccaaag
2281 tagcaagcta atgatcagtc actcactatt cccggaagag cctgtgtttt ctaaaacact
2341 ttcttgggaa gcagatcagc ctagaaaagt tttgattagc actgtggttt tccttttgca
2401 cttgaaggac aaaggtgcca gctttatgc ttctctcaac ccttcaagaa agtacatgtc
2461 aggaacctat ggctggcttt cctagcagc aagaacttga gagaaaaaca catctgtctc
2521 tgcaatgcaa agtgaagagt ccaccgct gagtgggatg acttcagcta gagtctcctt
2581 tctgctccag ttctggttta atctgtttga aaactatcca gtaaaaagct gatggaggcc
2641 aattacatgg cgggtgtatt gacaactctg gtatttgttt caggaagctc ttctaagctg
2701 agggcacttg agcaactgac ttaattttca agcacttgat taacacaaca ctgcaaacag
2761 aagggagaaa gtgtcagtga cacagtttcc tctgatgcag ctgcttctcc aatggctttg
2821 gggaagaact tcaccagctc ttcaggttca aagcagaccc agcatacaaa caagagctga
2881 gccacctttg ctgtcttgtc tcctgggacg agaaggactc atccagcaaa gttgcctggg
2941 attcaaaata aaggcattgc agaccgcaca ggtgtgctgc agggactgat ccacagagag
3001 gatgagaatg cagcatcaat cgcagacctg ccctgcctca gttggaaaac cttttcaggc
3061 cctcagtcta aaaataaaa aatatgagca ccaaaaaaaa aaaaaaaaa
```

Restrictions on Use | Write to the HelpDesk
NCBI | NLM | NIH

FIGURE 8 (page 1 of 2)

1: NM_016522 Homo sapiens neurotrimin PubMed, Protein, Related Sequences, Taxonomy, LinkOut (HNT), mRNA

```
LOCUS       NM_016522    1839 bp    mRNA           PRI      02-NOV-2000
DEFINITION  Homo sapiens neurotrimin (HNT), mRNA.
ACCESSION   NM_016522
VERSION     NM_016522.1  GI:7705412
KEYWORDS    .
SOURCE      human.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 1839)
  AUTHORS   Struyk AF, Canoll PD, Wolfgang MJ, Rosen CL, D'Eustachio P and
            Salzer JL.
  TITLE     Cloning of neurotrimin defines a new subfamily of differentially
            expressed neural cell adhesion molecules
  JOURNAL   J. Neurosci. 15 (3 Pt 2), 2141-2156 (1995)
  MEDLINE   95198094
   PUBMED   7891157
REFERENCE   2  (bases 1 to 1839)
  AUTHORS   Li,G., Jin,J., Tan,X., Hu,S., Yuan,J. and Qiang,B.
  TITLE     Cloning and identification of human neurotrimin full length cDNA
  JOURNAL   Unpublished
COMMENT     PROVISIONAL REFSEQ: This record has not yet been subject to final
            NCBI review. The reference sequence was derived from AF126426.1.
FEATURES             Location/Qualifiers
     source          1..1839
                     /organism="Homo sapiens"
                     /db_xref="taxon:9606"
                     /chromosome="11"
                     /map="11q25"
     gene            1..1839
                     /gene="HNT"
                     /db_xref="LocusID:50863"
     CDS             265..1299
                     /gene="HNT"
                     /codon_start=1
                     /db_xref="LocusID:50863"
                     /product="neurotrimin"
                     /protein_id="NP_057606.1"
                     /db_xref="GI:7705413"
                     /translation="MGVCGYLFLPWKCLVVVSLRLLFLVPTGVPVRSGDATFPKAMDN
                     VTVRQGESATLRCTIDNRVTRVAWLNRSTILYAGNDKWCLDPRVVLLSNTQTQYSIEI
                     QNVDVYDEGPYTCSVQTDNHPKTSRVHLIVQVSPKIVEISSDISINEGNNISLTCIAT
                     GRPEPTVTWRHISPKAVGFVSEDEYLEIQGITREQSGDYECSASNDVAAPVVRRVKVT
                     VNYPPYISEAKGTGVPVGQKGTLQCEASAVPSAEFQWYKDDKRLIEGKKGVKVENRPF
                     LSKLIFFNVSEHDYGNYTCVASNKLGHTNASIMLFGPGAVSEVSNGTSRRAGCVWLLP
                     LLVLHLLLKF"
     misc_feature    409..630
                     /note="IG; Region: Immunoglobulin"
     misc_feature    709..879
                     /note="IG; Region: Immunoglobulin"
     misc_feature    970..1170
                     /note="IG; Region: Immunoglobulin"
BASE COUNT      464 a    506 c    503 g    366 t
ORIGIN
        1 gcggaagcag cgaggaggga gcccccttg gccgtcctcc gtggaaccgg ttttccgagg
       61 ctgcaaaag ccgaggctgg atttggggga ggaatattag actcggagga gtctgcgcgc
```

FIGURE 8 (page 2 of 2)

```
 121 ttttctcctc ccgcgcctc ccggtcgccg cgggttcacc gctcagccc cgcgctcgct
 181 ccgcacccca cccacttcct gtgctcgccc gggggcgtg tgccgtgcgg ctgccggagt
 241 tcggggaagt tgtggctgtc gagaatgggg gtctgtgggt acctgttcct gccctggaag
 301 tgcctcgtgg tcgtgtctct caggctgctg ttccttgtac ccacaggagt gcccgtgcgc
 361 agcggagatg ccaccttccc caaagctatg gacaacgtga cggtccggca ggggagagc
 421 gccaccctca ggtgcactat tgacaaccgg gtcacccggg tggcctggct aaaccgcagc
 481 accatcctct atgctgggaa tgacaagtgg tgcctggatc ctcgcgtggt ccttctgagc
 541 aacacccaaa cgcagtacag catcgagatc cagaacgtgg atgtgtatga cgagggccct
 601 tacacctgct cggtgcagac agacaaccac ccaaagacct ctagggtcca cctcattgtg
 661 caagtatctc ccaaaattgt agagatttct tcagatatct ccattaatga agggaacaat
 721 attagcctca cctgcatagc aactggtaga ccagccta cggttacttg gagacacatc
 781 tctcccaaag cggttggctt tgtgagtgaa gacgaatact tggaaattca gggcatcacc
 841 cgggaacagt cagggacta cgagtgcagt gcctccaatg acgtggccgc gcccgtggta
 901 cggagagtaa aggtcaccgt gaactatcca ccatacattt cagaagccaa gggtacaggt
 961 gtccccgtgg gacaaaaggg gacactgcag tgtgaagcct cagcagtccc ctcagcagaa
1021 ttccagtggt acaaggatga caaaagactg attgaaggaa agaaaggggt gaaagtggaa
1081 aacagacctt tcctctcaaa actcatcttc ttcaatgtct ctgaacatga ctatgggaac
1141 tacacttgcg tggcctccaa caagctgggc cacaccaatg ccagcatcat gctatttgt
1201 ccaggcgccg tcagcgaggt gagcaacggc acgtcgagga gggcaggctg cgtctggctg
1261 ctgcctcttc tggtcttgca cctgcttctc aaattttgat gtgagtgcca cttccccacc
1321 cgggaaaggc tgccgccacc accaccacca acacaacagc aatggcaaca ccgacagcaa
1381 ccaatcagat atatacaaat gaaattagaa gaaacacagc ctcatgggac agaaatttga
1441 gggagggaa caaagaatac tttgggggga aaagagtttt aaaaaagaaa ttgaaaattg
1501 ccttgcagat atttaggtac aatggagttt tcttttccca aacgggaaga acacagcaca
1561 cccggcttgg acccactgca agctgcatcg tgcaacctct ttggtgccag tgtgggcaag
1621 ggctcagcct ctctgcccac agactgcccc cacgtggaac attctggagc tggccatccc
1681 aaattcaatc agtccataga gacgaacaga atgagacctt ccggcccaag cgtggcgctt
1741 ccggcccaag cgtggcgctg cgggcacttt ggtagactgt gccaccacgg cgtgtgttgt
1801 gaaacgtgaa ataaaagag caaaaaaaaa aaaaaaaa
```

FIGURE 9 (page 1 of 3)

Translated NTM Isoforms

+33bp isoform

```
atgggggtctgtgggtacctgttcctgccctggaagtgcctcgtggtcgtgtctctcagg
 M  G  V  C  G  Y  L  F  L  P  W  K  C  L  V  V  V  S  L  R
ctgctgttccttgtacccacaggagtgcccgtgcgcagcggagatgccaccttccccaaa
 L  L  F  L  V  P  T  G  V  P  V  R  S  G  D  A  T  F  P  K
gctatggacaacgtgacggtccggcaggggggagagcgccaccctcaggtgcactattgac
 A  M  D  N  V  T  V  R  Q  G  E  S  A  T  L  R  C  T  I  D
aaccgggtcacccgggtggcctggctaaaccgcagcaccatcctctatgctgggaatgac
 N  R  V  T  R  V  A  W  L  N  R  S  T  I  L  Y  A  G  N  D
aagtggtgcctggatcctcgcgtggtccttctgagcaacacccaaacgcagtacagcatc
 K  W  C  L  D  P  R  V  V  L  L  S  N  T  Q  T  Q  Y  S  I
gagatccagaacgtggatgtgtatgacgagggcccttacacctgctcggtgcagacagac
 E  I  Q  N  V  D  V  Y  D  E  G  P  Y  T  C  S  V  Q  T  D
aaccacccaaagacctctagggtccacctcattgtgcaagtatctcccaaaattgtagag
 N  H  P  K  T  S  R  V  H  L  I  V  Q  V  S  P  K  I  V  E
atttcttcagatatctccattaatgaagggaacaatattagcctcacctgcatagcaact
 I  S  S  D  I  S  I  N  E  G  N  N  I  S  L  T  C  I  A  T
ggtagaccagagcctacggttacttggagacacatctctcccaaagcggttggctttgtg
 G  R  P  E  P  T  V  T  W  R  H  I  S  P  K  A  V  G  F  V
agtgaagacgaatacttggaaattcagggcatcacccgggaacagtcagggactacgag
 S  E  D  E  Y  L  E  I  Q  G  I  T  R  E  Q  S  G  D  Y  E
tgcagtgcctccaatgacgtggccgcgcccgtggtacggagagtaaaggtcaccgtgaac
 C  S  A  S  N  D  V  A  A  P  V  V  R  R  V  K  V  T  V  N
tatccaccatacatttcagaagccaagggtacaggtgtcccgtgggacaaaaggggaca
 Y  P  P  Y  I  S  E  A  K  G  T  G  V  P  V  G  Q  K  G  T
ctgcagtgtgaagcctcagcagtccccctcagcagaattccagtggtacaaggatgacaaa
 L  Q  C  E  A  S  A  V  P  S  A  E  F  Q  W  Y  K  D  D  K
agactgattgaaggaaagaaaggggtgaaagtggaaaacagacctttcctctcaaaactc
 R  L  I  E  G  K  K  G  V  K  V  E  N  R  P  F  L  S  K  L
atcttcttcaatgtctctgaacatgactatgggaactacacttgcgtggcctccaacaag
 I  F  F  N  V  S  E  H  D  Y  G  N  Y  T  C  V  A  S  N  K
ctgggccacaccaatgccagcatcatgctatttgaagtgaaaactacagccctgaccct
 L  G  H  T  N  A  S  I  M  L  F  E  V  K  T  T  A  L  T  P
tggaaaggtccaggcgccgtcagcgaggtgagcaacggcacgtcgaggagggcaggctgc
 W  K  G  P  G  A  V  S  E  V  S  N  G  T  S  R  R  A  G  C
gtctggctgctgcctcttctggtcttgcacctgcttctcaaattttga
 V  W  L  L  P  L  L  V  L  H  L  L  L  K  F  *
```

FIGURE 9 (page 2 of 3)

+69bp isoform

```
atgggggtctgtgggtacctgttcctgccctggaagtgcctcgtggtcgtgtctctcagg
 M  G  V  C  G  Y  L  F  L  P  W  K  C  L  V  V  V  S  L  R
ctgctgttccttgtacccacaggagtgcccgtgcgcagcggagatgccaccttccccaaa
 L  L  F  L  V  P  T  G  V  P  V  R  S  G  D  A  T  F  P  K
gctatggacaacgtgacggtccggcaggggagagcgccaccctcaggtgcactattgac
 A  M  D  N  V  T  V  R  Q  G  E  S  A  T  L  R  C  T  I  D
aaccgggtcacccgggtggcctggctaaaccgcagcaccatcctctatgctgggaatgac
 N  R  V  T  R  V  A  W  L  N  R  S  T  I  L  Y  A  G  N  D
aagtggtgcctggatcctcgcgtggtccttctgagcaacacccaaacgcagtacagcatc
 K  W  C  L  D  P  R  V  V  L  L  S  N  T  Q  T  Q  Y  S  I
gagatccagaacgtggatgtgtatgacgagggcccttacacctgctcggtgcagacagac
 E  I  Q  N  V  D  V  Y  D  E  G  P  Y  T  C  S  V  Q  T  D
aaccacccaaagacctctagggtccacctcattgtgcaagtatctcccaaaattgtagag
 N  H  P  K  T  S  R  V  H  L  I  V  Q  V  S  P  K  I  V  E
atttcttcagatatctccattaatgaagggaacaatattagcctcacctgcatagcaact
 I  S  S  D  I  S  I  N  E  G  N  N  I  S  L  T  C  I  A  T
ggtagaccagagcctacggttacttggagacacatctctcccaaagcggttggctttgtg
 G  R  P  E  P  T  V  T  W  R  H  I  S  P  K  A  V  G  F  V
agtgaagacgaatacttggaaattcagggcatcacccgggaacagtcaggggactacgag
 S  E  D  E  Y  L  E  I  Q  G  I  T  R  E  Q  S  G  D  Y  E
tgcagtgcctccaatgacgtggccgcgccgtggtacggagagtaaaggtcaccgtgaac
 C  S  A  S  N  D  V  A  A  P  V  V  R  R  V  K  V  T  V  N
tatccaccatacatttcagaagccaagggtacaggtgtccccgtgggacaaaaggggaca
 Y  P  P  Y  I  S  E  A  K  G  T  G  V  P  V  G  Q  K  G  T
ctgcagtgtgaagcctcagcagtccctcagcagaattccagtggtacaaggatgacaaa
 L  Q  C  E  A  S  A  V  P  S  A  E  F  Q  W  Y  K  D  D  K
agactgattgaaggaaagaaaggggtgaaagtggaaaacagacctttcctctcaaaactc
 R  L  I  E  G  K  K  G  V  K  V  E  N  R  P  F  L  S  K  L
atcttcttcaatgtctctgaacatgactatgggaactacacttgcgtggcctccaacaag
 I  F  F  N  V  S  E  H  D  Y  G  N  Y  T  C  V  A  S  N  K
ctgggccacaccaatgccagcatcatgctatttgaactaaatgagcctacgagctcaact
 L  G  H  T  N  A  S  I  M  L  F  <u>E  L  N  E  P  T  S  S  T</u>
<u>ttgttgcaagaagtgaaaactacagccctgacccttggaaaggtccaggcgccgtcagc</u>
 <u>L  L  Q  E  V  K  T  T  A  L  T  P  W  K  G  P  A  V  S</u>
gaggtgagcaacggcacgtcgaggagggcaggctgcgtctggctgctgcctcttctggtc
 E  V  S  N  G  T  S  R  R  A  G  C  V  W  L  L  P  L  L  V
ttgcacctgcttctcaaattttga
 L  H  L  L  L  K  F  *
```

FIGURE 9 (page 3 of 3)

+108bp isoform

```
atgggggtctgtgggtacctgttcctgccctggaagtgcctcgtggtcgtgtctctcagg
 M  G  V  C  G  Y  L  F  L  P  W  K  C  L  V  V  V  S  L  R
ctgctgttccttgtacccacaggagtgcccgtgcgcagcggagatgccaccttccccaaa
 L  L  F  L  V  P  T  G  V  P  V  R  S  G  D  A  T  F  P  K
gctatggacaacgtgacggtccggcaggggagagcgccaccctcaggtgcactattgac
 A  M  D  N  V  T  V  R  Q  G  E  S  A  T  L  R  C  T  I  D
aaccgggtcaccgggtggcctggctaaaccgcagcaccatcctctatgctgggaatgac
 N  R  V  T  R  V  A  W  L  N  R  S  T  I  L  Y  A  G  N  D
aagtggtgcctggatcctcgcgtggtccttctgagcaacacccaaacgcagtacagcatc
 K  W  C  L  D  P  R  V  V  L  L  S  N  T  Q  T  Q  Y  S  I
gagatccagaacgtggatgtgtatgacgagggcccttacacctgctcggtgcagacagac
 E  I  Q  N  V  D  V  Y  D  E  G  P  Y  T  C  S  V  Q  T  D
aaccacccaaagacctctagggtccacctcattgtgcaagtatctcccaaaattgtagag
 N  H  P  K  T  S  R  V  H  L  I  V  Q  V  S  P  K  I  V  E
atttcttcagatatctccattaatgaagggaacaatattagcctcacctgcatagcaact
 I  S  S  D  I  S  I  N  E  G  N  N  I  S  L  T  C  I  A  T
ggtagaccagagcctacggttacttggagacacatctctcccaaagcggttggctttgtg
 G  R  P  E  P  T  V  T  W  R  H  I  S  P  K  A  V  G  F  V
agtgaagacgaatacttggaaattcagggcatcacccgggaacagtcaggggactacgag
 S  E  D  E  Y  L  E  I  Q  G  I  T  R  E  Q  S  G  D  Y  E
tgcagtgcctccaatgacgtggccgcgcccgtggtacggagagtaaaggtcaccgtgaac
 C  S  A  S  N  D  V  A  A  P  V  V  R  R  V  K  V  T  V  N
tatccaccatacatttcagaagccaagggtacaggtgtcccgtgggacaaaaggggaca
 Y  P  P  Y  I  S  E  A  K  G  T  G  V  P  V  G  Q  K  G  T
ctgcagtgtgaagcctcagcagtcccctcagcagaattccagtggtacaaggatgacaaa
 L  Q  C  E  A  S  A  V  P  S  A  E  F  Q  W  Y  K  D  D  K
agactgattgaaggaaagaaaggggtgaaagtggaaaacagacctttcctctcaaaactc
 R  L  I  E  G  K  K  G  V  K  V  E  N  R  P  F  L  S  K  L
atcttcttcaatgtctctgaacatgactatgggaactacacttgcgtggcctccaacaag
 I  F  F  N  V  S  E  H  D  Y  G  N  Y  T  C  V  A  S  N  K
ctgggccacaccaatgccagcatcatgctatttt̲g̲a̲t̲g̲g̲c̲t̲c̲c̲t̲a̲a̲g̲c̲t̲g̲a̲c̲t̲g̲t̲g̲g̲g̲a̲a̲
 L  G  H  T  N  A  S  I  M  L  F  *  W  L  L  S  *  L  W  E
t̲c̲a̲t̲a̲a̲t̲t̲g̲g̲a̲a̲c̲t̲a̲a̲atgagcctacgagctcaactttgttgcaagaagtgaaaactaca
 S  *  L  E  L  N  E  P  T  S  S  T  L  L  Q  E  V  K  T  T
gccctgacccttggaaaggtccaggcgccgtcagcgaggtgagcaacggcacgtcgagg
 A  L  T  P  W  K  G  P  A  V  S  E  V  S  N  G  T  S  R
agggcaggctgcgtctggctgctgcctcttctggtcttgcacctgcttctcaaatttga
 R  A  G  C  V  W  L  L  P  L  L  V  L  H  L  L  K  F  *
```

IgLON Re-Expression

- Cell Lines: MDAMB23.1, T47D.
- Azacytidine + Trichostatin A
- Re-expression of OBCAM and NTM
  - confirms epigenetic regulation of transcription OBCAM MS-PCR Primers

| Primer Set | Sense Primer 5'→3' | Antisense Primer 5'→3' | Size | Start Genomic Position | End Genomic Position |
|---|---|---|---|---|---|
| OBCAM1-W | AGGCGTCCAG TGGAGGGGCA CGGGC (SEQ ID NO:2) | CATGCGGCTG CAATCGGCTC CCCG (SEQ ID NO.:1) | 135 | 25 | 160 |
| OBCAM1-M | AGGCGTTTAG TGGAGGGGTA CGGGC (SEQ ID NO:3) | CATCGCGCTA CAATCGACTC CCCG (SEQ ID NO.:4) | 135 | 25 | 160 |
| OBCAM1-U | AGTTGTTTAG TGGAGGGGTA TGGGT (SEQ ID NO:5) | CATCACACTA CAATCAACTC CCCA (SEQ ID NO:6) | 135 | 25 | 160 |
| OBCAM2A-W | CAGCGCGATG GACACGCACA CC (SEQ ID NO:7) | AACGCGGCGC CCCTCGCAGC G (SEQ ID NO.:8) | 229 | 151 | 380 |
| OBCAM2A-M | TAGCGCGATGGATACGTATATC (SEQ ID NO:9) | AACGCGACGC CCCTCGCAAC G (SEQ ID NO.:10) | 229 | 151 | 380 |
| OBCAM2A-U | TAGTGTGATG GATATGTATA TT (SEQ ID NO:11) | AACACAACAC CCCTCACAAC A (SEQ ID NO.:12) | 229 | 151 | 380 |
| OBCAM2B-W | CAACTTCTGC GCTGGCATCG GC (SEQ ID NO:13) | AACGCGGCGC CCCTCGCAGC G (SEQ ID NO:14) | 154 | 226 | 380 |
| OBCAM2B-M | TAATTTTTGC GTTGGTATCG GC (SEQ ID NO:15) | AACGCGACGC CCCTCGCAAC G (SEQ ID NO:16) | 154 | 226 | 380 |
| OBCAM2B-U | TAATTTTTGT GTTGGTATTG GT (SEQ ID NO:17) | AACACAACAC CCCTCACAAC A (SEQ ID NO.:18) | 154 | 226 | 380 |
| OBCAM3A-W | GCGCCGCGTT CTCTCCGCTG GCGC (SEQ ID NO:19) | TCCCGGTGCC GCCTCGGAGC GAGCG (SEQ ID NO:20) | 182 | 371 | 553 |
| OBCAM3A-M | GGTCGCGTT TTTTTCGTTG GCGC (SEQ ID NO:21) | TCCCGATACC GCCTCGAAAC GAACG (SEQ ID NO:22) | 182 | 371 | 553 |
| OBCAM3A-U | GTGTGTGTT TTTTTGTTG GTGT (SEQ ID NO:23) | TCCCAATACC ACCTCAAAAC AAACA (SEQ ID NO:24) | 182 | 371 | 553 |
| OBCAM3B-W | GCGCGGTGCG GGCTCATCCC C (SEQ ID NO:25) | TCCCGGTGCC GCCTCGGAGC GAGCG (SEQ ID NO:26) | 134 | 419 | 553 |
| OBCAM3B-M | GCGCGGTGCG GGTTTATTTT C (SEQ ID NO:27) | TCCCGATACC GCCTCGAAAC GAACG (SEQ ID NO:28) | 134 | 419 | 553 |
| OBCAM3B-U | GTGTGGTGTG GGTTTATTTT T (SEQ ID NO:29) | TCCAATACC ACCTCAAAAC AAACA (SEQ ID NO:30) | 134 | 419 | 553 |

FIG. 12

NTM MS-PCR Primers

| Primer Set | Sense Primer 5'→3' | Antisense Primer 5'→3' | Size | Start Genomic Position | End Genomic Position |
|---|---|---|---|---|---|
| NTM1 1-W | CACAGCCTGG GCCCGGCGCG GC (SEQ ID NO.:31) | TGGCAGCAGC TCCATCCCTG ACCG (SEQ ID NO.:32) | 160 | 30 | 190 |
| NTM1 1-M | TATAGTTTGG GTTCGGCGCG GC (SEQ ID NO.:33) | TAACAACAAC TCCATCCCTA ACCG (SEQ ID NO.:34) | 160 | 30 | 190 |
| NTM1 1-U | TATAGTTTGG GTTTGGTGTG GT (SEQ ID NO.:35) | TAACAACAAC TCCATCCCTA ACCA (SEQ ID NO.:36) | 160 | 30 | 190 |
| NTM1 2-W | CACAGCCTGG GCCCGGCGCG GC (SEQ ID NO.:37) | AGCGAGCGGG CGGGCTTGCG GCG (SEQ ID NO.:38) | 111 | 30 | 141 |
| NTM1 2-M | TATAGTTTGG GTTCGGCGCG GC (SEQ ID NO.:39) | AACGAACGAA CGAACTAACG ACG (SEQ ID NO.:40) | 111 | 30 | 141 |
| NTM1 2-U | TATAGTTTGG GTTTGGTGTG GT (SEQ ID NO.:41) | AACAAACAAA CAAACTAACA ACA (SEQ ID NO.:42) | 111 | 30 | 141 |
| NTM2 1-W | GGCCGCTGAG CTTGGCGTCC GCG (SEQ ID NO.:43) | TGGCCGAGGA GGGAGAGGCC GGGCG (SEQ ID NO.:44) | 121 | 265 | 386 |
| NTM2 1-M | GGTCGTTGAG TTTGGCGTTT GCG (SEQ ID NO.:45) | TAACGAAAA AAAAAAAACC GAACG (SEQ ID NO.:46) | 121 | 265 | 386 |
| NTM2 1-U | GGTTGTTGAG TTTGGTGTTT GTG (SEQ ID NO.:47) | TAACAAAAA AAAAAAAACC AAACA (SEQ ID NO.:48) | 121 | 265 | 386 |
| NTM2 2-W | AGCGAGCTACCGAGCTTGGGGCCGCCG G (SEQ ID NO.:49) | TGGCCGAGGA GGGAGAGGCC GGGCG (SEQ ID NO.:50) | 65 | 321 | 386 |
| NTM2 2-M | AACGAACTACCGAAACTTAAAACCGCC G (SEQ ID NO.:51) | TAACCGAAAA AAAAAAAACC GAACG (SEQ ID NO.:52) | 65 | 321 | 386 |
| NTM2 2-U | AACAAACTACCAAAACTTAAAACCACC A (SEQ ID NO.:53) | TAACCAAAAA AAAAAAAACC AAACA (SEQ ID NO.:54) | 65 | 321 | 386 |
| NTM3 1-W | AGACTCGGAG GAGTCTGCGC (SEQ ID NO.:55) | ACTTCCCCGA ACTCCGGCAG CCG (SEQ ID NO.:56) | 151 | 925 | 1076 |
| NTM3 1-M | AGATTCGGAG GAGTTTGCGC (SEQ ID NO.:57) | ACTTCCCCGA ACTCCGACAA CCG (SEQ ID NO.:58) | 151 | 925 | 1076 |
| NTM3 1-U | AGATTTGGAG GAGTTTGTGT (SEQ ID NO.:59) | ACTTCCCCAA ACTCCAACAA CCA (SEQ ID NO.:60) | 151 | 925 | 1076 |
| NTM3 2-W | TCCCCGCGCC TCCCGGTCGC CGC (SEQ ID NO.:61) | ACTTCCCCGA ACTCCGGCAG CCG (SEQ ID NO.:62) | 121 | 955 | 1076 |
| NTM3 2-M | TTTTCGGTTTTTCGGTCGT CGC (SEQ ID NO.:63) | ACTTCCCCGA ACTCCGACAA CCG (SEQ ID NO.:64) | 121 | 955 | 1076 |
| NTM3 2-U | TTTTGTGTTTTTGGTGTTGT (SEQ ID NO.:65) | ACTTCCCCAA ACTCCAACAA CCA (SEQ ID NO.:66) | 121 | 955 | 1076 |

FIG. 12 (con't.)

Figure 16 (page 1 of 4)

Exon 1 (Coding Sequence) AC027631.4: 166bp

Exon 1 (Coding Sequence) AC027631.4: 166bp

```
54481 cgcttcccga gcccgctggt gcgcggggcg gggaccagg actgtgcggc tgccggagtc
54541 ctgggaagtt gtggctgtcg agaatggggg tctgtgggta cctgttcctg ccctggaagt
54601 gcctcgtgt cgtgtctctc aggctgctgt tccttgtacc cacaggagct gcccgtgcgc
54661 aggaagatgc caccttcccc aaagtctatgg acaacgtgac ggtccggcac cggcagagcg
54721 ccactctcaan nnnnnnnnn nnnnnnnnnn
```

Exon 2 AC012234.6: 233bp

```
75121 ttttagcact gtgttttgtt gtttcattta ctcctcaaaa tgcaacgtct tatttaccat
75181 attatataat ctctccactc tctctcttc ccttcttcct ccctccacca ctccctgcct
75241 cactgcaggt gtaccataga tgacgggta acccgggtgg cctggctaaa ccgcagcacc
75301 atcctctacg ctgggaatga caagtggtcc atagaccctc gtgtgatcat cctggtcaat
75361 acaccaaccc agtacagcat catgatccaa aatgtggatg tgtatgacga aggtccgtac
75421 acctgctctg tgcagacaga caatcatccc aaaacgtccc gggttcacct aatagtgcaa
75481 ggtaagtccc agctggatct gggttgcca ttcccgtcag tgatggaggg gaagaacagt
75541 gttggtgttt gttctacctg tgtgcgaaga cacaaaagtc atcttcctct actgaatcca
75601 gagtttgact atatgtcttg gaatgtttcc catcgaatgg gtacttaact aagtgctgaa
```

Figure 16 (page 2 of 4)

Exon 3 AP000843.3: 126bp

```
36961  atttattata aaaacatgct atacaaaaat ttgtaggcta acacctcctt ttaagtgcaa
37021  agaattattc tcaggtattt cttctatcct gtttccttac agttcctcct cagatcatga
37081  atatctcctc agacatcact gtgaatgagg aagcagtgt gaccctgctg tgtcttgcta
37141  ttggcagacc agagccaact gtgacatgaa gacacctgtc agtcaaggqt aagqtqctqa
37201  cctgqagqac gttttcagag gtagtatgtt aaagtcttgg ctcttatgca caacagagct
37261  tcaggaatca gaaaacattt tgtaatccag tcatagaaaa tcaaaacagc aatatgcacc
37321  aattgctggc tatttcattt caaaagaagg attcatagag gaaatttgct aaatgatggt
```

Exon 4 AP000843.3: 138bp

```
2821  tctgatggct ttttctcttc ctcctcctac aatctctaga tgtgaatatg gttctgtccc
2881  tggttacaca gttcctgat tgtttcctgt ctgcttcttt cttcccagaa gccagggct
2941  ttgtaagtga ggatgagtac ctggagatct ctgacatcaa gcgagaccag tccggggagt
3001  acgaatgcag cgcgttgaac gatgtcgctg cgcccgatgt gcggaaagta aaaatcactg
3061  taaactgtga gtgacctgc agcaggggg ttctggggaa aagacggcac agggagtagg
3121  tggacaatct ggtaatggca gtgccatttt ccaaaggacc caggttcctg ccaacaggaa
3181  aatacttcat cagatggctt tgcccaccat ggcctccgtg ccatttgtcc ctggaatctt
```

Figure 16 (page 3 of 4)

Exon 5 AP000843.3: 121bp

```
3361 aaatgattat tttactggga agagggttg tcacaagaaa tccatttaca tagcaaatgg
3421 ctggatgtgc ccttcatctc tttcacgaaa tcactctgtg tgtgcgtgcg tgcatgcctg
3481 tgcatgtgtg tgtgtgtgtt tcccacagat cctccctata tctcaaaagc caagaacact
3541 ggtgtttcag tcggtcagaa gggcatcctg agctgtgaag cctctgcagt ccccatgct
3601 gaattccagt ggttcaagga agaaaccagg tacctttaa atgacacctg gacagttctg
3661 aagcagagct gatggtctat cccacatgg gagaaggatg aggatgaaga aaaggggaaa
3721 gataaggcaa aacagaaata tactatgccc tcttttgtaa caaagtctat tttacaacg
3781 agaaaaaaaa tggaggagc tgggaagtgg agaaaatgaa ctgaccatga ttctgaatct
```

Exon 6 AP000843.3: 152bp

```
3901 ggcaagagca tcatttccct tctcctcctg ttggacactg aagtgcttag ggtttgagtt
3961 tgaaggacga gattagttgg agaaaagagt ttggtgagga ggagggcctc tttgtagaat
4021 gaattgatag caatgtcttc cctcttgcag gttagccact ggtctggatg gaatgaggat
4081 tgaaacaaa ggccgcatgt ccactctgac tttcttcaat gtttcagaaa aggattatgg
4141 gaactatact tgtgtggcca cgaacaagct tgggaacacc aatgccagca tcacattgta
4201 tggtgagtgc tggaagcctg gatgcagtgg gctcagccac atggggaagc ttgagggact
4261 caggaggag gaagttgcaa tctgcttggc ctgtgtccat ccatcctact caacccacca
4321 cctgtagata agacatactt ctccctgcca ttccccctagc atgccatgca gagatagtta
```

Figure 16 (page 4 of 4)

Exon 7 (Coding Sequence) AP000843.3: 101bp

```
19861 ttgttttagac ttggaatggt cagcggaagg gtggaaggtg ggaagcatgt atgtgtattt
19921 gcttgtcagg gaagaactat ggtgtccttg ggtgtatgct aatgggtctg tctctctctc
19981 ccctacacag ggcctggagc agtcattgat ggtgtaaact cggcctccag agcactggct
20041 tgtctctggc tatcagggac cctcttagcc cacttcttca tcaagtttttg ataagaaatc
20101 ctaggtcctc tgagcaacgc ctgcttctcc atatcacaga ctttaatcta cactgcggag
20161 agcaaaccag cttggcttc ttttgtttt tttctgttat tctagatttg tttctttt
20221 gttttttgttt atttgtttgt ttgcttttat ttccagcttg aatgagtggg gttggggcg
```

Figure 18

Wild Type OBCAM Present in PEO4 Fibroblast DNA:

```
    V  I  I  L  V  N  T  P  T  Q  Y  S  I  M  I  Q
    gtgtgatcatcctggtcaatacaccaacccagtacagcatcatgatccaaa
```

Somatic OBCAM Mis-sense Mutation in PEO1, PEO1CDDP, PEO4 DNA:

```
    V  I  I  L  V  N  T  R  T  Q  Y  S  I  M  I  Q
    gtgtgatcatcctggtcaatacacgaacccagtacagcatcatgatccaaa
```

FIGURE 19

OBCAM CpG Island Bisulphite Sequencing

```
  1  ATTGAGATTT GCCACTTTGG GGACAGGCGT CCAGTGGAGG GGCACGGGCG
 51  TTTCCGAGGT GGGTCCTCGG AGGTGGGTGC ACTCCACCTC TGCGCGGGCC
101  CAGGACAGCG CGCCGTCAGG GCTGGACTTG GCTGGGCGGG GAGCCGATTG
151  CAGCCGCGATG GACACGCACA CCGGTGCCCC ATCTGGCGTG GGCAGGGTAG
201  TTCAGCTCTC CAGGGCGGGG TTTGTCAACT TCTGCGCTGG CATCGGCGAG
251  GGAAGGTGCC AGTGTCAGTT TTCAGTTTGC TGCTTTCCCC AGAACTCCCT
301  CTCCCGCCCT CCCCTCTCCC TCCCCGCTCC CCCCACCCCG CCCCCTCTGT
351  AGGGGAAGCC GCTGCGAGGG GCGCCGCGTT CTCTCCGCTG GCGCGGGTGT
401  CGGGACGGAG CGAAGTGGGC GCGGTGCGGG CTCATCCCCG CAGGCATCCC
451  CAGCCCCGTG GGCGCGGGGC AGGTTAAGGT GGGCGCCCGC CGTCGGGATG
501  AGCGCGCAGT CCGCGCCGCC CGCCAGCCCG CTCGCTCCGA GGCGGCACCG
551  GGAGAAAGTG GCGGTCAGGG ATGGAGCTGC TGCCATGACA ACCCCGGCGG
601  TCCGGGCCCG CGCGCGTCGG GGCTGCTCCC GGGAGGAAGG CGGCGCGGAG
651  CCGGGGGCGG CCGCTGAGCG TGGCGTCCGC GCGTCCCCGC GTCTCGTGCC
701  GCGTCCCCGG AGGAAGCGGG GGCCGCCCGTC CGCCCAGCTC CCCGTCGCGCC
751  CGGAGTTCCC CGCGGGCGGC GCTCCCCCGG CTGGCCGCGA GTCGCCGACC
801  GGGCTGCAGA GGACGGCCAC CGACCGGACG ACCCTGCTGC GCCGGTGCGG
851  TCCCCGCCTT GGAACTTTTT GCCGCCTTGG GGTTCCAGAT GCGAGACCT
```

OBCAM Expression in SKNV3.3 Almost Completely Abolishes Tumourigenicity in *Nude* Mice

CANCER

The present invention relates to cancer and in particular to ovarian and colorectal cancers.

Cancer is a serious disease and a major killer. Although there have been advances in the diagnosis and treatment of certain cancers in recent years, there is still a need for improvements in diagnosis and treatment.

Cancer is a genetic disease and in most cases involves mutations in one or more genes. There are believed to be around 30-40,000 genes in the human genome but only a handful of these genes have been shown to be involved in cancer. Although it is surmised that many more genes than have been presently identified will be found to be involved in cancer, progress in this area has remained slow despite the availability of molecular analytical techniques. This may be due to the varied structure and function of genes which have been identified to date which suggests that cancer genes can take many forms and have many different functions.

Ovarian cancer is the most frequent cause of death from gynaecological malignancies in the Western World, with an incidence of 5,500 new cases every year in England and Wales. It is the fourth most common cause of cancer mortality in American women. The majority of patients with epithelial ovarian cancer present at an advanced stage of the disease. Consequently, the 5 year survival rate is only 30% after adequate surgery and chemotherapy despite the introduction of new drugs such as platinum and taxol (Advanced Ovarian Cancer Trialists Group (1991) *BMJ* 303, 884-893; Ozols (1995) *Semin Oncol.* 22, 61-66). However, patients who have stage I disease (confined to the ovaries) do better with the 5 year survival rate being 70%. It is therefore desirable to have techniques to detect the cancer before metastasis to have a significant impact on survival.

Epithelial ovarian cancer constitutes 70-80% of ovarian cancer and encompasses a broad spectrum of lesions, ranging from localized benign tumours and neoplasms of borderline malignant potential to invasive adenocarcinomas. Histologically, the common epithelial ovarian cancers are classified into several types, that is, serous, mucinous, endometrioid, clear cell, mixed epithelial, and undifferentiated tumours. The heterogeneity of histological subtypes reflects the metaplastic potential of the ovarian surface Mullerian epithelium which shares a common embryological origin with the peritoneum and the rest of the uro-genital system. Germ cell, sex cord/stromal tumours and sarcomas represent the remainder of ovarian cancers. The histogenesis and biological characteristics of epithelial ovarian cancer are poorly understood as are the molecular genetic alterations that may contribute to the development of such tumours or their progression. Epidemiological factors related to ovulation seem to be important, whereby ovarian epithelial cells undergo several rounds of division and proliferative growth to heal the wound in the epithelial surface. These lead to the development of epithelial inclusion cysts and frank malignant tumours may arise from them (Fathalla (1971) *Lancet* 2, 163).

A review of ovarian cancer screening is given in Bell et al (1998) *Health Technology Assessment* 2, 1-50.

Genetic changes in the tumour are critical for the development of cancer. Many chromosomal regions (chromosomes 3, 5, 6, 8, 11, 13, 17, 18, 22, and X) have been implicated to contain tumour suppressor genes involved in tumour progression of sporadic ovarian cancer, but only the p53 gene (chromosome arm 17p) has been found to be frequently mutated (Shelling et al (1995) *Br. J. Cancer* 72, 521-527). The BRCA1 gene (chromosome arm 17q) and the BRCA2 gene (chromosome arm 13q) isolated in 1994 and 1996 respectively, are mutated in a proportion of patients with familial breast/ovarian cancer (Ford & Easton (1995) *Br. J. Cancer* 72, 805-812). Familial ovarian cancer only accounts for 5-10% of all ovarian tumours. In tumours from patients with sporadic ovarian cancer, only five mutations in the BRCA1 gene and four in the BRCA2 gene have been reported (Takahashi et al (1995) *Cancer Res.* 55, 2998-3002; Takahashi et al (1996) *Cancer Res.* 56, 2738-2741) suggesting that they are rare in sporadic ovarian cancer. Mutations in the mismatch repair genes have been reported at a frequency of 10% (Tangi et al (1996) *Cancer Res.* 56, 2501-2505; Fujita et al (1995) *Int. J. Cancer* 64, 361-366; Orth et al (1994) *Proc. Natl. Acad. Sci. USA* 91, 9495-9499). Thus genes that may be more critical in tumour progression in sporadic ovarian cancer have not yet been fully characterised.

WO 96/05306, WO 96/05307 and WO 96/05308 relate to methods and materials used to isolate and detect a human breast and ovarian cancer predisposing gene (BRCA1), some mutant alleles of which are alleged to cause susceptibility to cancer, in particular breast and ovarian cancer.

Tumour suppressor activity has been suggested to be encoded on chromosome 11 (Tanaka et al (1991) *Nature* 349, 340-342; Rimessi et al (1994) *Oncogene* 9, 3467-3474; Satoh et al (1993) *Mol. Carcinogenesis* 7, 157-164; Yoshida et al (1994) *Mol. Carcinogenesis* 9, 114-121; Gabra et al (1996) *Int. J. Oncol.* 8, 625-631; Gabra et al (1996) *Cancer Res.* 56, 950-954; Gabra et al (1995) *Br. J. Cancer* 72, 367-375; EP 0 727 486; Gabra et al (1998) *Proc. AACR* 39, Abstract #4236; and Gabra et al (1998) *Br J. Cancer* 78, Poster P185), but none of these papers identify the candidate gene(s).

Colorectal tumours of the large intestine are a frequent cause of human cancer mortality in the Western world with approximately 19,000 deaths in the UK per annum.

The majority of cancers of the colorectum are adenocarcinomas (Jass and Morson (1987) *J. Clin. Pathol.* 40, 1016-1023; Morson (1974) *Proc. R. Soc. Med.* 67, 451-457). The literature remains divided on the true origins of colorectal carcinomas and it has been proposed that carcinomas may arise both from within existing benign neoplasms (termed adenomas), in what has been termed the adenoma to carcinoma sequence (Muto et al (1975) *Cancer* 30, 2251-2270), or via areas of generalised dysplasia (de novo) without an adenomatous stage. Whilst it is probable that some colorectal cancers originate in adenomas, the majority of adenomas do not appear to progress to carcinoma and indeed may even regress (Knoernschild (1963) *Surg. Forum XIV* 137-138). Whilst evidence on environment, diet, age and sex suggest that these are all risk factors for colorectal cancer, the lack of confirmation of involvement of these factors in all cases suggests an underlying genetic basis for colorectal tumour formation. The majority of colorectal cancers are not associated with clear inherited syndromes although hereditary forms do exist, including Familial Polyposis Coli (FPC), Gardner's Syndrome, Hereditary non-Polyposis Colorectal Cancer (HNPCC) and Turcot's Syndrome.

Several oncogenes and tumour suppressor genes have now been shown to play a definite role in colorectal tumorigenesis, whilst at other loci a correlation between LOH and colorectal cancer is less well defined. Notably, the Barx2 gene was found to be a candidate tumour suppressor in the 11q24-q25 LOH region implicated in ovarian and colorectal cancer (WO 00/77252).

The IgLONs (Immunoglobulin LAMP, OBCAM, and Neurotrimin) are a family of immunoglobulin (Ig) domain-containing cell adhesion molecules, part of the Ig SuperFamily of Ig-domain containing proteins (IgSF). The IgLONs consists of LAMP (Limbic system Associated Membrane Protein), OBCAM/OPCML (Opioid Binding Cell Adhesion Molecule, previously called GP55A), and Neurotrimin (NTM or HNT in humans, or CEPU-1 in chick). Recently, the IgLON family has been shown to include rat neurotractin (kilon—Kindred of LON is the chick homologue. The IgLONs are all extracellular proteins, and are not themselves transmembrane proteins or indeed even directly in contact with the cell membrane. Instead, they are tethered to the cell membrane via a GPI (glycosylphosphatidylinositol) anchor attached near the C-terminus of the protein, which is then inserted into the cell membrane. It is presumed that signalling to the nucleus following IgLON binding is then carried out via trans- and cis-interaction with, as yet undefined, G protein coupled signalling pathways (Clarke and Moss (1997) *Eur. J. Neurosci.* 9:334-41).

The genes encoding OBCAM and NTM are located in the 11q24-q25 region of chromosome 11. The two genes share approximately 80% and 76% identity at the nucleotide and amino acid level, respectively. In the mouse, both proteins are also encoded by distinct genes that appear to be clustered on the proximal end of mouse chromosome 9, in a region syntenic to human chromosome 11q24-q25. It is likely, therefore, that these highly related genes have most likely arisen as a result of an ancestral gene duplication event that occurred at least prior to the divergence of man and mouse (Struyk A F et al (1995) *J. Neurosci* 15(3):2141-56).

IgLON function has primarily been described in the context of neuronal axon guidance and cell-cell contact in brain development. IgLON family members can be co-expressed on a single cell type, and it may be that their relative levels on the cell surface and resultant heterophilic interactions, in addition to homophilic interactions, are important in contextualising their function. Homodimerisation (and also trimerisation) in the plane of a membrane is a feature of NTM cis-interaction (Gil et al (1998) *J. Neuroscience* 18:9312-9325). It has not previously been suggested that members of the IgLON family are involved in cancer and, in particular, it has not previously been suggested that members of the IgLON family may be tumour suppressor genes.

Surprisingly, it has now been found that in addition to the Barx2 tumour suppressor located at 11q24-q25, two further genes in this region are methylated, mutated and/or deleted in cancer. It is believed that the OBCAM and NTM genes are involved in ovarian and colorectal cancer as tumour suppressor genes.

This unexpected observation provides new methods of diagnosis and treatment for cancer, especially for ovarian and colorectal cancers.

A first aspect of the invention provides a method of diagnosing cancer in a patient comprising the steps of
  (i) obtaining a sample containing nucleic acid from the patient; and
  (ii) contacting the said nucleic acid with
    (a) a nucleic acid which hybridises selectively to the OBCAM gene, or a mutant allele thereof, or a nucleic acid which hybridises selectively to OBCAM cDNA, or a mutant allele thereof, or their complement; or
    (b) a nucleic acid which hybridises selectively to the NTM gene, or a mutant allele thereof, or a nucleic acid which hybridises selectively to NTM cDNA, or a mutant allele thereof, or their complement; or
    (c) both (a) and (b).

A second aspect of the invention provides a method of predicting the is relative prospects of a particular outcome of a cancer in a patient comprising the steps of
  (i) obtaining a sample containing nucleic acid from the patient; and
  (ii) contacting the said nucleic acid with
    (a) a nucleic acid which hybridises selectively to the OBCAM gene, or a mutant allele thereof, or a nucleic acid which hybridises selectively to OBCAM cDNA, or a mutant allele thereof, or their complement; or
    (b) a nucleic acid which hybridises selectively to the NTM gene, or a mutant allele thereof, or a nucleic acid which hybridises selectively to NTM cDNA, or a mutant allele thereof, or their complement; or
    (c) both (a) and (b).

Identification of mutations in, or lack of activity of, OBCAM or NTM are believed to be particularly useful for prognosis (i.e. link to outcome) and in determining whether a patient may be suitable for treatment by gene therapy or agonist/mimetic therapy (see below).

In particular, lack of activity of OBCAM due to loss of heterozygosity is thought to be an early event in, for example, ovarian cancer. Loss of NTM heterozygosity is thought to occur later than loss of OBCAM in ovarian cancer. Hence, identification of a lack of activity or mutation in OBCAM may be particularly informative about the possibility of the onset of cancer, whereas analysis of both OBCAM and NTM and identification of lack of activity or mutation (such as deletion) (e.g. by methylation analysis or LOH analysis) in both genes may allow a conclusion as to the degree, or where the method is performed on the same patient at different times, of the progression of the disease.

As discussed further below, the nucleic acid which hybridises selectively to the OBCAM or NTM gene, or a mutant allele thereof, or their complement, may hybridise to the said gene once the said gene has been exposed to a modifying treatment, for example treatment with bisulphite or methylation-sensitive restriction enzymes, as discussed further below. Thus, the method of the first or second aspect of the invention may further comprise the step of exposing the said nucleic acid from the patient to a modifying treatment, for example bisulphite treatment, prior to contacting the said nucleic acid from the patient with the test nucleic acid.

Early detection of ovarian cancer is particularly useful since this cancer type remains asymptomatic until the late stages of tumour development.

Preferably, the patient is a human patient and, generally, reference to OBCAM and NTM is a reference to human OBCAM and human NTM respectively.

It will readily be appreciated by the skilled person that the OBCAM or NTM genes or parts thereof may readily be obtained from other suitable human gene libraries, such as standard cosmid, or yeast artificial chromosome (YAC) or P1-artificial chromosome (PAC) libraries. An OBCAM or NTM cDNA may be used as a probe to identify all or parts of the OBCAM or NTM gene respectively.

OBCAM cDNA sequence is publicly available from GenBank under Accession No. NM_002545. This sequence is also shown in FIG. 7. Further sequences for OBCAM in rat and cow are available from GenBank under the following Accession Nos: M88711 (*Rattus norvegicus*) and X12672 (*Bos taurus*).

The genomic structure of the gene may be determined by comparing the cDNA sequences, for example GenBank cDNA sequences, with the sequence of genomic BAC clones from the GenBank database. The following BAC or PAC clones contain the OBCAM gene: AC027631 (although this sequence in GenBank is incorrectly annotated in referring to chromosome 18; the markers contained within it are all chromosome 11), AC027631, AC012234, AP000843 and AP000912. They can be obtained from the relevant sequencing centres as part of the HGS project.

The OBCAM gene is believed to encompass the D11S4085 genetic marker on chromosome 11. As described in more detail in the Example, the D11S4085 marker has been identified as being lost from one allele of chromosome 11 in ovarian and colorectal cancer (in 56% (24/43) and 32% (8/25) of cases respectively). The D11S4085 marker is known to be located telomeric to the D11S1320 marker. The D11S4085 marker is intronic, in the second intron of OBCAM, approximately 300-600 kb telomeric to D11S1320. Hence, in an alternative embodiment of the first and second aspects of the invention, the step (ii) part (a) may be formulated as:

"a nucleic acid which hybridises selectively to a polynucleotide comprising the microsatellite marker D11S4085, or a mutant allele thereof, or their complement; or".

In this case, the polynucleotide may be any polynucleotide comprising the D11S4085 marker. Preferably, the polynucleotide comprises at least a portion of the OBCAM gene, more preferably all of the OBCAM gene. Still more preferably, the polynucleotide is chromosome 11, or a portion thereof wherein the portion is at least 100, 500, 5000, 10000 or 50000 nucleotides in length. Preferably, the polynucleotide portion is such that it comprises at least 50, 100, 2500, 5000 or 25000 consecutive nucleotides of chromosome 11 on either side of the D11S4085 marker.

D11S4085 is flanked by genomic sequence within intron 2 of OBCAM. This is on BAC AC012234. The partial nucleotide sequence of intron 2 is shown in FIG. 16. However, since FIG. 16 only shows intron/exon boundaries and does not show the full length introns, the marker D11S4085 is not shown in this Figure.

Hence, it will be appreciated that reference to the "OBCAM gene" below may be a reference to a polynucleotide comprising the D11S4085 marker as defined above.

NTM cDNA sequence is publicly available from GenBank under Accession No NM_016522. This sequence is also shown in FIG. 8. A further sequence for NTM in rat is available from GenBank under Accession No NM-017354 (*Rattus norvegicus*).

The genomic structure of the gene may be determined by comparing the cDNA sequences, for example GenBank cDNA sequences, with the sequence of genomic BAC clones from the GenBank database. The following BAC or PAC clones contain the NTM gene: AC012134, AC018368 and AP0000912. They can be obtained from the relevant sequencing centres as part of the HGS project.

Further NTM cDNA sequences may include those of clones 11753149.0.6 and 11753149.0.37 of WO 00/61754 and PRO337 of WO 99/46281.

We have determined further NTM cDNA sequences which are shown in FIG. 9. These sequences are found, for example, in human ovarian surface epithelium. The predominant form in human ovarian surface epithelium appears to be the "+33 bp" form. The "+69 bp" form is another alternative form. Both forms appear to be more abundant in human ovarian surface epithelium than the sequence shown in FIG. 8 and in the database entry referred to above. A further form is the "+108 bp" form, which contains an additional 108 bp, which would be predicted to result in premature protein translation termination and a resultant truncated NTM protein isoform lacking the GPI anchor attachment site in the carboxy terminus. The truncated protein, therefore, would be predicted not to be anchored to the cell membrane via a GPI anchor. This isoform may therefore represent a soluble form of NTM, which might be located extracellularly, and which may potentially interfere with or modulate the normal function of GPI-anchored NTM.

Thus, it is preferred in relation to the first and second aspects of the invention that the nucleic acid which hybridises selectively to the NTM gene, or a mutant allele thereof, or a nucleic acid which hybridises selectively to NTM cDNA, or a mutant allele thereof, or their complement, hybridises to the +33 bp and/or +69 bp and/or +108 bp NTM gene or cDNA or their complement (particularly in relation to cancer of the ovary).

In an embodiment, it is preferred that the said nucleic acid hybridises to the +33 bp and/or +69 bp and/or +108 bp forms of the NTM gene or cDNA or their complement. In a further embodiment it may be preferred that the said nucleic acid further does not hybridise to the "normal" or database NTM gene or cDNA sequence, as exemplified by the cDNA sequence of FIG. 8.

In any event, an OBCAM or NTM cDNA may be readily obtained from a human cDNA library using well known techniques and portions of the genomic clones, or portions of the OBCAM or NTM cDNA sequence shown in FIGS. 7 and 8 or 9 respectively, as a probe. A suitable human cDNA library is one prepared from mRNA isolated from a human ovary or human ovarian tissue or human brain or human lymphoblastoid tissues although different tissue-specific isoforms of NTM may exist in non-ovarian tissues. Once an OBCAM or NTM cDNA or gene or fragment thereof has been identified as said, its nucleotide sequence may readily be determined, for example using Sanger dideoxy sequencing or other methods well known in the art.

It will be appreciated that the OBCAM or NTM gene may exist as a "wild-type" gene or it may exist as mutant alleles which differ in sequence to the wild-type gene, as noted above. By "mutant alleles" is included not only sequences which lead to changes in function or expression of the OBCAM or NTM polypeptide, but allelic variants (or polymorphisms) which have no or only minor effect on the function or expression of the OBCAM or NTM polypeptide. Thus, the nucleic acids which selectively hybridise in the methods of the invention include those that selectively hybridise to the wild-type OBCAM or NTM gene sequence or to the wild-type OBCAM or NTM cDNA sequence (or mRNA sequence) as well as those which selectively hybridise to mutant alleles thereof. Also, it will readily be is appreciated that, as is described in more detail herein, the skilled person can readily identify mutant alleles of the OBCAM or NTM gene and polymorphisms thereof.

An example of a mutant allele of the OBCAM gene is described in Example 5, wherein a cytosine nucleotide in exon 2 (at position 334 in GenBank entry No NM_002545 which is shown in FIG. 7; mutation indicated in FIG. 18) is present as a guanine. This mutation is seen in the ovarian cancer cells lines PEO1 and PEO4, but is not seen in fibroblast DNA isolated from the same patient as PEO1 and PEO4. The mutation produces a change in the encoded amino acid sequence; a "wild type" proline residue is replaced by an arginine in the ovarian cancer cell lines (FIG. 18).

By "the polypeptide OBCAM or NTM" we include a polypeptide whose sequence comprises or consists of the amino acid sequence given in FIG. 7, or 8 or 9, respectively, or whose sequence is encoded by the nucleotide sequence indicated as coding region is FIG. 7, or 8 or 9, respectively, and natural variants thereof. Preferably, the OBCAM polypeptide is one whose amino acid sequence comprises the sequence given in FIG. 7. Preferably, the NTM polypeptide is one whose amino acid sequence comprises the sequence given in FIG. 8 or 9.

By "the polypeptide OBCAM or NTM" we also include any naturally occurring polypeptide which comprises a consecutive 50 amino acid residue portion or natural variants thereof of the polypeptide sequence given in FIG. 7, or FIG. 8 or 9, respectively. Preferably, the polypeptide is a human polypeptide.

By "change in expression of the OBCAM or NTM polypeptide" is included any changes in the OBCAM or NTM gene which lead to changes in expression of the OBCAM or NTM polypeptide respectively. For example, changes in the transcription of the OBCAM or NTM gene will lead to changes in the expression of the OBCAM or NTM polypeptide respectively. Similarly, changes in the translation of OBCAM or NTM mRNA will lead to changes in the expression of the OBCAM or NTM polypeptide respectively.

Mutation of the protein coding sequence of OBCAM or NTM may lead to a loss of function of the OBCAM or NTM protein respectively; similarly, loss of function may be due to transcriptional silencing of the OBCAM or NTM gene or the presence of dominant negative mutations.

It will be appreciated that the methods of the invention defined above may involve either directly or indirectly comparing the results from the test sample with results from a control sample such as from a known non-cancerous (normal) sample or from a known cancerous sample.

It will be appreciated that the nucleic acids which are useful in the method of the invention may readily be defined as those which selectively hybridise to OBCAM or NTM cDNA, or a mutant allele thereof, or their complement. In addition, the methods of the invention include the use of a nucleic acid which selectively hybridises to the OBCAM or NTM gene or cDNA, or mutant alleles thereof whatever the source of the gene or cDNA. An example of a mutant OBCAM allele is shown in FIG. 18 and described in more detail above. Nucleic acids which selectively hybridise to this mutant may be easily determined using the sequences shown in FIGS. 7, 16 and 18.

By "selectively hybridising" is meant that the nucleic acid has sufficient nucleotide sequence similarity with the said DNA or cDNA that it can hybridise under moderately or highly stringent conditions. As is well known in the art, the stringency of nucleic acid hybridization depends on factors such as length of nucleic acid over which hybridisation occurs, degree of identity of the hybridizing sequences and on factors such as temperature, ionic strength and CG or AT content of the sequence. Thus, any nucleic acid which is capable of selectively hybridising as said is useful in the practice of the invention. It is preferred that the nucleic acid which selectively hybridises, selectively hybridises to the human OBCAM or NTM gene or cDNA.

Nucleic acids which can selectively hybridise to the said DNA or cDNA (such as human DNA or cDNA) include nucleic acids which have >95% sequence identity, preferably those with >98%, more preferably those with >99% sequence identity, over at least a portion of the nucleic acid with the said DNA or cDNA. As is well known, human genes usually contain introns such that, for example, a mRNA or cDNA derived from a gene within the said human DNA would not match perfectly along its entire length with the said human DNA but would nevertheless be a nucleic acid capable of selectively hybridising to the said human DNA. Thus, the invention specifically includes nucleic acids which selectively hybridise to a OBCAM or NTM cDNA but may not hybridise to a OBCAM or NTM gene, or vice versa. For example, nucleic acids which span the intron-exon boundaries of the OBCAM or NTM gene may not be able to selectively hybridise to the OBCAM or NTM cDNA respectively. The intron-exon boundaries for the OBCAM gene are shown in FIG. 16; the nucleotide sequence for all introns is incomplete.

Typical moderately or highly stringent hybridisation conditions which lead to selective hybridisation are known in the art, for example those described in *Molecular Cloning, a laboratory manual,* 2nd edition, Sambrook et al (eds), Cold Spring Harbor Laboratory Press, Cold Spring Harbor, N.Y., USA, incorporated herein by reference.

An example of a typical hybridisation solution when a nucleic acid is immobilised on a nylon membrane and the probe nucleic acid is ≧500 bases or base pairs is:

6×SSC (saline sodium citrate)

0.5% sodium dodecyl sulphate (SDS)

100 μg/ml denatured, fragmented salmon sperm DNA

The hybridisation is performed at 68° C. The nylon membrane, with the nucleic acid immobilised, may be washed at 68° C. in 1×SSC or, for high stringency, 0.1×SSC.

20×SSC may be prepared in the following way. Dissolve 175.3 g of NaCl and 88.2 g of sodium citrate in 800 ml of $H_2O$. Adjust the pH to 7.0 with a few drops of a 10 N solution of NaOH. Adjust the volume to 1 liter with $H_2O$. Dispense into aliquots. Sterilize by autoclaving.

An example of a typical hybridisation solution when a nucleic acid is immobilised on a nylon membrane and the probe is an oligonucleotide of between 15 and 50 bases is:

3.0 M trimethylammonium chloride (TMACl)

0.01 M sodium phosphate (pH 6.8)

1 mm EDTA (pH 7.6)

0.5% SDS

100 μg/ml denatured, fragmented salmon sperm DNA 0.1% nonfat dried milk

The optimal temperature for hybridization is usually chosen to be 5° C. below the $T_i$ for the given chain length. $T_i$ is the irreversible melting temperature of the hybrid formed between the probe and its target sequence. Jacobs et al (1988) *Nucl. Acids Res.* 16, 4637 discusses the determination of $T_i$s. The recommended hybridization temperature for 17-mers in 3 M TMACl is 48-50° C.; for 19-mers, it is 55-57° C.; and for 20-mers, it is 58-66° C.

By "nucleic acid which selectively hybridises" is also included nucleic acids which will amplify DNA from the said region of human DNA by any of the well known amplification systems such as those described in more detail below, in particular the polymerase chain reaction (PCR). Suitable conditions for PCR amplification include amplification in a suitable 1× amplification buffer:

10× amplification buffer is 500 mM KCl; 100 mM Tris.Cl (pH 8.3 at room temperature); 15 mM $MgCl_2$; 0.1% gelatin.

A suitable denaturing agent or procedure (such as heating to 95° C.) is used in order to separate the strands of double-stranded DNA.

Suitably, the annealing part of the amplification is between 37° C. and 60° C., preferably 50° C.

Although the nucleic acid which is useful in the methods of the invention may be RNA or DNA, DNA is preferred. Although the nucleic acid which is useful in the methods of the invention may be double-stranded or single-stranded, single-stranded nucleic acid is preferred under some circumstances such as in nucleic acid amplification reactions.

The nucleic acid which is useful in the methods of the invention may be very large, such as 100 kb, if it is double stranded. For example, such large nucleic acids are useful as a template for making probes for use in FISH (fluorescence in situ hybridization) analysis. Typically, the labelled probes used in FISH are generally made by nick-translation or random priming from a genomic clone (such as an insert in a suitable PAC clone). Once made these probes are around 50-1000 nucleotides in length. It is more preferably used as a template for nick-translation or random primer extension as described above. However, for certain diagnostic, probing or amplifying purposes, it is preferred if the nucleic acid has fewer than 10 000, more preferably fewer than 1000, more preferably still from 10 to 100, and in further preference from 15 to 30 base pairs (if the nucleic acid is double-stranded) or bases (if the nucleic acid is single stranded). As is described more fully below, single-stranded DNA primers, suitable for use in a polymerase chain reaction, are particularly preferred.

The nucleic acid for use in the methods of the invention is a nucleic acid capable of hybridising to the OBCAM or NTM gene or the OBCAM or NTM cDNA or mRNA or a mutant thereof. Fragments and variants of this gene, and cDNAs derivable from the mRNA encoded by the gene are also preferred nucleic acids for use in the methods of the invention.

Clearly nucleic acids which selectively hybridise to the gene itself or variants thereof are particularly useful. Fragments of the gene are preferred for use in the method of the invention. Fragments may be made by enzymatic or chemical degradation of a larger fragment, or may be chemically synthesised. By "gene" is included not only the introns and exons but also regulatory regions associated with, and physically close to, the introns and exons, particularly those 5' to the 5'-most exon. By "physically close" is meant within 50 kb, preferably within 10 kb, more preferably within 5 kb and still more preferably within 2 kb. It is believed that the basic promoter and regulatory elements of the OBCAM and NTM gene probably lie up to 200-400 base pairs from the transcriptional start site or start of the coding regions. However, tissue specific or inducible elements may be 50 kb in either direction of the coding regions (exons) or may be in the introns. Such elements of the OBCAM and NTM genes may be identified or located by DNAse hypersensitivity sites (detected on Southern blots) which indicate sites of regulatory protein binding. Alternatively, reporter constructs may be generated using the upstream genomic DNA (i.e. upstream of the 5'-most exon) and, for example, β-galactosidase as a reporter enzyme. Serial deletions and footprinting techniques may also be used to identify the regulatory regions.

The NTM CpG island overlaps with the ATG translation start site and is about 1.1 kb in length. The OBCAM CpG island is approximately 500 bp upstream of the translation start site and is about 900 bp in length. When investigating the methylation status of the NTM or OBCAM gene (as discussed further below), nucleic acids which selectively hybridise to the CpG island of the selected gene may be particularly useful.

By "fragment" of a gene is included any portion of the gene of at least 15 nucleotides in length (whether single stranded or double stranded) but more preferably the fragment is at least 20 nucleotides in length, most preferably at least 50 nucleotides in length and may be at least 100 nucleotides in length or may be at least 500 nucleotides in length. Preferably the fragment is no more than 50 kb and, more preferably, no more than 100 kb.

By "variant" of a gene is included specifically a cDNA, whether partial or full length, or whether copied from any splice variants of mRNA. We also include specifically a nucleic acid wherein, compared to the natural gene, nucleotide substitutions (including inversions), insertions and deletions are present whether in the gene or a fragment thereof or in a cDNA. Both variants and fragments will be selected according to their intended purposes; for probing, amplifying or diagnostic purposes, shorter fragments but with a greater degree of sequence identity (e.g. at least 80%, 90%, 95% or 99%) will generally be required. An example of a variant of the OBCAM gene (and corresponding cDNA) includes the mutant with a cytosine to guanine substitution at nucleotide 334 as numbered in FIG. 7 and shown in FIG. 18.

It is particularly preferred if the nucleic acid for use in the methods of the invention is an oligonucleotide primer which can be used to amplify a portion of the gene or cDNA.

Preferred nucleic acids for use in the invention are those that selectively hybridise to the OBCAM or NTM gene or cDNA and do not hybridise to other genes or cDNAs. Such selectively hybridising nucleic acids can be readily obtained, for example, by reference to whether or not they hybridise to the OBCAM or NTM cDNA as described in FIGS. 7 and 8 or 9 respectively.

Preferably, the methods of the first and second aspects are used to detect the presence or absence of a mutation in any of the said genes or cDNA. In other words, whether a variant gene or cDNA is present. More preferably, it is determined whether the nucleotide corresponding to nucleotide 334 of OBCAM as numbered in FIG. 7 in the nucleic acid from the patient is the same as that in FIG. 7, or not. Such determination may be made using a polynucleotide according to the invention and as described below.

The methods are suitable in respect of any cancer but it is preferred if the cancer is cancer of the ovary, colorectal, or other common adenocarcinomas such as cancer of the breast, lung, prostate and cervix. Additionally, methods relating to OBCAM may also be suitable for leukaemia and methods relating to NTM suitable for pancreas and leukaemia. The methods are particularly suitable in respect of cancer of the ovary or colon; the methods are most suitable in respect of ovarian cancer when the method involves a nucleic acid which selectively hybridises to the OBCAM gene or cDNA or a polynucleotide comprising the D11S4085 marker, and are most suitable in respect of colorectal cancer when the method involves a nucleic acid which selectively hybridises to the NTM gene or cDNA. It will be appreciated that the methods of the invention include methods of prognosis and methods which aid diagnosis. It will also be appreciated that the methods of the invention are useful to the physician or surgeon in determining a course of management or treatment of the patient.

The patient may be any individual in whom a cancer or tumour has been found or is suspected. Particularly preferred patients are those who have a pelvic mass identified by ultrasound and/or who have mildly raised CA125 levels. CA125 is a serum glycopeptide recently identified as Muc16 and is a tumour marker, not just for ovarian cancer but predominantly used in the clinical management of ovarian tumours.

Although it is believed that any sample containing nucleic acid derived from the patient is useful in the methods of the invention, since mutations in the OBCAM or NTM gene may occur in familial cancers and not just sporadic cancers, it is, however, preferred if the nucleic acid is derived from a sample of the tissue in which cancer is suspected or in which cancer may be or has been found. For example, if the tissue in which cancer is suspected or in which cancer may be or has been found is ovary, it is preferred if the sample containing nucleic acid is derived from the ovary of the patient. Samples of ovary may be obtained by surgical excision, laproscopy and biopsy, endoscopy and biopsy, and image-guided biopsy. The image may be generated by ultrasound or technetium-99-labelled antibodies or antibody fragments which bind or locate selectively at the ovary. The well known monoclonal antibody HMFG1 is a suitable antibody for imaging ovarian cancer. Ascites/peritoneal cavity fluid, and peritoneal samples, may be obtained by surgery or laproscopy. Similarly, if the tissue in which cancer is suspected or in which cancer may be or has been found is colon, it is preferred if the sample containing nucleic acid is derived from the colon of the patient; and so on. Colon samples may be obtained by colonoscopy.

Other samples in which it may be beneficial to analyse OBCAM or NTM include lymph node, blood, serum and potential or actual sites of metastasis, for example bone. It is particularly preferred that the sample is blood or lymph node, for example for early diagnosis of occult disease, for example asymptomatic ovarian cancer.

The sample may be directly derived from the patient, for example, by biopsy of the tissue, or it may be derived from the patient from a site remote from the tissue, for example because cells from the tissue have migrated from the tissue to other parts of the body. Alternatively, the sample may be indirectly derived from the patient in the sense that, for example, the tissue or cells therefrom may be cultivated in vitro, or cultivated in a xenograft model; or the nucleic acid sample may be one which has been replicated (whether in vitro or in vivo) from nucleic acid from the original source from the patient. Thus, although the nucleic acid derived from the patient may have been physically within the patient, it may alternatively have been copied from nucleic acid which was physically within the patient. The tumour tissue may be taken from the primary tumour or from metastases.

It will be appreciated that a useful method of the invention includes the analysis of mutations in, or the detection of the presence or absence of the OBCAM or NTM gene in any suitable sample. The sample may suitably be a freshly-obtained sample from the patient, or the sample may be an historic sample, for example a sample held in a library of samples.

Conveniently, the nucleic acid capable of selectively hybridising to the said human DNA and which is used in the methods of the invention further comprises a detectable label.

By "detectable label" is included any convenient radioactive label such as $^{32}P$, $^{33}P$ or $^{35}S$ which can readily be incorporated into a nucleic acid molecule using well known methods; any convenient fluorescent or chemiluminescent label which can readily be incorporated into a nucleic acid is also included. In addition the term "detectable label" also includes a moiety which can be detected by virtue of binding to another moiety (such as biotin which can be detected by binding to streptavidin); and a moiety, such as an enzyme, which can be detected by virtue of its ability to convert a colourless compound into a coloured compound, or vice versa (for example, alkaline phosphatase can convert colourless o-nitrophenylphosphate into coloured o-nitrophenol). Conveniently, the nucleic acid probe may occupy a certain position in a fixed assay and whether the nucleic acid hybridises to the said region of human DNA can be determined by reference to the position of hybridisation in the fixed assay. The detectable label may also be a fluorophore-quencher pair as described in Tyagi & Kramer (1996) *Nature Biotechnology* 14, 303-308.

It will be appreciated that the aforementioned methods may be used for presymptomatic screening of a patient who is in a risk group for cancer. High risk patients for screening include patients over 50 years of age or patients who carry a gene resulting in increased susceptibility (e.g. predisposing versions of BRCA1, BRCA2 or p53); patients with a family history of breast/ovarian cancer; patients with affected siblings; nulliparous women; and women who have a long interval between menarche and menopause. Similarly, the methods may be used for the pathological classification of tumours such as ovarian tumours or colon tumours.

Conveniently, in the methods of the first, second and third aspects of the invention the nucleic acid which is capable of the said selective hybridisation (whether labelled with a detectable label or not) is contacted with a nucleic acid derived from the patient under hybridising conditions. Suitable hybridising conditions include those described above.

It is preferred that if the sample containing nucleic acid derived from the patient is not a substantially pure sample of the tissue or cell type in question that the sample is enriched for the said tissue or cells. For example, enrichment for ovarian cells in a sample such as a blood sample may be achieved using, for example, cell sorting methods such as fluorescent activated cell sorting (FACS) using an ovary cell-selective antibody, or at least an antibody which is selective for an epithelial cell. For example, Cam 5.2, anticytokeratin 7/8, from Becton Dickinson, 2350 Qume Drive, San Jose, Calif., USA, may be useful.

In a preferred embodiment, the invention provides a diagnostic blood test for early ovarian disease or other tumour types. The blood test allows small numbers of circulating tumour cells to be analysed with regard to OBCAM and for NTM, for example with regard to the methylation state of one or both of these genes.

The source of the said sample also includes biopsy material as discussed above and tumour samples, also including fixed paraffin mounted specimens as well as fresh or frozen tissue. The nucleic acid sample from the patient may be processed prior to contact with the nucleic acid which selectively hybridises to OBCAM or NTM. For example, the nucleic acid sample from the patient may be treated by selective amplification, reverse transcription, immobilisation (such as sequence specific immobilisation), or incorporation of a detectable marker.

It is particularly preferred if the methods of the invention include the determination of methylation of, mutations in, or the detection of the presence or absence of, the OBCAM or NTM gene.

The methods of the first or second aspects of the invention may involve sequencing of DNA at one or more of the relevant positions within the relevant region, including direct sequencing; direct sequencing of PCR-amplified exons; differential hybridisation of an oligonucleotide probe designed to hybridise at the relevant positions within the relevant region (conveniently this uses immobilised oligonucleotide probes in, so-called, "chip" systems which are well known in the art); denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP (restriction fragment length polymorphism) assays; heteroduplex analysis; selective DNA amplification using oligonucleotides; fluorescent in-situ hybridisation (FISH) of interphase chromosomes; ARMS-PCR (Amplification Refractory Mutation System-PCR) for specific mutations; cleavage at mismatch sites in hybridised nucleic acids (the cleavage being chemical or enzymic); SSCP single strand conformational polymorphism or DGGE (discontinuous or denaturing gradient gel electrophoresis); analysis to detect mismatch in annealed normal/mutant PCR-amplified DNA; and protein truncation assay (translation and transcription of exons—if a mutation introduces a stop codon a truncated protein product will result). Other methods may be employed such as detecting changes in the secondary structure of single-stranded DNA resulting from changes in the primary sequence, for example, using the cleavase I enzyme. This system is commercially available from Gibco-BRL, Life Technologies, 3 Fountain Drive, Inchinnan Business Park, Paisley PA4 9RF, Scotland.

It will be appreciated that the methods of the invention may also be carried out on "DNA chips". Such "chips" are described in U.S. Pat. No. 5,445,934 (Affymetrix; probe arrays), WO 96/31622 (Oxford; probe array plus ligase or polymerase extension), and WO 95/22058 (Affymax; fluorescently marked targets bind to oligomer substrate, and location in array detected); all of these are incorporated herein by reference.

Detailed methods of mutation detection are described in "Laboratory Protocols for Mutation Detection" 1996, ed. Landegren, Oxford University Press on behalf of HUGO (Human Genome Organisation).

It is preferred if RFLP is used for the detection of fairly large (≧500 bp) deletions or insertions. Southern blots may be used for this method of the invention.

PCR amplification of smaller regions (maximum 300 bp) to detect small changes greater than 3-4 by insertions or deletions may be preferred. Amplified sequence may be analysed on a sequencing gel, and small changes (minimum size 3-4 bp) can be visualised. Suitable primers are designed as herein described.

In addition, using either Southern blot analysis or PCR restriction enzyme variant sites may be detected. For example, for analysing variant sites in genomic DNA restriction enzyme digestion, gel electrophoresis, Southern blotting, and hybridisation specific probe (for example any suitable fragment derived from the OBCAM or NTM cDNA or gene).

For example, for analysing variant sites using PCR DNA amplification, restriction enzyme digestion, gel detection by ethidium bromide, silver staining or incorporation of radionucleotide or fluorescent primer in the PCR.

Other suitable methods include the development of allele specific oligonucleotides (ASOs) for specific mutational events. Similar methods are used on RNA and cDNA for the suitable tissue, such as ovarian or colon tissue.

Whilst it is useful to detect mutations in any part of the OBCAM and/or NTM gene, it is preferred if the mutations are detected in the exons of the gene and it is further preferred if the mutations are ones which change the coding sense. The detection of these mutations is a preferred aspect of the invention. An example of a cytosine to guanine mutation in exon 2 (nucleotide 334 as numbered in GenBank Entry No NM_002545) of the OBCAM gene is described in Example 5.

The methods of the invention also include checking for loss-of-heterozygosity (LOH; shows one copy lost). LOH may be a sufficient marker for diagnosis; looking for mutation/loss of the second allele may not be necessary. LOH of the gene may be detected using polymorphisms in the coding sequence, and introns, of the gene. LOH in a tumour cell, from whatever source, compared to blood is useful as a diagnostic tool, e.g. it may show that the tumour has progressed and requires more stringent treatment.

Particularly preferred nucleic acids for use in the aforementioned methods of the invention are those selected from the group consisting of primers suitable for amplifying nucleic acid.

Suitably, the primers are selected from the group consisting of primers which hybridise to the nucleotide sequences shown in any of the Figures which show OBCAM or NTM gene or cDNA sequences. It is particularly preferred if the primers hybridise to the introns of the OBCAM or NTM gene or if the primers are ones which will prime synthesis of DNA from the OBCAM or NTM gene or cDNA but not from other genes or cDNAs. The intron-exon borders of the OBCAM gene are shown in FIG. 16.

Primers which are suitable for use in a polymerase chain reaction (PCR; Saiki et al (1988) *Science* 239, 487-491) are preferred. Suitable PCR primers may have the following properties:

It is well known that the sequence at the 5' end of the oligonucleotide need not match the target sequence to be amplified.

It is usual that the PCR primers do not contain any complementary structures with each other longer than 2 bases, especially at their 3' ends, as this feature may promote the formation of an artifactual product called "primer dimer". When the 3' ends of the two primers hybridize, they form a "primed template" complex, and primer extension results in a short duplex product called "primer dimer".

Internal secondary structure should be avoided in primers. For symmetric PCR, a 40-60% G+C content is often recommended for both primers, with no long stretches of any one base. The classical melting temperature calculations used in conjunction with DNA probe hybridization studies often predict that a given primer should anneal at a specific temperature or that the 72° C. extension temperature will dissociate the primer/template hybrid prematurely. In practice, the hybrids are more effective in the PCR process than generally predicted by simple $T_m$ calculations.

Optimum annealing temperatures may be determined empirically and may be higher than predicted. Taq DNA polymerase does have activity in the 37-55° C. region, so primer extension will occur during the annealing step and the hybrid will be stabilized. The concentrations of the primers are equal in conventional (symmetric) PCR and, typically, within 0.1- to 1-µM range.

Any of the nucleic acid amplification protocols can be used in the method of the invention including the polymerase chain reaction, QB replicase and ligase chain reaction. Also, NASBA (nucleic acid sequence based amplification), also called 3SR, can be used as described in Compton (1991) *Nature* 350, 91-92 and *AIDS* (1993), Vol 7 (Suppl 2), 5108 or SDA (strand displacement amplification) can be used as described in Walker et al (1992) *Nucl. Acids Res.* 20, 1691-1696. The polymerase chain reaction is particularly preferred because of its simplicity.

When a pair of suitable nucleic acids of the invention are used in a PCR it is convenient to detect the product by gel electrophoresis and ethidium bromide staining. As an alternative to detecting the product of DNA amplification using agarose gel electrophoresis and ethidium bromide staining of the DNA, it is convenient to use a labelled oligonucleotide capable of hybridising to the amplified DNA as a probe. When the amplification is by a PCR the oligonucleotide probe hybridises to the interprimer sequence as defined by the two primers. The oligonucleotide probe is preferably between 10 and 50 nucleotides long, more preferably between 15 and 30 nucleotides long. The probe may be labelled with a radionuclide such as $^{32}P$, $^{33}P$ and $^{35}S$ using standard techniques, or may be labelled with a fluorescent dye. When the oligonucleotide probe is fluorescently labelled, the amplified DNA product may be detected in solution (see for example Balaguer et al (1991) "Quantification of DNA sequences obtained by polymerase chain reaction using a bioluminescence adsorbent" *Anal. Biochem.* 195, 105-110 and Dilesare et al (1993) "A high-sensitivity electrochemiluminescence-based detection system for automated PCR product quantitation" *BioTechniques* 15, 152-157.

PCR products can also be detected using a probe which may have a fluorophore-quencher pair or may be attached to a solid support or may have a biotin tag or they may be detected using a combination of a capture probe and a detector probe.

Fluorophore-quencher pairs are particularly suited to quantitative measurements of PCR reactions (e.g. RT-PCR). Fluorescence polarisation using a suitable probe may also be used to detect PCR products.

Oligonucleotide primers can be synthesised using methods well known in the art, for example using solid-phase phosphoramidite chemistry.

The present invention provides the use of a nucleic acid which selectively hybridises to the OBCAM or NTM gene or to a polynucleotide comprising the microsatellite D11S4085 (as described above), or a mutant allele thereof, or a nucleic acid which selectively hybridises to OBCAM or NTM cDNA or a mutant allele thereof, or their complement in a method of diagnosing cancer or prognosing cancer or determining susceptibility to cancer; or in the manufacture of a reagent for carrying out these methods.

Also, the present invention provides a method of determining the presence or absence, or mutation in, the said OBCAM and/or NTM gene: Preferably, the method uses a suitable sample from a patient. An example of a suitable mutation includes the cytosine to guanine mutation at nucleotide 334 in OBCAM, as described in Example 5 and shown in FIG. 18.

The methods of the invention include the detection of mutations in the OBCAM and/or NTM gene.

The methods of the invention may make use of a difference in restriction enzyme cleavage sites caused by mutation. A non-denaturing gel may be used to detect differing lengths of fragments resulting from digestion with an appropriate restriction enzyme.

An "appropriate restriction enzyme" is one which will recognise and cut the wild-type sequence and not the mutated sequence or vice versa. The sequence which is recognised and cut by the restriction enzyme (or not, as the case may be) can be present as a consequence of the mutation or it can be introduced into the normal or mutant allele using mismatched oligonucleotides in the PCR reaction. It is convenient if the enzyme cuts DNA only infrequently, in other words if it recognises a sequence which occurs only rarely.

In another method, a pair of PCR primers are used which match (i.e. hybridise to) either the wild-type genotype or the mutant genotype but not both. Whether amplified DNA is produced will then indicate the wild-type or mutant genotype (and hence phenotype). However, this method relies partly on a negative result (i.e. the absence of amplified DNA) which could be due to a technical failure. It therefore may be less reliable and/or requires additional control experiments. In a preferred embodiment, one of the primer pair selectively hybridises to a portion of the OBCAM gene which includes nucleotide 334 as numbered in FIG. 7, or the corresponding portion of the OBCAM cDNA.

A preferable method employs similar PCR primers but, as well as hybridising to only one of the wild-type or mutant sequences, they introduce a restriction site which is not otherwise there in either the wild-type or mutant sequences.

It will be appreciated that the nucleic acid which selectively hybridise as said may selectively hybridise to both of the OBCAM and NTM genes because these two genes are located within relative close proximity to each other on chromosome 11. As shown in FIG. 1, the two genes are probably located adjacent to each other.

The nucleic acids which selectively hybridise to the OBCAM and/or NTM gene or to the OBCAM or NTM cDNA are useful for a number of purposes. They can be used in Southern hybridization to genomic DNA and in the RNase protection method for detecting point mutations already discussed above. The probes can be used to detect PCR amplification products. They may also be used to detect mismatches with the OBCAM or NTM gene or mRNA in a sample using other techniques. Mismatches can be detected using either enzymes (e.g. S1 nuclease or resolvase), chemicals (e.g. hydroxylamine or osmium tetroxide and piperidine), or changes in electrophoretic mobility of mismatched hybrids as compared to totally matched hybrids. These techniques are known in the art. Generally, the is probes are complementary to the OBCAM and/or NTM gene coding sequences, although probes to certain introns are also contemplated. A battery of nucleic acid probes may be used to compose a kit for detecting loss of or mutation in the wild-type OBCAM and/or NTM gene. The kit allows for hybridization to the entire OBCAM and/or NTM gene. The probes may overlap with each other or be contiguous. In a preferred embodiment, the probe detects a portion of the OBCAM gene (for example, after amplification as described above), which includes nucleotide 334 as numbered in FIG. 7, or the corresponding nucleotide in the OBCAM cDNA.

If a riboprobe is used to detect mismatches with mRNA, it is complementary to the mRNA of the human OBCAM or NTM gene. The riboprobe thus is an anti-sense probe in that it does not code for the protein encoded by the OBCAM or NTM gene because it is of the opposite polarity to the sense strand. The riboprobe generally will be labelled, for example, radioactively labelled which can be accomplished by any means known in the art. If the riboprobe is used to detect mismatches with DNA it can be of either polarity, sense or anti-sense. Similarly, DNA probes also may be used to detect mismatches.

Nucleic acid probes may also be complementary to mutant alleles of the OBCAM or NTM genes. These are useful to detect similar mutations in other patients on the basis of hybridization rather than mismatches. As mentioned above, the OBCAM and NTM gene probes can also be used in Southern hybridizations to genomic DNA to detect gross chromosomal changes such as deletions and insertions.

According to the diagnostic and prognostic method of the present invention, loss of, or modification of, the wild-type gene function may be detected. The loss may be due to either insertional, deletional or point mutational events. If only a single allele is mutated, an early neoplastic state may be indicated. However, if both alleles are mutated then a malignant state is indicated or an increased probability of malignancy is indicated. The finding of such mutations thus provides both diagnostic and prognostic information. An OBCAM or NTM gene allele which is not deleted (e.g. that on the sister chromosome to a chromosome carrying a gene deletion) can be screened for other mutations, such as insertions, small deletions, and point mutations. We believe that detecting a mutation in a single copy (allele) of the gene is useful. For example, mutation of the OBCAM gene at cytosine 334 as numbered in GenBank Accession No NM_002545 is observed as an early event in the development of ovarian cancer. Loss of the second allele may be necessary for carcinogenesis. If the second copy was lost routinely by a gross mechanism, this could be a useful event to detect. Some mutations of the gene may have a dominant negative effect on the remaining allele. Mutations leading to non-functional gene products may also lead to a malignant state or an increased probability of malignancy. Mutational events (such as point mutations, deletions, insertions and the like) may occur in regulatory regions, such as in the promoter of the gene, leading to loss or diminution of expression of the mRNA. Point mutations may also abolish proper RNA processing, leading to loss of or alteration in the expression of the OBCAM or NTM gene product or to the OBCAM or NTM polypeptide being non-functional or having an altered expression. It is preferred if the amount of OBCAM or NTM mRNA in a test sample is quantified and compared to that present in a control sample. It is also preferred if the splicing patterns or structure of OBCAM or NTM mRNA in a test sample is determined and compared to that present in a control sample. However, the detection of OBCAM or NTM expression is less preferred.

The amount of OBCAM or NTM mRNA is suitably determined per unit mass of sample tissue or per unit number of sample cells and compared this to the unit mass of known normal tissue or per unit number of normal cells. RNA may be quantitated using, for example, northern blotting or quantitative RT-PCR.

The genes have two alleles each, and it will be appreciated that alterations to both alleles may have a greater effect on cell behaviour than alteration to one. It is expected that at least one mutant allele has mutations which result in an altered coding sequence. Modifications to the second allele, other than to the coding sequence, may include total or partial gene deletion, and loss or mutation of regulatory regions.

As mentioned above, it may be useful to determine the loss or inactivation of an allele of both OBCAM and NTM, since loss or inactivation of OBCAM may be an earlier event than loss or inactivation in NTM, and determination of the presence or absence of loss or inactivation in either of the two may be informative as to the stage of progression of the cancer. For example, a patient in whom a deletion (or other loss or inactivation) is identified in OBCAM, but not in NTM, may have an earlier stage of cancer than a patient in whom a loss or inactivation in both OBCAM and NTM is identified. For example, it is believed that subsequent NTM LOH occurs almost exclusively in cases with OBCAM LOH, and that NTM LOH almost never occurs alone. There may be a correlation with higher stage, or grade, or adverse survival. For colorectal cancer, the rates of OBCAM and neurotrimin LOH are considered to be about 32% and 50%, respectively.

Since the progression of a cancer or pre-cancerous condition may be indicated by detection of loss or inactivation in NTM, in addition to loss or inactivation in OBCAM, then it may be useful to perform the method of the first or second aspects of the invention more than once on the same patient.

Hence, the present invention also provides a method of determining the progression of a cancerous disease, for example progression of a tumour, in a patient comprising the steps of
  (i) obtaining a sample nucleic acid from the patient wherein the OBCAM gene of the patient has been lost or inactivated;
  (ii) contacting the said nucleic acid with a nucleic acid which hybridises selectively to the NTM gene or a mutant allele thereof, or a nucleic acid which hybridises selectively to NTM cDNA, or a mutant allele thereof, or their complement.

Preferably, the sample is a sample from the tissue in which the cancer is found or suspected, and more preferably the sample is from ovary or colon.

Such information concerning the progression of, or change in, any cancer or pre-cancerous condition may be useful to the physician in monitoring the efficacy of a treatment, or in diagnosing the precise condition or prognosing or predicting the relative prospects of a particular outcome in a patient.

The invention also includes the following methods: in vitro transcription and translation of OBCAM and/or NTM gene to identify truncated gene products, or altered properties such as substrate binding; immunohistochemistry of tissue sections to identify cells in which expression of the protein is reduced/lost, or its distribution is altered within cells or on their surface; and the use of RT-PCR using random primers, prior to detection of mutations in the region as described above. It is preferred if altered distribution of the OBCAM or NTM polypeptide is screened for.

An example of a mutation which it may be useful to detect is the proline to arginine mutation in the OBCAM polypeptide which is described in Example 5. The mutated residue is located within the first immunoglobulin domain, and may introduce a conformation change in the OBCAM polypeptide. This mutation is believed to be an indicator of cancer, particularly an early indicator of ovarian cancer. Such a mutation in the OBCAM polypeptide may be detected using an antibody which is capable of distinguishing between the wild type (i.e., with no proline to arginine mutation) and the mutant. Such antibodies are described in more detail below.

The methods of the inventions also include detection of inactivation of the OBCAM or NTM gene by investigating its DNA methylation status. DNA methylation of the OBCAM or NTM gene can be assessed using standard techniques such as those described in Herman et al (1996) *Proc. Natl. Acad. Sci. USA* 93, 9821-9826. Aberrant methylation of the OBCAM or NTM gene may be associated with their inactivation.

As will be known to the skilled person, regions of cytosines located 5' to guanines, called CpG islands, are present in the regulatory regions of many genes. These cytosines are generally unmethylated under normal circumstances. However, these cytosines can become methylated within certain genes in association with cancer. These methylated genes can become repressed as a consequence of this both by biallelic methylation or in combination with a second inactivating mechanism (for example LOH or mutation). Methylation Specific PCR (MS-PCR) involves deamination of unmethylated cytosines in genomic DNA to uracil by modification using sodium bisulphite. Methylated cytosines are not deaminated by sodium bisulphite. Primers are designed so mismatches are created, depending on the methylation state of the genomic DNA under investigation. Typical experiments involve two PCR reactions using the same template. One experiment uses a primer that anneals to modified methylated DNA and the other designed to anneal to modified unmethylated DNA, producing specific bands for methylated and unmethylated DNA, respectively, by MS-PCR. Sequencing of MS-PCR products further confirms the extent of CpG island methylation for the genes under test. Examples of suitable primers are shown in FIG. 12.

The following references relate to MS-PCR: Maekawa et al (2001) *Clin Chem Lab Med* Feb; 39(2):121-8; Maekawa M et al (1999) *Biochem Biophys Res Commun* 262(3):671-6.

The Examples show that there is a correlation between the methylation status of the OBCAM or NTM gene and its level of expression: down-regulation of OBCAM or NTM expression correlates with OBCAM or NTM methylation. Thus, the invention includes methods of determining the level of expression of OBCAM or NTM by assessing the level or extent of methylation of the OBCAM or NTM gene, and of using this information in, diagnosing or predicting the relative prospects of a particular outcome of a cancer in a patient.

A still further aspect of the invention provides a method of diagnosing cancer in a patient comprising the steps of (i) obtaining a sample containing the OBCAM and/or NTM gene from the patient;
(ii) determining the degree of methylation of the OBCAM and/or NTM gene;
(iii) comparing the level of methylation of the OBCAM and/or NTM gene from the patient sample with the level of methylation in a control sample; and
(iv) if the patient sample has a higher degree of methylation of the OBCAM and/or NTM gene compared to the control sample this is indicative of cancer.

By determining the degree of methylation is included determining the presence or absence of methylation, for example the presence or absence of methylation on a particular residue or region. Thus, for example, methylation in the primer region may be detected by the presence or absence of a product using MS-PCR as described above, whilst sequencing of the product may indicate whether or how many of the potential methylation sites in the intervening (amplified) region are methylated (and therefore mutated as a consequence of the deaminating agent or treatment, for example bisulphite treatment).

If the patient sample shows methylation of the OBCAM and/or NTM gene whilst the control sample shows no or insignificant methylation of the OBCAM and/or NTM gene this is indicative of cancer. It is considered that methylation may occur in an essentially "all or nothing" manner.

A yet still further aspect of the invention provides a method of predicting the relative prospect of a particular outcome of a cancer patient comprising the steps of
(i) obtaining a sample containing the OBCAM and/or NTM gene from the patient;
(ii) determining the degree of methylation of the OBCAM and/or NTM gene;
(iii) comparing the level of methylation of the OBCAM and/or NTM gene from the patient sample with the level of methylation in a control sample; and
(iv) if the patient sample has a higher degree of methylation of the OBCAM and/or NTM gene compared to the control sample this is indicative of a lower chance of a successful outcome.

By "control sample" we include the meaning of a non-tumorous sample or a sample which may be tumorous but which is at an earlier stage of development than that suspected in the sample of the patient.

Preferably, the control sample is a non-tumorous sample. In the case of measuring the progression of a tumour, it may be preferred if the control sample is a tumorous sample from an earlier stage of development, typically from the same patient.

A progression in the disease or tumour may be identified by determining the degree of methylation in NTM alone, or may be identified by determining the degree of methylation in both NTM and OBCAM. Preferably, the methylation degree is determined in both NTM and OBCAM. By "progression" we include an increase in the likelihood of the tumour becoming malignant.

Unlike colorectal cancer which has a clear progression pathway, ovarian tumours have no premalignant/malignant switch that is detectable. Hence, progression of ovarian disease refers to an increasingly aggressive tumour with, for example, decreased prognosis or increased local spread.

LOH appears to be temporally separated with OBCAM LOH earlier than NTM LOH. Methylation may also be temporally defined for OBCAM and NTM but it is more common for methylation, if it occurs, to occur in both genes at the same time, as discussed in Example 1.

The identification of any methylation at NTM, or of additional methylation at NTM where previously only OBCAM was methylated, may indicate a progression in the disease or tumour from the stage in which no methylation at NTM was identified.

Thus, a still further aspect of the invention provides method of determining the progression of a cancerous disease, for example progression of a tumour, in a patient comprising the steps of
(i) obtaining a sample from the patient containing the NTM gene wherein the OBCAM gene of the patient has been methylated;
(ii) determining the degree of methylation of the NTM gene;
(iii) comparing the level of methylation of the NTM gene from the patient sample with the level of methylation in a control sample;
and if the level of methylation of NTM from the patient sample is increased compared to the control sample, this is indicative of a progression in the disease or tumour.

The tumour may be benign or malignant. As described above in relation to the first and second aspects of the invention, it is preferred if the tumour is an ovarian or colorectal tumour, and it is also preferred if the sample is a sample of the tissue in which cancer is suspected or the tumour is found.

Methods for determining methylation differences between nucleic acids are well known in the art and include (a) the use of methylation sensitive single nucleotide primer extension (Ms-SNuPE); (b) digestion of genomic DNA with methylation sensitive restriction enzymes by Southern analysis; and (c) PCR-based methylation assays utilizing digestion of genomic DNA with methylation-sensitive restriction enzymes prior to PCR amplification. The above methods may be carried out following the digestion or bisulphite-converted DNA. Bisulphite treatment causes unmethylated cytosine in the nucleic acid sample to be converted to uracil but does not cause deamination of methylated cytosine (to thymine).

A further aspect of the invention provides a system (or it could also be termed a kit of parts) for detecting the presence or absence of, or mutation in, the relevant region of human DNA, the system comprising a nucleic acid capable of selectively hybridising to the relevant region of human DNA and a nucleoside triphosphate or deoxynucleoside triphosphate or derivative Do thereof. Preferred nucleic acids capable of selectively hybridising to the relevant region of human DNA are the same as those preferred above. The "relevant region of human DNA" includes the OBCAM or NTM gene or the OBCAM or NTM cDNA. Preferably, the relevant region of human DNA is the OBCAM or NTM gene as herein defined.

Hence, the invention provides a kit of parts comprising a nucleic acid which hybridises selectively to the OBCAM or NTM gene or a mutant allele thereof, and means for detecting a mutation in the OBCAM or NTM gene wherein said mutation is a mutation in OBCAM or NTM found in a cancer cell.

By "mutation" is included insertions, substitutions and deletions. An example of a mutation which the nucleic acid is capable of selectively hybridising to is the OBCAM cytosine to guanine mutation at nucleotide 334 as numbered in FIG. 7.

By "nucleoside triphosphate or deoxynucleoside triphosphate or derivative thereof" is included any naturally occurring nucleoside triphosphate or deoxynucleoside triphosphate such as ATP, GTP, CTP, and UTP, dATP dGTP, dCTP, TTP as well as non-naturally derivatives such as those that include a phosphorothioate linkage (for example αS derivatives).

Conveniently the nucleoside triphosphate or deoxynucleoside triphosphate is radioactively labelled or derivative thereof, for example with $^{32}$P, $^{33}$P or $^{35}$S, or is fluorescently labelled or labelled with a chemiluminescence compound or with digoxygenin.

Conveniently deoxynucleotides are at a concentration suitable for dilution to use in a PCR.

Thus, the invention includes a kit of parts which includes a nucleic acid capable of selectively hybridising to the said relevant region of human DNA and means for detecting the presence or absence of or a mutation in, the said region. Means for detecting the presence or absence of, or a mutation in, the said region include, for example, a diagnostic restriction enzyme or a mutant-specific nucleic acid probe or the like.

A further aspect of the invention provides a kit of parts comprising:
(a) at least two nucleic acids which hybridise selectively to the OBCAM gene or a mutant allele thereof, or at least two nucleic acid which hybridise selectively to OBCAM cDNA or a mutant allele thereof; or
(b) at least two nucleic acids which hybridise selectively to the bisulphite-treated methylated OBCAM gene or a mutant allele thereof; or
(c) at least two nucleic acids which hybridise selectively to the bisulphite-treated unmethylated OBCAM gene or a mutant allele thereof; or
(d) both (a) and (b), or (a) and (c), or (b) and (c), or (a), (b) and (c) and a source of bisulphite.

The invention further provides a kit of parts comprising:
(a) at least two nucleic acids which hybridise selectively to the NTM gene or a mutant allele thereof, or at least two nucleic acid which hybridise selectively to NTM cDNA or a mutant allele thereof; or
(b) at least two nucleic acids which hybridise selectively to the bisulphite-treated methylated NTM gene or a mutant allele thereof, or
(c) at least two nucleic acids which hybridise selectively to the bisulphite-treated unmethylated NTM gene or a mutant allele thereof; or
(d) both (a) and (b) both (a) and (b), or (a) and (c), or (b) and (c), or (a), (b) and (c)

and a source of bisulphite.

The kit may further comprise means for performing an amplification reaction, as discussed further below (for example a PCR reaction) and/or for sequencing an amplification product, which may indicate the presence or absence of methylated CpG within the body of the amplification, for example PCR, product.

Conveniently, these kits which comprise a source of bisulphite further comprise control methylated DNA. Such control DNA is known to be methylated on at least one cytosine, and permits a positive comparison with test DNA. Any methylated human DNA may be used, for example DNA that has been artificially methylated using enzymatic methods. DNA derived from blood may be useful as this represents a renewable source. Methylated human DNA is commercially available from Intergen (Purchase, New York, USA/Oxford, UK): CpGenome Universal Methylated DNA Cat. No. S7821.

Also conveniently, these kits further comprise a DNA polymerase. DNA polymerases are useful for amplifying bisulphite-modified DNA prior to sequence analysis. Use of bisulphite in modifying DNA, and subsequent DNA amplification in investigating the methylation status of the DNA is described above and in the Example.

A further aspect of the invention provides a system for detecting the presence or absence of, or mutation in, the relevant region of DNA, the system comprising a nucleic acid which selectively hybridises to the relevant region of human DNA and a nucleic acid modifying enzyme.

Preferred nucleic acids capable of selectively hybridising to the relevant region of human DNA are the same as those preferred above.

By "mutation" is included insertions, substitutions (including transversions) and deletions.

By "nucleic acid modifying enzyme" is included any enzyme capable of modifying an RNA or DNA molecule.

Preferred enzymes are selected from the group consisting of DNA polymerases, DNA ligases, polynucleotide kinases or restriction endonucleases. A particularly preferred enzyme is a thermostable DNA polymerase such as Taq DNA polymerase. Nucleases such as Cleavase I which recognise secondary structure, for example mismatches, may also be useful.

Detecting mutations in the gene will be useful for determining the appropriate treatment for a patient, e.g. OBCAM and/or NTM gene therapy (see below). Detecting mutations in the gene may be useful to identify a subset of patients whose tumours have this shared characteristic, and can be analysed as a group for prognosis or response to various therapies. An example of a mutation in OBCAM is described in Example 5 and shown in FIG. 18.

Mutations in the gene may be related to response or resistance to certain treatments, this may be investigated using cell lines with known sensitivity to various therapies, or by clinical correlation studies.

It is possible that the genes would be used as part of a panel of markers and tests, the combined results of which would direct therapy. Detecting mutations in either or both of the genes may be useful for monitoring disease spread and load.

Analysis of the genes may be useful for differential diagnosis in the case where mutations in the gene are common in one tumour, but not another. For example, secondary tumours of gastrointestinal origin are frequently found in the ovaries and are difficult to distinguish from tumours of true ovarian origin.

A still further aspect of the invention provides a method of diagnosing cancer in a patient comprising the steps of
(i) obtaining a sample containing protein derived from the patient; and
(ii) determining:
(a) the relative amount, or the cellular location, or physical form, of the OBCAM polypeptide, or the relative activity of, or change in activity of, or altered activity of, the OBCAM polypeptide; or
(b) the relative amount, or the cellular location, or physical form, of the NTM polypeptide, or the relative activity of, or change in activity of, or altered activity of, the NTM polypeptide; or
(c) both (a) and (b).

A yet still further aspect of the invention provides a method of predicting the relative prospects of a particular outcome of a cancer in a patient comprising the steps of
(i) obtaining a sample containing protein derived from the patient; and
(ii) determining:
(a) the relative amount, or the cellular location, or physical form, of the OBCAM polypeptide, or the relative activity of, or change in activity of, or altered activity of, the OBCAM polypeptide; or
(b) the relative amount, or the cellular location, or physical form, of the NTM polypeptide, or the relative activity of, or change in activity of, or altered activity of, the NTM polypeptide; or
(c) both (a) and (b).

The methods of the invention also include the measurement and detection of the OBCAM and/or NTM polypeptide or mutants thereof in test samples and their comparison in a control sample. It may also be useful to detect altered activity of the polypeptide. It will be appreciated that the measurements taken with respect to OBCAM and/or NTM polypeptide (or mutants thereof) in the test sample may be compared to the equivalent measurements in control samples which may be derived from known non-cancerous (normal) cells or derived from known cancerous cells.

The sample containing protein derived from the patient is conveniently a sample of the tissue in which cancer is suspected or in which cancer may be or has been found. These methods may be used for any cancer, but they are particularly suitable in respect of cancer of the ovary, colorectal cancer, and other common adenocarcinomas such as cancer of the breast, lung or upper gastrointestinal tract; the methods are especially suitable in respect of cancer of the ovary or colorectal cancer. Methods of obtaining suitable samples are described in relation to earlier methods.

The methods of the invention involving detection of the OBCAM and/or NTM polypeptide are particularly useful in relation to historical samples such as those containing paraffin-embedded sections of tumour samples.

The relative amount of, or the cellular location of, or the physical form of, the OBCAM or NTM polypeptide may be determined in any suitable way.

The polypeptide sequence of OBCAM is given in the GenBank data library under Accession Nos NM_002545 (see FIG. 7). The polypeptide sequence of NTM is given in the GenBank data library under Accession No NM_016522 (see FIGS. 8 and 9). Polypeptide sequences of NTM may also include those encoded by clones 11753149.0.6 and 11753149.0.37 of WO 00/61754 and PRO337 of WO 99/46281.

By determining the "physical form" we include determining the sequence of the polypeptide, for example, determining the presence of differences such as insertions, deletions, substitutions etc between the wild type sequence as shown in FIG. 7 and the sequence of the polypeptide present in the sample from the patient. It may be useful to determine whether the polypeptide is a variant, such as the mutant described in Example 5 in the case of OBCAM, since such variants may be informative. For example, determining that a sample from a patient contains a variant OBCAM wherein residue 95 (as numbered in the immature polypeptide shown in FIG. 7 and in the corresponding protein reference sequence under GenBank Accession No NP_002536) is an arginine instead of proline may be indicative of ovarian cancer. Since this variant is believed to be detectable from an early stage in ovarian cancer, its detection allows prompt diagnosis, prognosis and a determination of the relative prospects of a particular outcome in that patient, all which allow a more suitable treatment to be selected, thereby improving the chances of a favourable outcome for the patient.

It is preferred if the relative amount of, or cellular location of, or physical form of the OBCAM or NTM polypeptide is determined using a molecule which selectively binds to OBCAM or NTM polypeptide or which selectively binds to a mutant form of OBCAM or NTM polypeptide. As will be known to the skilled person, both OBCAM and NTM are extracellular and secreted cell adhesion molecules and therefore the mature wild-type molecules are not generally intracellular. Suitably, the molecule which selectively binds to OBCAM or NTM or which selectively binds to a mutant of OBCAM or NTM is an antibody. The antibody may also bind to a natural variant or fragment of OBCAM or NTM polypeptide.

Antibodies to OBCAM or NTM can be made by methods well known in the art.

It is preferred if the antibodies used are selective for OBCAM or NTM. By "selective for OBCAM or NTM" we mean that they bind OBCAM or NTM but do not bind substantially to other polypeptides. Preferably the antibody binds selectively only to OBCAM or NTM polypeptide, and more preferable, the antibody binds only to one of OBCAM and NTM, and not to both.

Antibodies which can selectively bind to a mutant form of OBCAM or NTM can be made, for example, by using peptides which encompass the changed amino acid or otherwise modified region of OBCAM or NTM, or by using fusion proteins which express a portion of the OBCAM or NTM polypeptide which includes the changed amino acid or otherwise modified region.

An example of a variant OBCAM (i.e., a mutant OBCAM) polypeptide sequence against which it may be useful to make an antibody, which is capable of selectively binding, is described in Example 5, and the amino acid sequence immediately surrounding the mutated residue is shown in FIG. 18. The mutated amino acid corresponds to residue 95 of the immature (i.e., with the signal peptide still attached) polypeptide, as numbered in FIG. 7. Residue 95 is believed to be located in the first immunoglobulin domain of OBCAM.

In any case, based on the genetic code, it is possible to deduce readily the change in the amino acid sequence. Antibodies which are selective for a mutant OBCAM or NTM polypeptide as herein disclosed form a further aspect of the invention.

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference.

By "the relative amount of OBCAM polypeptide" is meant the amount of OBCAM polypeptide per unit mass of sample tissue or per unit number of sample cells compared to the amount of OBCAM polypeptide per unit mass of known normal tissue or per unit number of normal cells. The relative amount may be determined using any suitable protein quantitation method. In particular, it is preferred if antibodies are used and that the amount of OBCAM is determined using methods which include quantitative western blotting, enzyme-linked immunosorbent assays (ELISA) or quantitative immunohistochemistry. Similarly, by "the relative amount of NTM polypeptide" is meant the amount of NTM polypeptide per unit mass of sample etc, as described above in respect of OBCAM.

The neoplastic condition of lesions can also be detected on the basis of the alteration of wildtype OBCAM or NTM polypeptide. Such alterations can be determined by sequence analysis in accordance with conventional techniques. More preferably, antibodies (polyclonal or monoclonal) are used to detect differences in, or the absence of OBCAM or NTM polypeptide or peptides derived therefrom. The antibodies may be prepared as discussed herein.

Other techniques for raising and purifying antibodies are well known in the art and any such techniques may be chosen to achieve the preparations claimed in this invention. In a preferred embodiment of the invention, antibodies will immunoprecipitate OBCAM or NTM proteins from solution as well as react with OBCAM or NTM protein on Western or immunoblots of polyacrylamide gels. In another preferred embodiment, antibodies will detect OBCAM or NTM proteins in paraffin or frozen tissue sections, using immunocytochemical techniques.

Preferred embodiments relating to methods for detecting OBCAM or NTM or its mutations include enzyme linked immunosorbent assays (ELISA), radioimmunoassay (RIA), immunoradiometric assays (IRMA) and immunoenzymatic assays (IEMA), including sandwich assays using monoclonal and/or polyclonal antibodies. Exemplary sandwich assays are described by David et al in U.S. Pat. Nos. 4,376,110 and 4,486,530, hereby incorporated by reference.

The cellular location of OBCAM or NTM may readily be determined using methods known in the art such as immunocytochemistry in which a labelled antibody (for example, radioactively or fluorescently labelled antibody) is used to bind to OBCAM or NTM and its location within the cell is determined microscopically. For example, it is possible using this methodology to determine whether the OBCAM or NTM is located in the cytoplasm or in the plasma membrane or, if located in both compartments, the proportion of OBCAM or NTM which is located in each compartment. A change in the location of OBCAM or NTM in a test sample compared to a non-cancerous, normal control sample may be indicative of a cancerous state.

Methods for detecting altered cellular distribution include immunohistochemistry (IHC; for example, where the antibody or a secondary antibody which recognises the first, is labelled with an enzyme, a fluorescent tag, a radioisotope) and computer-aided image analysis of IHC stained sections.

The relative activity of OBCAM or NTM can be determined by measuring the activity of the OBCAM or NTM polypeptide per unit mass of sample tissue or per unit number of sample cells and comparing this activity to the activity of the OBCAM or NTM polypeptide per unit mass of known normal tissue or per unit number of normal cells. The relative amount may is be determined using any suitable assay of OBCAM or NTM activity. Preferably, the assay is selective for the OBCAM or NTM polypeptide activity.

The activity of the NTM and OBCAM genes include tumour suppressor activity, neuronal axon guidance, promotion of cellular aggregation and an, as yet poorly defined, cell signalling function.

The invention also provides an antibody which reacts with a mutant OBCAM or NTM polypeptide or fragment thereof, wherein said mutant OBCAM or NTM is a mutant found in a cancer cell. Preferably, the antibody does not react with wild-type OBCAM or NTM polypeptide. Such antibodies are useful in the diagnostic assays and methods of the invention and may be made, for example, by using peptides whose sequence is derived from mutant OBCAM or NTM polypeptide as immunogens. An example of an OBCAM mutant is described in Example 5 and shown in FIG. 18.

The invention also provides a nucleic acid which selectively hybridises to a nucleic acid encoding a mutant OBCAM or NTM polypeptide, which mutant is one found in a cancer cell. Such nucleic acids are useful in the diagnostic assays and methods of the invention.

It will be appreciated that in respect of the certain nucleic acid-based methods of diagnosis, determination of susceptibility and prediction of relative prospects of outcome, the methods involve determining whether the status of OBCAM or NTM nucleic acid (whether DNA or mRNA) is altered in a sample being tested compared to a sample from an equivalent tissue or other source which is known to be normal or disease free.

Peptides based on the mutant sequences may be useful in stimulating an immune response.

A further aspect of the invention provides a method of treating cancer in a patient comprising the step of administering to the patient an agonist of OBCAM or NTM activity. The agonist may function by binding to the external aspect of the cell membrane, for example to the GPI anchor) and interacting with the normal targets of OBCAM or NTM. The agonist may be an antibody or antibody fragment, as known to those skilled in the art or may be a small molecule, for example of less than 5000 Da.

Since OBCAM and NTM are extracellular molecules, a mimetic that reconstitutes their function by binding on the extracellular portion of the cell membrane could achieve the same effect as gene therapy transducing a full-length cDNA. In other words, tumour suppressor gene function in a patient may be reconstituted by administering a small molecule therapeutic to the patient.

A further aspect of the invention provides a method of treating cancer in a patient comprising the step of administering to the patient a nucleic acid which selectively hybridises to the OBCAM or NTM gene or a nucleic acid which hybridises selectively to OBCAM or NTM cDNA.

A further aspect of the invention provides a method of treating cancer in a patient comprising the step of administering to the patient a nucleic acid which encodes the OBCAM and/or NTM polypeptide or a functional variant or portion or fusion thereof.

The invention also includes the administration of all or part of the OBCAM and/or NTM gene or cDNA to a patient with a cancer. Preferably, the cancer to be treated in ovarian cancer or colorectal cancer.

Suitably, the nucleic acid which is administered to the patient is a nucleic acid which encodes the OBCAM and/or NTM polypeptide or a functional variant or portion thereof. Preferably, the OBCAM and/or NTM polypeptide is a wild-type polypeptide or a variant polypeptide which has substantially wild-type activities. It is less preferred if the OBCAM and/or NTM polypeptide is a polypeptide with mutations which are found in cancer cells such as ovarian cancer cells; however, such polypeptides may be useful in provoking an anti-cancer cell immune response. Thus, according to the present invention, a method is also provided of supplying wild-type OBCAM and/or NTM function to a cell which carries mutant OBCAM and/or NTM alleles. Supplying such a function should suppress neoplastic growth of the recipient cells. The wild-type OBCAM and/or NTM gene or a part of the gene may be introduced into the cell in a vector such that the gene remains extrachromosomal. In such a situation, the gene will be expressed by the cell from the extrachromosomal location. If a gene fragment is introduced and expressed in a cell carrying a mutant OBCAM and/or NTM allele, the gene fragment should encode a part of the OBCAM and/or NTM protein which is required for non-neoplastic growth of the cell. More preferred is the situation where the wild-type OBCAM and/or NTM gene or a part thereof is introduced into the mutant cell in such a way that it recombines with the endogenous mutant OBCAM and/or NTM gene present in the cell. Such recombination requires a double recombination event which results in the correction of the OBCAM and/or NTM gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the suitably skilled person. Cells transformed with the wild-type OBCAM and/or NTM gene can be used as model systems to study cancer remission and drug treatments which promote such remission.

As generally discussed above, the OBCAM and/or NTM gene or fragment, where applicable, may be employed in gene therapy methods in order to increase the amount of the expression products of such genes in cancer cells. Such gene therapy is particularly appropriate for use in both cancerous and pre-cancerous cells, in which the level of OBCAM and/or NTM polypeptide is absent or diminished or otherwise changed compared to normal cells. It may also be useful to increase the level of expression of a OBCAM and/or NTM gene even in those tumour cells in which the mutant gene is expressed at a "normal" level, but the gene product is not fully functional or has an altered function.

Gene therapy may be carried out according to generally accepted methods, for example, as described by Friedman, 1991. Cells from a patient's tumour may be first analyzed by the diagnostic methods described herein, to ascertain the production of OBCAM and/or NTM polypeptide and its physical form (i.e. what mutations it contains) in the tumour cells. A virus or plasmid vector (see further details below), containing a copy of the OBCAM and/or NTM gene linked to expression control elements and capable of replicating inside the tumour cells, is prepared. Suitable vectors are known, such as disclosed in U.S. Pat. No. 5,252,479 and PCT published application WO 93/07282. The vector is then injected into the patient, either locally at the site of the tumour or systemically (in order to reach any tumour cells that may have metastasised to other sites). If the transfected gene is not permanently incorporated into the genome of each of the targeted tumour cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g. SV40 (Madzak et al, 1992), adenovirus (Berkner, 1992; Berkner et al, 1988; Gorziglia and Kapikian, 1992; Quantin et al, 1992; Rosenfeld et al, 1992; Wilkinson et al, 1992; Stratford-Perricaudet et al, 1990), vaccinia virus (Moss, 1992), adeno-associated virus (Muzyczka, 1992; Ohi et al, 1990), herpesviruses including HSV and EBV (Margolskee, 1992; Johnson et al, 1992; Fink et al, 1992; Breakfield and Geller, 1987; Freese et al, 1990), and retroviruses of avian (Brandyopadhyay and Temin, 1984; Petropoulos et al., 1992), murine (Miller, 1992; Miller et al, 1985; Sorge et al, 1984; *Mann and Baltimore,* 1985; Miller et al, 1988), and human origin (Shimada et al, 1991; Helseth et al, 1990; Page et al, 1990; Buchschacher and Panganiban, 1992). To date most human gene therapy protocols have been based on disabled murine retroviruses.

It may be preferred, particularly in relation to OBCAM, that the gene therapy vector is not a vaccinia virus vector.

Nonviral gene transfer methods known in the art include chemical techniques such as calcium phosphate coprecipitation (Graham and van der Eb, 1973; Pellicer et al, 1980); mechanical techniques, for example microinjection (Anderson et al, 1980; Gordon et al, 1980; Brinster et al, 1981; Constantini and Lacy, 1981); membrane fusion-mediated transfer via liposomes (Feigner et al, 1987; Wang and Huang, 1989; Kaneda et al, 1989; Stewart et al, 1992; Nabel et al, 1990; Lim et al, 1992); and direct DNA uptake and receptor-mediated DNA transfer (Wolff et al, 1990; Wu et al, 1991; Zenke et al, 1990; Wu et al, 1989b; Wolff et al, 1991; Wagner et al, 1990; Wagner et al, 1991; Cotten et al, 1990; Curiel et al, 1991a; Curiel et al, 1991b). Viral-mediated gene transfer can be combined with direct in vivo gene transfer using liposome delivery, allowing one to direct the viral vectors to the tumour cells and not into the surrounding nondividing cells. Alternatively, the retroviral vector producer cell line can be injected into tumours (Culver et al, 1992). Injection of producer cells would then provide a continuous source of vector particles. This technique has been approved for use in humans with inoperable brain tumours.

Other suitable systems include the retroviral-adenoviral hybrid system described by Feng et al (1997) *Nature Biotechnology* 15, 866-870, or viral systems with targeting ligands such as suitable single chain Fv fragments.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumour deposits, for example, following direct in situ administration (Nabel (1992) *Hum. Gene Ther.* 3, 399-410).

Gene transfer techniques which target DNA directly to ovarian tissue, e.g. epithelial cells of the ovaries, is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

In the case where replacement gene therapy using a functionally wild-type OBCAM and/or NTM is used, it may be useful to monitor the treatment by detecting the presence of OBCAM and/or NTM mRNA or polypeptide, or functional OBCAM and/or NTM, at various sites in the body, including the targeted tumour, sites of metastasis, blood serum, and bodily secretions/excretions, for example urine.

A still further aspect of the invention provides a gene therapy vector which is capable of expressing the OBCAM and/or NTM polypeptide or a functional fragment or variant or fusion thereof in a mammalian cell. Typically, the functional fragment or variant or portion or fusion of the OBCAM or NTM polypeptide has the tumour-suppressing activities of wild-type OBCAM or NTM respectively.

Figure 14:
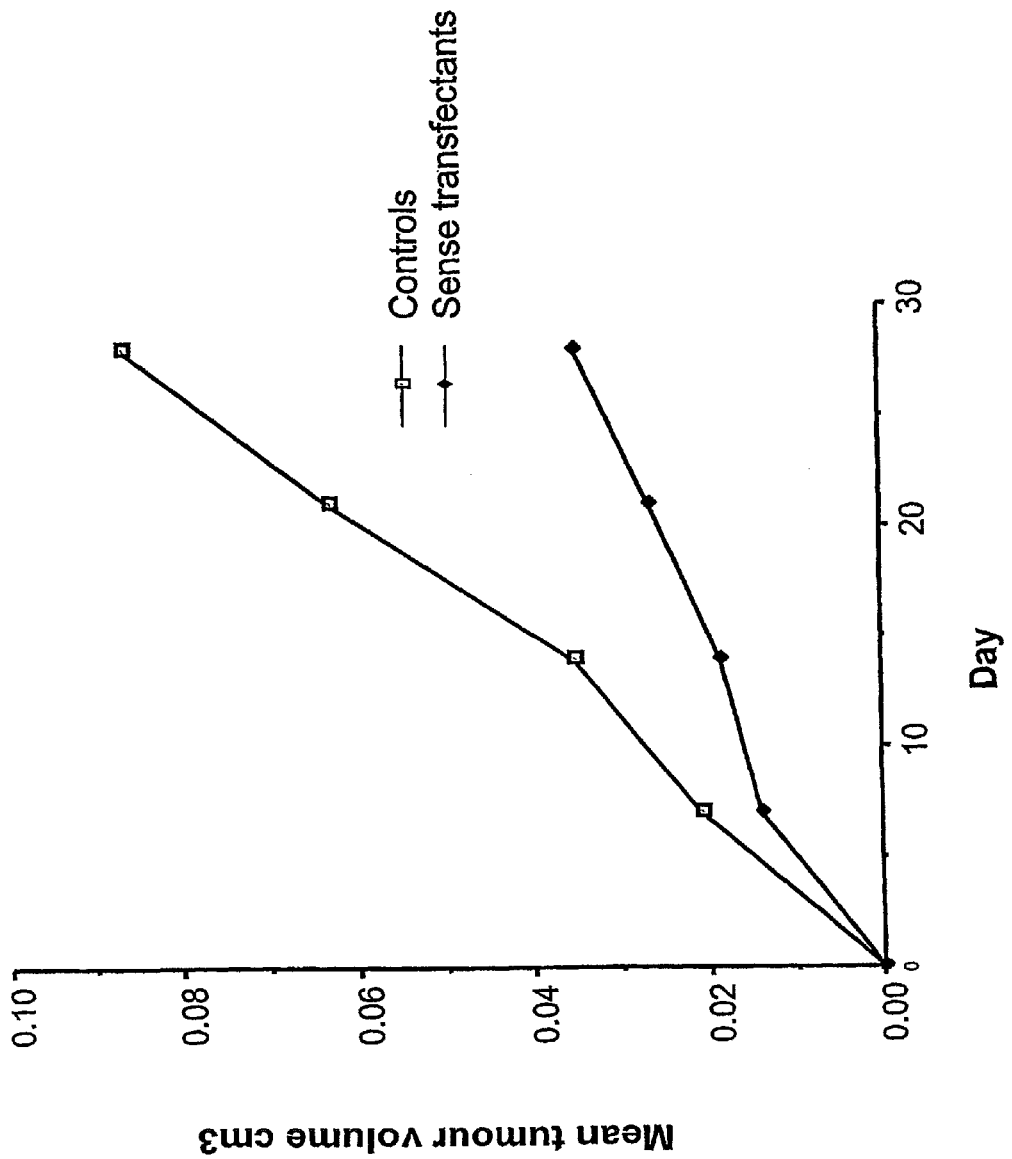

The tumour suppressing activity of OBCAM is shown in FIG. 14, and described in more detail in Example 3.

Preferably, the vector is one which can replicate in a human cell. Preferably, the vector is one which has been described in more detail above in connection with the gene therapy aspects of the invention.

A further aspect of the invention provides a method of treating cancer in a patient comprising the step of administering to the patient an effective amount of OBCAM and/or NTM polypeptide or a fragment or variant or fusion thereof (or other agonist of OBCAM and/or NTM activity, as noted above) to ameliorate the cancer.

Peptides which have OBCAM or NTM activity can be supplied to cells which carry mutant or missing OBCAM or NTM alleles. The sequence of the OBCAM or NTM protein is disclosed in FIGS. 7 and 8 or 9 respectively. Protein can be produced by expression of the cDNA sequence in bacteria, for example, using known expression vectors. Alternatively, OBCAM or NTM polypeptide can be extracted from OBCAM-producing or NTM-producing mammalian cells. In addition, the techniques of synthetic chemistry can be employed to synthesize OBCAM or NTM protein. Any of such techniques can provide the preparation of the present invention which comprises the OBCAM or NTM protein. The preparation is substantially free of other human proteins. This is most readily accomplished by synthesis in a microorganism or in vitro.

The OBCAM or NTM gene or cDNA can be expressed by any suitable method. Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (Yips) and incorporate the yeast selectable markers HIS3, TRP1, LEU2 and URA3. Plasmids pRS413-416 are Yeast Centromere plasmids (YCps)

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

A still further aspect of the invention provides a method of treating cancer in a patient comprising the step of administering to the patient an effective amount of a compound which inhibits the function of a mutant OBCAM or NTM polypeptide found in a tumour cell, or which upregulates expression of wild-type OBCAM or NTM polypeptide.

Suitable compounds for use in this method of the invention include antibodies or fragments or variants thereof which inhibit the activity of the mutant OBCAM or NTM, or antisense molecules which inhibit the expression of the mutant OBCAM and/or NTM.

Also suitable (though less preferred) are methylation inhibitors; as described below and in the Example, the OBCAM and NTM genes are methylated in cancer, and inhibition of this methylation by administering a methylation inhibitor may upregulate expression of the wild type gene or genes. Methylation inhibitors are known in the art and include the compound azacytidine. Other methylation inhibitors include 5 deoxy-azacytidine, or antisense oligos to DNA methyltransferases.

A further aspect of the invention provides a method of treating a cancer in which the OBCAM and/or NTM gene is methylated in a patient comprising the step of administering to the patient an effective amount of a compound which decreases or inhibits DNA methylation.

As discussed below, inhibition of methylation may remove the methyl groups which cause a decrease in expression of the OBCAM and/or NTM genes, which decrease of expression can cause cancer. Hence, decreasing the methylation of OBCAM and/or NTM in cancer cells will increase the expression of OBCAM and/or NTM and may remove, or reduce the rate of, the uncontrolled growth of the cancer cells.

A yet further aspect of the invention provides a method for increasing the expression of the OBCAM and/or NTM gene in a cell comprising the step of administering to the cell an effective amount of a compound which decreases or inhibits DNA methylation.

It may be beneficial to administer the compound in combination with other therapeutic agents indicated herein.

In a preferred embodiment, the cell is one within a patient. It is more preferred if the cell is a cancer or tumour cell within the patient.

Compounds which inhibit the function of a mutant OBCAM or NTM polypeptide found in a tumour cell, or which upregulate expression of wild-type OBCAM or NTM polypeptide or which otherwise act as OBCAM or NTM agonists may be obtained by screening.

Screening compounds by using the OBCAM and/or NTM polypeptide or binding fragment thereof in any of a variety of drug screening techniques may be used.

The OBCAM and/or NTM polypeptide or fragment or a mutant thereof found in a tumour cell employed in such a test may either be free in solution, affixed to a solid support, or borne on a cell surface. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an OBCAM or NTM polypeptide or fragment and the agent being tested, or examine the degree to which the formation of a complex between an OBCAM or NTM polypeptide, or fragment and a known ligand is interfered with by the agent being tested.

Thus, the present invention provides methods of screening for drugs comprising contacting such an agent with an OBCAM or NTM polypeptide or fragment thereof or a mutant thereof found in a tumour cell and assaying (i) for the presence of a complex between the agent and the OBCAM or NTM polypeptide or fragment or mutant, or (ii) for the presence of a complex between the OBCAM or NTM polypeptide or fragment or mutant and a ligand, by methods well known in the art. In such competitive binding assays the OBCAM or NTM polypeptide or fragment or mutant is typically labelled. Free OBCAM or NTM polypeptide or fragment or mutant is separated from that present in a protein:protein complex and the amount of free (i.e. uncomplexed) label is a measure of the binding of the agent being tested to OBCAM or NTM or its interference with OBCAM or NTM:ligand binding, respectively.

Drugs which are able to correct mutant OBCAM and/or NTM function (so that the wild-type function is restored) or that mimic wild-type OBCAM and/or NTM function, are believed to be useful. Similarly, drugs which promote expression of wild-type OBCAM and/or NTM are believed to be useful.

Expression of wild-type OBCAM and/or NTM may be promoted by removing an inhibition of the expression. For example, expression of OBCAM and NTM is inhibited by methylation of CpG islands within the respective genes. Administration of a methylation inhibitor such as azacytidine, 5 deoxy-azacytidine, or antisense oligos to DNA methyltransferases, prevents methylation of the CpG islands and thereby promotes expression of the genes. Hence, a method of upregulating expression of wild-type OBCAM or NTM polypeptide in a patient comprises administering a methylation inhibitor.

Another technique for drug screening provides high throughput screening for compounds having suitable binding affinity to the OBCAM or NTM polypeptides and is described in detail in Geysen, PCT published application WO 84/03564, published on Sep. 13, 1984. Briefly stated, large numbers of different small peptide test compounds are synthesized on a solid substrate, such as plastic pins or some other surface. The peptide test compounds are reacted with OBCAM or NTM polypeptide and washed. Bound OBCAM or NTM polypeptide is then detected by methods well known in the art.

Purified OBCAM or NTM can be coated directly onto plates for use in the aforementioned drug screening techniques. However, non-neutralizing antibodies to the polypeptide can be used to capture antibodies to immobilize the OBCAM or NTM polypeptide on the solid phase.

This invention also contemplates the use of competitive drug screening assays in which neutralizing antibodies capable of specifically binding the OBCAM or NTM polypeptide compete with a test compound for binding to the OBCAM or NTM polypeptide or fragments thereof. In this manner, the antibodies can be used to detect the presence of any peptide which shares one or more antigenic determinants of the OBCAM or NTM polypeptide.

A further technique for drug screening involves the use of host eukaryotic cell lines or cells (such as described above) which have a mutant OBCAM and/or NTM gene. These host cell lines or cells are defective at the OBCAM and/or NTM polypeptide level. The host cell lines or cells are grown in the presence of drug compound. The rate of growth of the host cells is measured to determine if the compound is capable of regulating the growth of OBCAM and/or NTM defective cells.

Screens may also be derived which make use of the OBCAM or NTM promoter sequence operatively linked to a reporter gene. Compounds which selectively increase the expression of the reporter gene may be usefully selected.

Additionally or alternatively, rational drug design may be used. The goal of rational drug design is to produce structural analogues of biologically active polypeptides of interest or of small molecules with which they interact (e.g. agonists, antagonists, inhibitors) in order to fashion drugs which are, for example, more active or stable forms of the polypeptide, or which, e.g. enhance or interfere with the function of a polypeptide in vivo. See, e.g. Hodgson, 1991. In one approach, one first determines the three-dimensional structure of a protein of interest (e.g. OBCAM or NTM polypeptide) or, for example, of the OBCAM or NTM ligand complex, by x-ray crystallography, by computer modelling or most typically, by a combination of approaches. Less often, useful information regarding the structure of a polypeptide may be gained by modelling based on the structure of homologous proteins. An example of rational drug design is the development of HIV protease inhibitors (Erickson et al (1990) *Science* 249, 527-533). In addition, peptides (e.g. OBCAM and NTM polypeptide) are analyzed by an alanine scan (Wells (1991) *Methods Enzymol.* 202, 390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacophore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analogue of the original receptor. The anti-id could then be used to identify and isolate peptides from banks of chemically or biologically produced banks of peptides. Selected peptides would then act as the pharmacophore.

Thus, one may design drugs which have, for example, improved OBCAM and/or NTM polypeptide activity or stability or which act as inhibitors, agonists, antagonists, etc of OBCAM and/or NTM polypeptide activity. By virtue of the availability of cloned OBCAM and NTM sequences, sufficient amounts of the OBCAM and NTM polypeptide may be made available to perform such analytical studies as x-ray crystallography. In addition, the knowledge of the OBCAM and NTM protein sequence provided herein will guide those employing computer modelling techniques in place of, or in addition to x-ray crystallography.

Cells and animals which carry a mutant OBCAM and/or NTM allele can be used as model systems to study and test for substances which have potential as therapeutic agents. The cells are typically cultured epithelial cells. These may be isolated from individuals with OBCAM and/or NTM mutations, either somatic or germline. Alternatively, the cell line can be engineered to carry the mutation in the OBCAM and/or NTM allele, using methods well known in the art. After a test substance is applied to the cells, the neoplastically transformed phenotype of the cell is determined. Any trait of neoplastically transformed cells can be assessed, including anchorage-independent growth, tumourigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant OBCAM and/or NTM alleles, usually from a second animal species, as well as insertion of disrupted homologous genes. Alternatively, the endogenous OBCAM and/or NTM gene(s) of the animals may be disrupted by insertion or deletion mutation or other genetic alterations using conventional techniques (Capecchi, 1989; Valancius and Smithies, 1991; Hasty et al, 1991; Shinkai et al, 1992; Mombaerts et al, 1992; Philpott et al, 1992; Snouwaert et al, 1992; Donehower et al, 1992). After test substances have been administered to the animals, the growth of tumours must be assessed. If the test substance prevents or suppresses the growth of tumours, then the test substance is a candidate therapeutic agent for the treatment of the cancers identified herein. These animal models provide an extremely important testing vehicle for potential therapeutic products.

Active OBCAM and/or NTM molecules can be introduced into cells by microinjection or by use of liposomes, for example. Alternatively, some active molecules may be taken up by cells, actively or by diffusion. Extracellular application of the OBCAM and/or NTM gene product may be sufficient to affect tumour growth. Supply of molecules with OBCAM and/or NTM activity should lead to partial reversal of the neoplastic state. Other molecules with OBCAM and/or NTM activity (for example, peptides, drugs or organic compounds) may also be used to effect such a reversal. Modified polypeptides having substantially similar function are also used for peptide therapy.

Further aspects of the invention provide a pharmaceutical composition comprising a gene therapy vector including a nucleic acid which encodes the OBCAM and/or NTM polypeptide or a functional variant or portion or fusion thereof and pharmaceutically acceptable carrier; a pharmaceutical composition comprising a gene therapy vector including a nucleic acid which selectively hybridises to the OBCAM and/and NTM gene, or a mutant allele thereof, or a OBCAM and/or NTM cDNA, or a mutant allele thereof, and a pharmaceutically acceptable carrier; a pharmaceutical composition comprising OBCAM and/or NTM polypeptide or a fragment or variant or fusion thereof, and a pharmaceutically acceptable carrier.

Suitable gene therapy vectors are described above. Suitable OBCAM and NTM polypeptides are described above. As noted above, it is preferred, particularly in relation to OBCAM, that the gene therapy vector is not a vaccinia virus vector.

By "pharmaceutically acceptable" is included that the formulation is sterile and pyrogen free. Suitable pharmaceutical carriers are well known in the art of pharmacy.

The present invention will now be described in more detail with reference to the following, non limiting, Examples and Figures.

FIG. 1

BAC contig map of the 11q25 region containing the NTM and OBCAM genes, organised according to physical position. The relative position of relevant microsatellite markers is shown. Not to scale

FIG. 2.

Relationship of discrete LOH regions on chromosome 11q24-q25 showing the Barx2 region (region2) and the OBCAM/NTM region (region 5)

FIG. 3.

Figure 2:
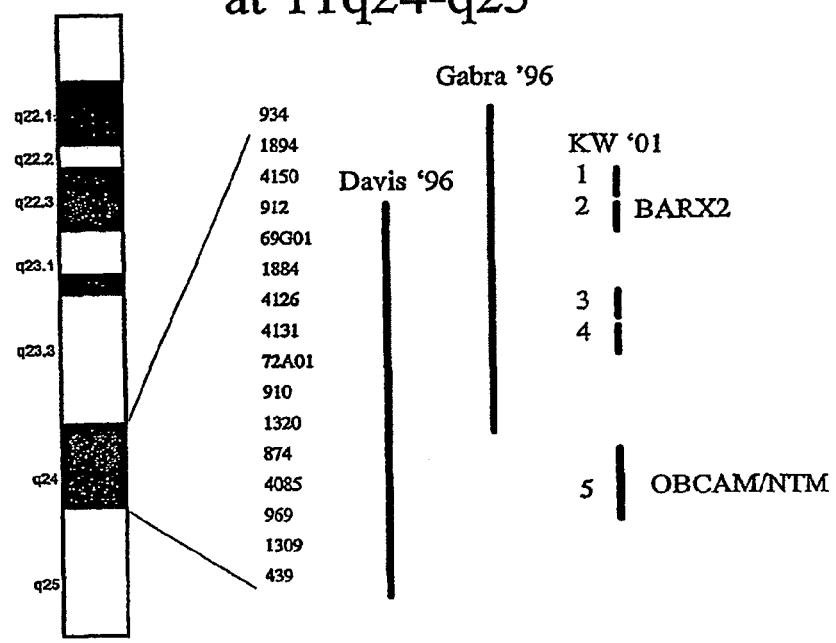
Figure 4:
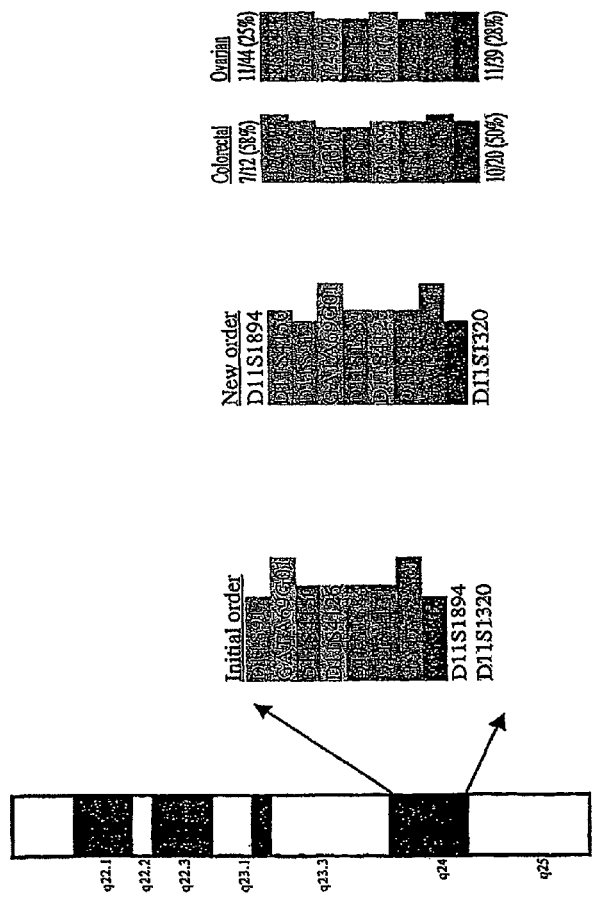
Figure 5:
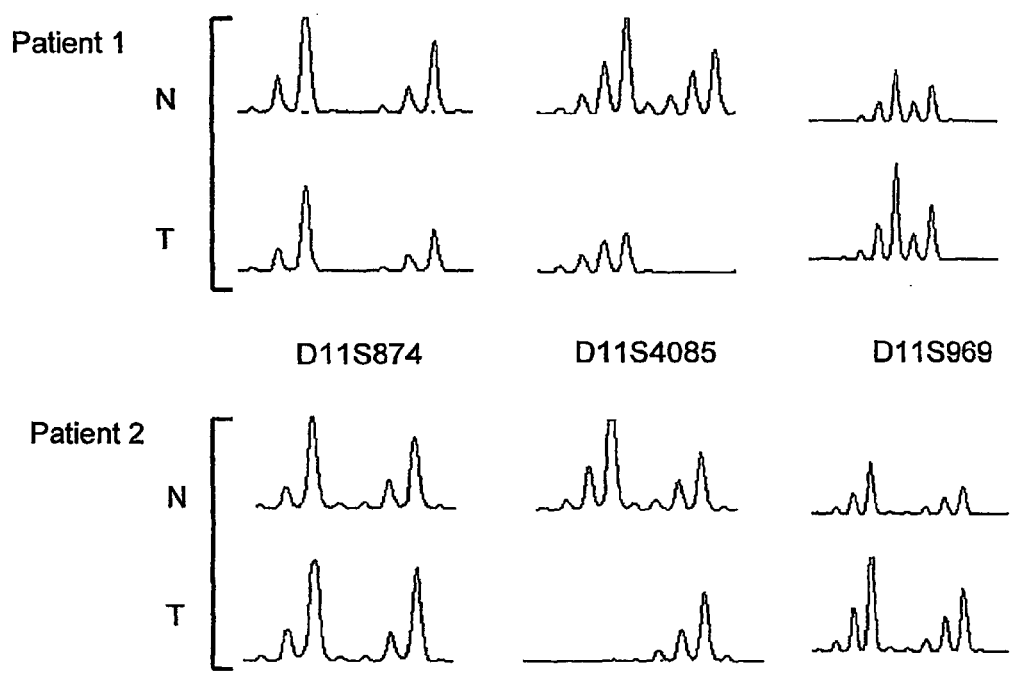

LOH rates for microsatellite markers relating to FIG. 2 from centromere to telomere for ovarian and colorectal cancer.

FIG. 4.

This Figure shows how the markers have been reordered and documents the number of cases with LOH as a percentage of the number of informative cases for each marker. 66% (43/65) of the ovarian tumours and 69% (27/39) of the colorectal tumours had LOH involving at least 1 locus within the 11q24-q25 region. 8 tumours in each group had LOH at all informative loci.

FIG. 5

Examples of D11S4085 LOH. 2 cases with retention of both alleles in blood and complete loss of an allele in ovarian cancer tissue This example of LOH profile at D11S4085 shows retention of heterozygosity at the flanking microsatellite markers D11S874 (centromeric) and D11S969 (telomeric). Markers were amplified by PCR (with one primer for each marker labelled with a fluorescent dye) from Normal (N) and Tumour (T) DNA from two patients with ovarian cancer. PCR products (fluorescently labelled) were size separated on an AB1310 Genetic Analyzer, detected by a laser and data analysed with ABI GeneScan software. The peaks represent the pattern of alleles for each of the markers in the Normal and Tumour DNA for the two patients, Patient 1 and Patient 2. Comparing the allele pattern for D11S4085 between N and T for each patient shows two alleles (heterozygosity) present in the Normal DNA, whereas only a single allele is present in the Tumour DNA, indicating that loss of heterozygosity has occurred. Allele loss has been complete in both cases, indicating a lack of heterogeneity in the Tumour sample. This suggests that loss of the D11S4085 is an early event in the ovarian carcinogenesis. In contrast, the heterozygous allele patterns for the two flanking markers are unchanged between Normal and Tumour for each of the two patients, representing retention of heterozygosity.

FIG. 6

Representative sample of 13 cases of ovarian cancer showing the methylation status for OBCAM and neurotrimin, and the concordance and discordance rates for both within individuals and across the sample.

M=methylated

U=unmethylated

C=concordant

D=discordant

FIG. 7. The nucleotide sequence of human OBCAM cDNA (SEQ ID NO.:98) with the encoded amino acid sequence (SEQ ID NO.:99). The sequence corresponds to GenBank database entry No NM_002545.

FIG. 8.

The nucleotide sequence of human Neurotrimin (NTM) cDNA (SEQ ID NO.:100) with the encoded amino acid sequence (SEQ ID NO.:101). The sequence corresponds to GenBank database entry No NM_016522.

FIG. 9.

NTM isoform sequences. The predominant form in normal human ovarian surface epithelium is the +33 bp form (SEQ ID NO.:102; SEQ ID NO.:103) (about 69%). The +69 bp form (SEQ ID NO.:104; SEQ ID NO.:105) is another alternative form that is a minor isoform (about 19%), compared with the database wild type sequence that forms about 4%. A further minor isoform contains an additional 108 bp (SEQ ID NO.: 106; SEQ ID NO.:107), which would be predicted to result in premature protein translation termination and a resultant truncated NTM protein isoform.

The +33 bp form contains an inserted nucleotide sequence of 33 bp (SEQ ID NO.:102), which is derived from a single alternative exon within the NTM gene. This exon is one of the two exons that contributes to the 69 bp insertion (see below). Shown is the nucleotide sequence with protein translation (SEQ ID NO.:103; below the nucleotide sequence) of the ovarian surface epithelium +33 bp isoform of human neurotrimin. The additional 33 bp of nucleotide sequence and resultant in-frame 11 amino acids are shown in underlined bold in the context of the wild type human NTM sequence (Genbank NM_015622). The stop codon is denoted by *. The in-frame insertion results in the inclusion of an additional 11 amino acids near the C-terminus of the NTM protein: EVKTTALTPWK (SEQ ID NO.:67).

The +69 bp form contains an inserted nucleotide sequence of 69 bp (SEQ ID NO.:104), which is derived from splicing of 2 alternative exons within the NTM gene. Shown is the nucleotide sequence with protein translation (SEQ ID NO.:105; below the nucleotide sequence) of the ovarian surface epithelium +69 bp isoform of human NTM. The additional 69 bp of nucleotide sequence and resultant in-frame 23 amino acids are shown in underlined bold in the context of the wild type human NTM sequence (Genbank NM_015622). The stop codon is denoted by *. The in-frame insertion results in the inclusion of an additional 23 amino acids near the C-terminus of the NTM protein: ELNEPTSSTLLQEVKTTALTPWK (SEQ ID NO.:68).

The +108 bp form contains an inserted nucleotide sequence of 108 bp (SEQ ID NO.:106), which is derived from splicing of 3 alternative exons within the NTM gene. Shown is the nucleotide sequence with protein translation (SEQ ID NO.:107; below the nucleotide sequence) of the ovarian surface epithelium +108 bp isoform of human NTM. The additional 108 bp of nucleotide sequence would be predicted to result in premature protein translation termination and a resultant truncated NTM protein isoform lacking the GPI anchor attachment site in the carboxy terminus. The truncated protein, therefore, would be predicted not to be anchored to the cell membrane via a GPI anchor. This isoform may therefore represent a soluble form of NTM, which might be located extracellularly, and which may potentially interfere with or modulate the normal function of GPI-anchored NTM. The additional 108 bp of nucleotide sequence and protein translation are shown in underlined bold text in the context of the wild type is human NTM sequence (Genbank NM_015622). The stop codons are denoted by *.

Figure 10:
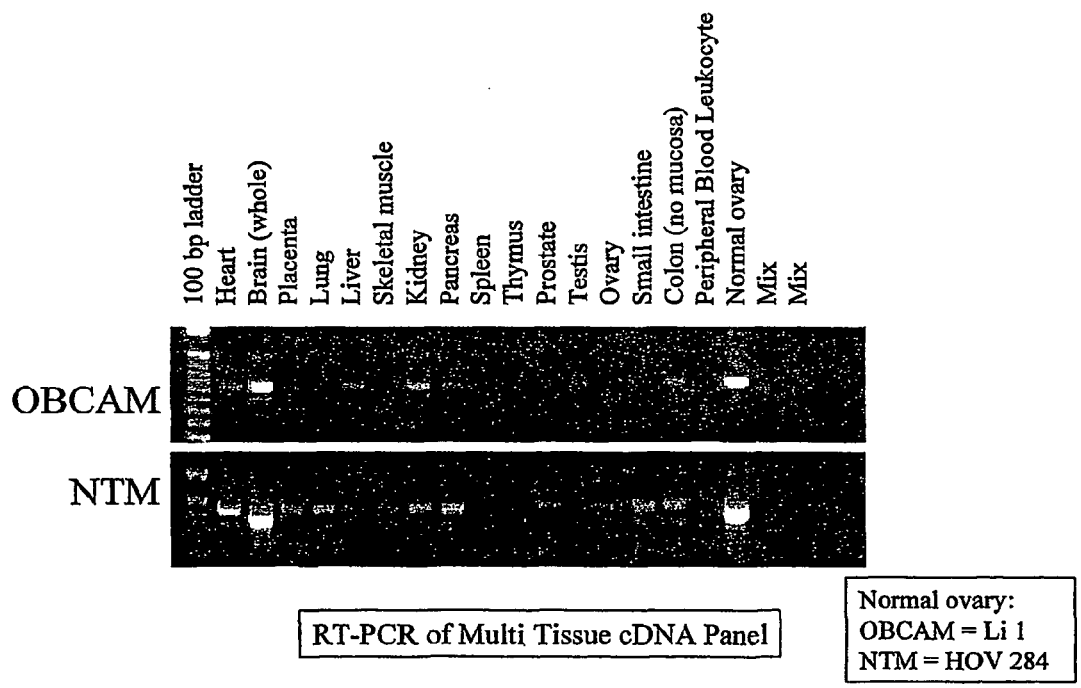

FIG. 10. IgLONs are highly expressed in normal ovary OBCAM and NTM full length coding sequence RT-PCR of multi tissue cDNA panel (BD Clontech) with the addition of a normal ovary sample prepared at ICRF Medical Oncology Unit, Edinburgh, UK. Strongest expression of both genes is observed in brain and the normal ovary samples prepared in-house (i.e. not the Clontech cDNA panel).

Primer Sequences:

OBCAM:

OPCML F1: 5'-AGTTGTGGCTGTCGAGAATG-3' 20' mer nucs 34-53 (SEQ ID NO.:69)

OPCML R1: 5'-TCAGAGGACCTAGGATTTCT-3' 20' mer nucs 1110-1091 (SEQ ID NO.:70)

OBCAM nucleotide numbering from NM_002545

NTM:

NTM F2: 5'-AGTTGTGGCTGTCGAGAATG-3' nucs 248-267 (SEQ ID NO.:71)

NTM R1: 5'-AGAGGTTGCACGATGCAGCT-3' nucs 1600-1581 (SEQ ID NO.:72)

NTM nucleotide numbering from NM_016522

Figure 11:
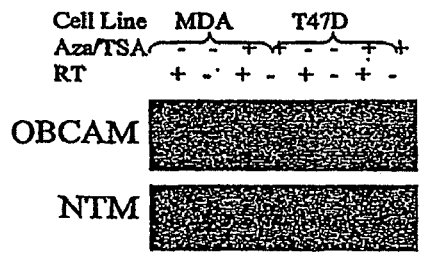

FIG. 11. IgLON Re-expression

MDAMB23.1 and T47D cancer cell lines were cultured in the presence (+) or absence (−) of azacytidine for 4 days plus TSA (Aza/TSA) for the fourth day. OBCAM and NTM RT-PCR shows re-expression of OBCAM in MDAMB23.1 cell line, and NTM re-expression in MDAMB23.1 and T47D cell lines. Reverse transcriptase minus controls are included. NTM RT-PCR shows re-expression of multiple neurotrimin isoforms.

Primers Used were:

OBCAM:

OPCML F4: 5'-TACCATAGATGACCGGGTAA-3' nucs: 221-240 (SEQ ID NO.:73)

OPCML R6: 5'-TTCCGCACATCGGGCGCAGC-3' nucs: 694-675 (SEQ ID NO.:74)

OBCAM nucleotide numbering from NM_002545

NTM:

NTM F3: 5'-ACATGACTATGGGAACTACA-3' nucs 1125-1144 (SEQ ID NO.:75)

NTM R2: 5'-GGAAGTGGCACTCACATCAA-3' nucs 1315-1296 (SEQ ID NO.:76)

NTM nucleotide numbering from NM_016522

FIG. 12. Representative primers useful in detecting methylation of the OBCAM and NTM genes.

Figure 13:
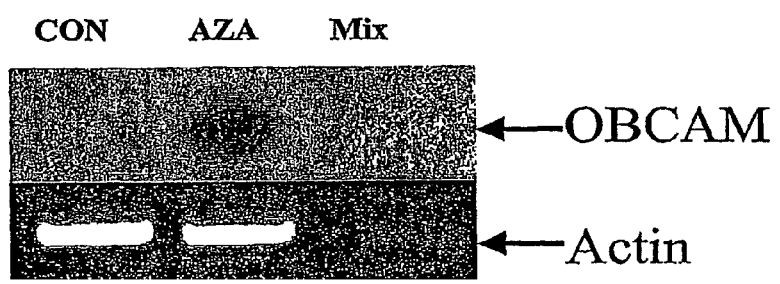

FIG. 13. Demethylation and re-expression of OBCAM in SKNV3.3 cells following 5'-aza 2'-deoxcytidine (AZA) exposure. CON are control untreated SKNV3.3 cells. Mix is a control PCR reaction containing all components except template DNA.

Upper panel: OBCAM RT-PCR of 1st strand cDNA prepared from SKNV3.3 cells after 4 days in culture in the presence (AZA) or absence (CON) of 20 µM 5'-aza 2'-deoxcytidine. Mix refers to a control PCR reaction containing all reaction components except template DNA. OBCAM PCR products were then transferred onto a nylon membrane and hybridised with an OBCAM probe. OBCAM expression is clearly evident following exposure to AZA but is absent in control cells. Lower panel: Actin RT-PCR of 1$^{st}$ strand cDNA of same cell lines as a control for integrity of samples. Actin expression is similar in both treated and untreated SKNV3.3 cells.

FIG. 14. OBCAM transfection into SKVN3.3 cells suppresses sub-cutaneous tumour growth in nude mice.

Graph of the mean tumour volume (cm$^3$) of tumours in nude mice following sub-cutaneous injection of OBCAM sense transfected and control SKVN3.3 cells. Tumour volumes were measured weekly for 4 weeks. The difference in s.c. tumour growth is statistically significant.

Figure 15:
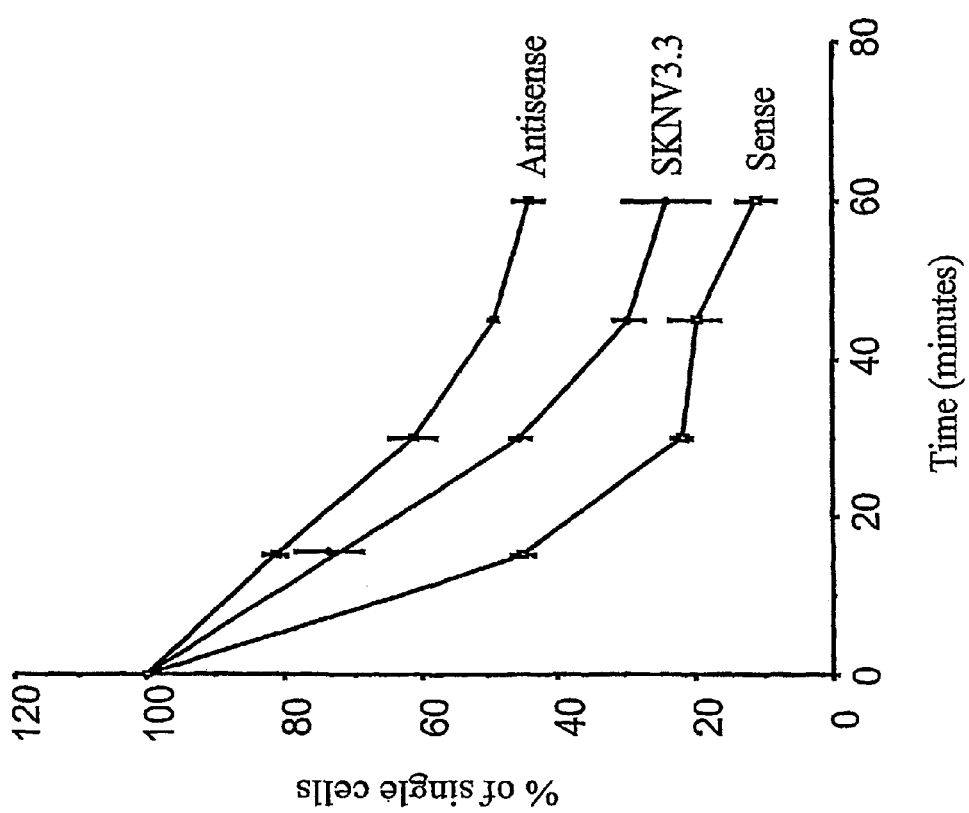

FIG. 15. OBCAM transfection into SKVN3.3 cells enhances cell aggregation.

Graph of the number of single cells remaining in cultures of OBCAM sense transfected, OBCAM antisense transfected, and parent SKNV3.3 cells measured with a haemocytometer at timed intervals. The expression of OBCAM results in a reduced number of single cells remaining in culture, equating with an observed enhanced rate of cell aggregation.

FIG. 16. Predicted Exon Structure of the Human OBCAM Gene.

The exonic sequence is highlighted in bold and intron sequence flanking the exons is in plain text. Nucleotide numberings relate to corresponding to GenBank database sequences as follows. Exon 1 (SEQ ID NO.:111), refers to AC027631.4; Exon 2 (SEQ ID NO.:112), refers to AC012234.6; Exons 3-7 (SEQ ID NOs.:113-117), refers to AP000843.3. The nucleotide sequence for Exon 1 is incomplete in the area encompassing the exon/intron 1 boundary due to lack of available Human Genome Project Sequence in GenBank Accession AC027631.4. Sense and antisense PCR primers for SSCPE are highlighted with single and double underlining, respectively. Predicted exon sizes are given.

Figure 17:
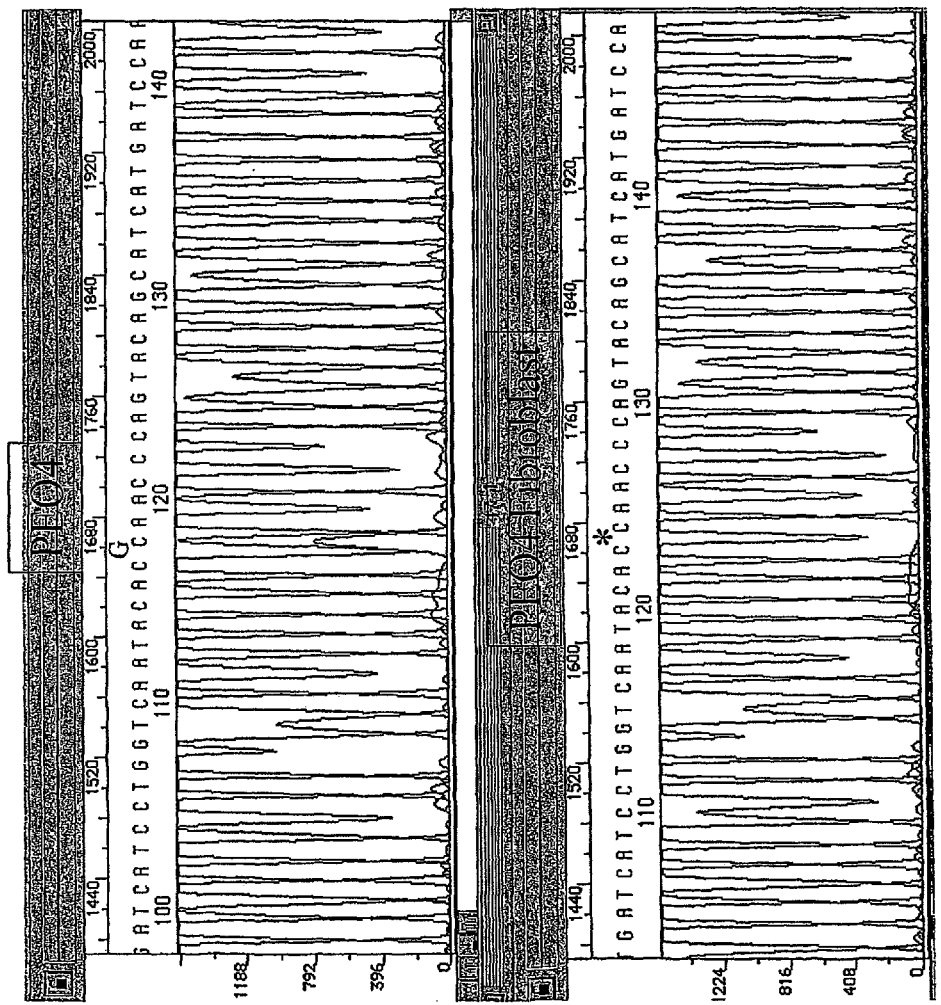

FIG. 17. PEO4 contains a somatic mutation for OBCAM in Exon 2.

Sequence trace files of OBCAM exon 2 F1/R1 SSCPE PCR products from PEO4 (SEQ ID NO:123) and PEO4 Fibroblast (SEQ ID NO:124) DNA obtained using OBCAM EX2 F1 as the sequencing primer. PEO4 Fibroblasts are homozygous for a C nucleotide at the marked position (*); PEO4 is heterozygous at this position and has both C and G alleles.

FIG. 18. PEO4 contains a somatic mis-sense mutation for OBCAM

Ex-Pasy translation of the two alleles identified from the nucleotide sequence the PEO4 OBCAM EX2 F1/R1 SSCPE PCR products (SEQ ID NO.:118; SEQ ID NO.:120), predicts a proline (P) to arginine (R) mis-sense mutation. Somatic nucleotide change: c to g at nucleotide position 75365 (AP000843.3)/334 (NM_002545.2) results in an amino acid substitution: arginine (R) (SEQ ID NO.:121) for proline (P) (SEQ ID NO.:119) at position 95 (immature protein numbering), within the first immunoglobulin domain of OBCAM.

PEO4 Fibroblasts are homozygous for the wild type proline allele, whereas PEO4 (and PEO1 and PEO1CDDP) are heterozygous for the wild type and mutated sequence, containing both the wild type proline and somatic arginine mis-sense mutation. Wild type refers to the reference sequence as contained in the GenBank sequences Nucleotide sequence of wild type OBCAM and of sequence containing a somatic mutation are each shown below their respective protein translation (single letter amino acid code). Affected nucleotides and amino acids are shown in bold. Wild type refers to the reference sequence as contained in the GenBank database (NM_002545.2 and AP 000843.3).

FIG. 19. OBCAM CpG Island Bisulphite Sequencing

The nucleotide sequence of the predicted CpG island of OBCAM, corresponding to nucleotides 53134-54032 (GenBank Accession No. AC027631.4; SEQ ID NO.:122) is shown. The locations of the PCR primers designed to specifically amplify a 529 bp product from sodium bisulphite modified Methylated (M) or Unmethylated (U) DNA are shown in italics, and their sequences detailed below. The PCR product amplified is emboldened, with surrounding sequence in plain text. Methylatable C nucleotides from CpGs are underlined.

Primers:

Sodium bisulphite modified methylated DNA specific:

OBCAM F1M: 5'-AGGCGTTTAGTGGAGGGG-TACGGGC-3' (SEQ ID NO.:77)

OBCAM R3M: 5'-TCCCGATACCGCCTCGAAAC-GAACG-3' (SEQ ID NO.:78)

Sodium bisulphite modified unmethylated DNA specific:

OBCAM F1U: 5'-AGGTGTTTAGTGGAGGGG-TATGGGT-3' (SEQ ID NO.:79)

OBCAM R3U: 5'-TCCCAATACCACCTCAAAA-CAAACA-3' (SEQ ID NO.:80)

Figure 20:
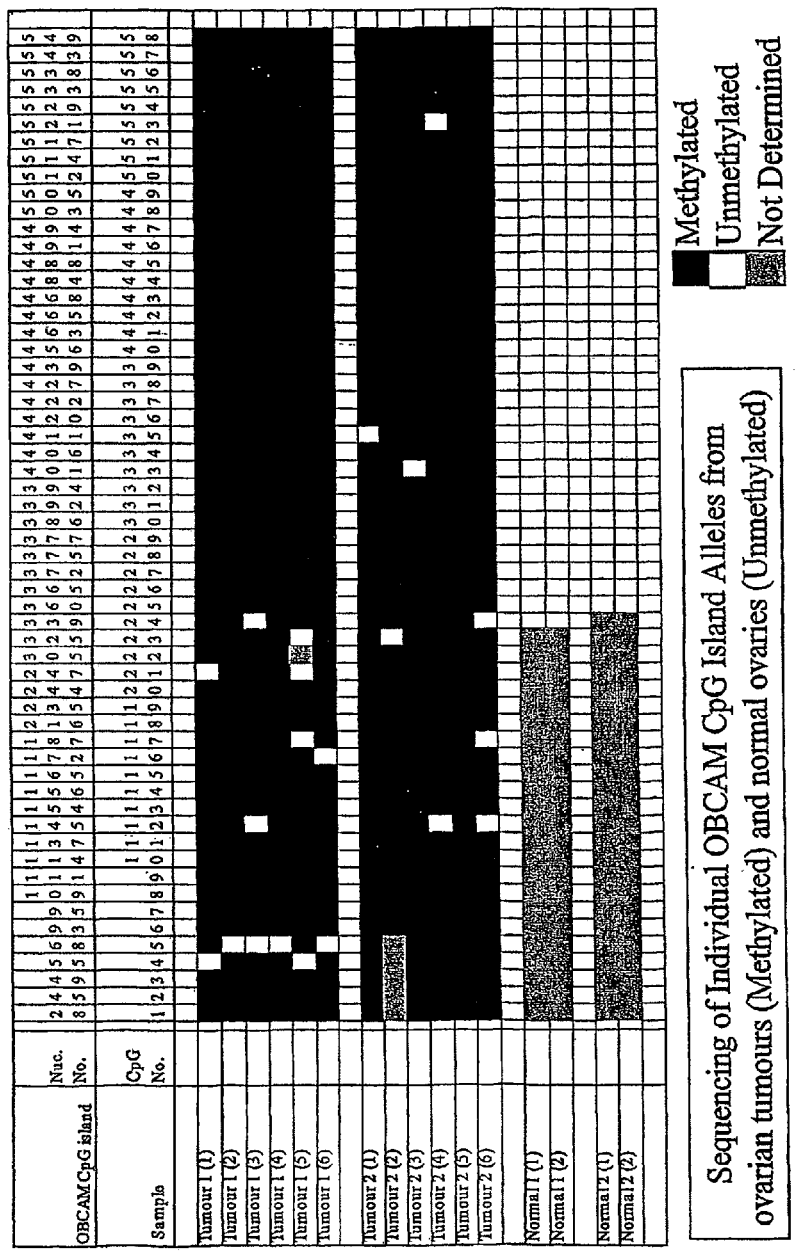

FIG. 20. OBCAM CpG Island is methylated in ovarian tumours and unmethylated in normal ovary.

Figure 21:
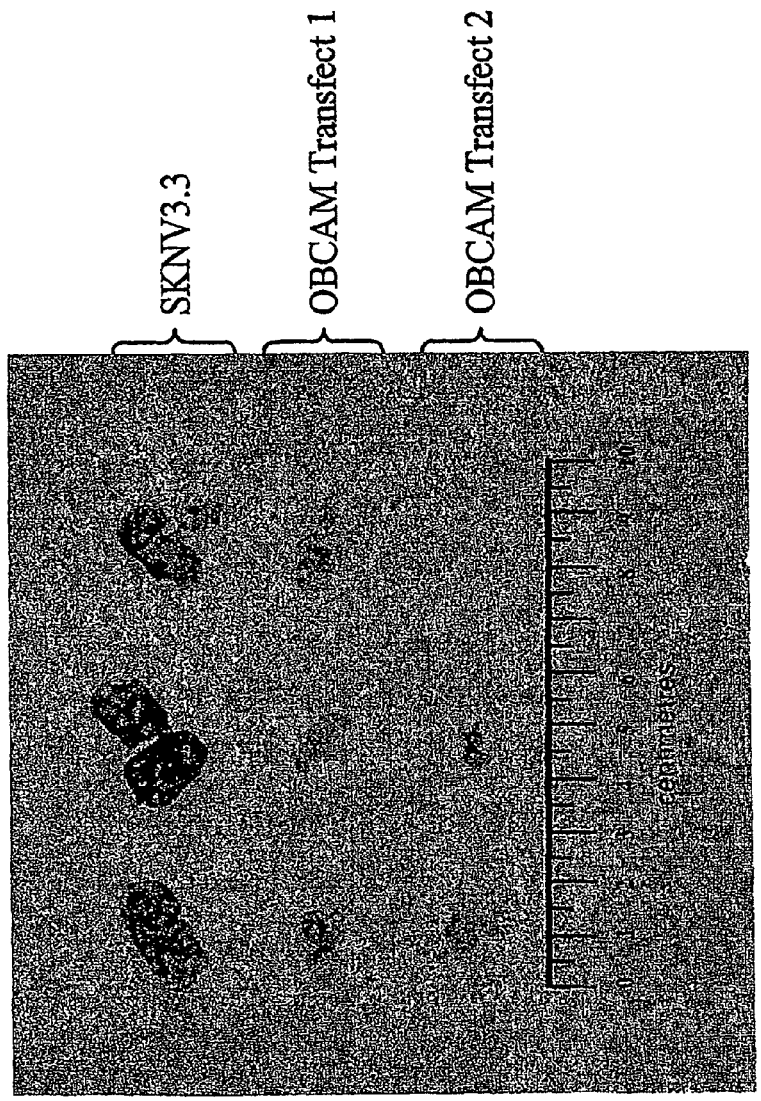

FIG. 21. OBCAM expression in SKNV3.3 almost completely abolishes tumourigenicity in Nude mice.

SKNV3.3 parent cell line and two examples of OBCAM-transfected re-expressing SKNV3.3 cell lines were injected intra-peritoneally (i.p.) into Nude mice: 3 injections per cell line with one injection per mouse. After 65 days, the mice were sacrificed and the tumours from the peritoneal cavity removed and photographed. The total amount of tumour present in the i.p. cavity is markedly diminished in mice injected with OBCAM transfected SKNV3.3 cells compared with the parent SKNV3.3 cells. This Figure show total tumour removed from three SKNV3.3 injected mice and from five mice injected with OBCAM-transfected SKNV3.3 cells: three from one OBCAM-transfected cell line and two from the second OBCAM-transfected cell line. No tumour was discernible in the third mouse injected with the second OBCAM-transfected SKNV3.3 cell line. The intra-peritoneal spread of tumours expressing OBCAM following OBCAM transfection is also greatly reduced compared to parent SKNV3.3 cells (not shown).

EXAMPLE 1

The Role of OBCAM and NTM in the Progression of Epithelial Ovarian Cancer (EOC)

11q24-q25 LOH Analysis of Ovarian Blood/Tumour Paired DNAs

Fluorescently labelled polymorphic microsatellite markers selected from the chromosome 11q24-q25 region were PCR amplified from DNAs extracted from whole ovarian tumours and also from either blood or from normal ovarian tissue as a matched normal control. Markers used, in order from centromere to 11qter, were: 11cen-D11S910-D11S1320-D11S874-D11S4085-D11S969-11qter. PCR amplified products were separated on an ABI 310 Genetic Analyzer using GeneScan software (PE Biosystems). LOH is defined as imbalance of 30% or greater difference between alleles in the tumour compared with normal tissues. The striking feature of LOH observed at D11S4085 is the completeness of LOH. This is unusual when one considers that the ovarian tumour DNA was extracted from whole tumour rather than from microdissected tissue. Tumour tissue would normally be regarded to contain a proportion of contaminating normal cells, e.g. stromal cells. However, as the loss is so complete in this case, we may infer from the lack of contaminating normal tissue that loss of the D11S4085 allele is an extremely early event in the process of ovarian carcinogenesis.

Physical Mapping of the OBCAM/NTM Region

OBCAM and Neurotrimin are the 11q24-q25 LOH-Associated Genes: Having identified regions of LOH, we next wanted to identify the genes from that region disrupted by LOH in ovarian cancer. In order to identify BAC clones from the 11q24-q25 region containing the markers used in the LOH study, their corresponding nucleotide sequences were used to BLAST search the Genbank HTGS database at NCBI. Of the markers used, all except D11S969 identified BAC clones in the homology search of the HTGS database. Nucleotide sequences from the corresponding BAC clones were then analysed using the Nucleotide Identify X (NIX) algorithm at the UK Human Genome Mapping Project Resource Centre (HGMP-RC). NIX allows multiple bioinformatics programs to be performed simultaneously on a nucleotide sequence, such as BLAST searches against multiple databases, identifying nucleotide and protein translation homologies, performing exon predictions, CpG island predictions etc. NIX has allowed us to compile a contig map of the region incorporating overlapping BAC clones, identifying the genes in the region and their positions relative to the markers in the study (FIG. 1).

NIX has identified that the two highly related genes OBCAM and Neurotrimin are the only genes present within the region of LOH. The marker of highest LOH, D11S4085, is contained within OBCAM, whereas Neurotrimin spans two of the markers: D11S1320 and D11S874. OBCAM and NTM are highly related, sharing 80% and 76% nucleotide and protein identity, respectively. In the mouse, their respective homologues are located near each other on a region of chromosome 9 syntenic with human chromosome 11q24-q25. It is likely, therefore, that the two genes have arisen as a consequence of a gene duplication event prior to the divergence of man and mouse. In man, the two genes are arranged in a 3'-3' orientation, with convergent transcriptional directions (FIG. 1).

OBCAM and NTM are Expressed in Normal Ovarian Surface Epithelium (OSE) but not in Ovarian Cancer Cell Lines We extracted RNA from cultured normal human OSE (HOSE), primary peroperatively stripped HOSE, and from total whole normal ovary. RT-PCR showed that both OBCAM and NTM are expressed in primary peroperatively stripped epithelium, whereas only NTM and not OBCAM expression is detectable in cultured HOSE. Expression of both was detectable from whole ovary, despite the OSE comprising only a minor component of the total organ.

In contrast, expression of neither gene was evident to any substantial degree in a panel of RNAs isolated from ovarian, breast, lung, colon and pancreatic cancer cell lines. By Northern blotting, expression was completely undetectable in all cell lines with two exceptions: CaOv3 (ovarian) and WX330 (small cell lung cancer), in which NTM expression was readily detectable. Interestingly, the size of NTM transcript in CaOv3 is smaller than that expected for full length NTM. RT-PCR analysis has indicated that the transcript is shorter than expected due to a 5' truncated mRNA, the precise extent of which is undetermined, and possibly arises as a result of 5' mutation coupled with the use of an intronic alternative promoter.

OBCAM and NTM CpG Islands are Methylated in Cell Lines and Correlates with Lack of Expression The methylation status of both the OBCAM and NTM CpG islands was assessed by MS PCR with primer pairs to detect methylated and unmethylated alleles in a range of cancer cell lines of ovarian, breast, lung, colon and prostate origin. The results are presented in Tables 1 and 2. We assayed the same range of cell lines for the level of OBCAM and NTM expression by RT-PCR and compared the results with the methylation status determined in the MS PCR assay. A correlation between methylation of the respective CpG islands and the lack of detectable expression was found; conversely, lack of methylation correlates with gene expression. An exception to this correlation is the ovarian cancer cell line OAW28, which despite no apparent methylation, shows no expression of either gene. This may be attributable to methylation not detectable by this particular assay: it lies either outwith the region being amplified or alternatively between the MS PCR primers since MSP only detects the presence/absence of methylation at the primer binding site itself.

TABLE 1

NTM methylation status in cancer cell lines as determined by MS-PCR analysis.

| | |
|---|---|
| PE016 | FM |
| PEA1 | FM |
| PEA2 | FM |
| OVCAR 4 | FM |
| OVCAR 5 | FM |
| OAW 42 | FM |
| A2780 | FM |
| SK-OV-3 | FM |
| OVCAR 3 | HM |
| PE01 | HM |
| PEO1 CDDP | HM |
| PE04 | HM |
| PE06 | HM |
| PE014 | HM |
| PE023 | HM |
| OAW 28 | U |
| 59 M | U |
| CaOV3 | U |
| MDA.MB.231 | FM |
| ZR75.1 | FM |
| MCF7 | FM |
| T47D | HM |
| LoVo | FM |
| HT-29 | FM |
| HRT-18 | FM |
| HCT-15 | FM |
| SW48 | FM |
| DU145 | FM |
| PC-3 | FM |
| LNCaP | HM |
| PANC1 | FM |
| HELA | FM |
| K562 | HM |
| FATO | U |
| WX330 | U |
| HL60 | U |

FM = fully methylated
HM = hemimethylated
U = unmethylated

TABLE 2

OBCAM methylation status in cancer cell lines as determined by MS-PCR analysis.

| | |
|---|---|
| PE01 | FM/HM |
| PEO1 CDDP | FM |
| PE016 | FM |
| OVCAR 3 | FM |
| OVCAR 4 | FM |
| OVCAR 5 | FM |
| OAW 42 | FM |
| A2780 | FM |
| PEA1 | — |
| PEA2 | FM |
| PE04 | FM |
| PE06 | FM |
| PE014 | — |
| OAW 28 | U |
| 59 M | U |
| CaOV3 | U |
| MCF7 | FM |
| ZR75.1 | FM/HM |
| T47D | HM |
| HT-29 | FM |
| HRT-18 | FM |
| HCT-15 | FM |
| SW48 | FM |
| DU145 | FM |
| PC-3 | FM/HM |
| LNCaP | HM |
| HELA | FM |
| K562 | HM |
| PANC1 | HM |
| FATO | U |
| WX330 | U |
| HL60 | U |

FM = fully methylated
HM = hemimethylated
FM/HM = fully or hemi-methylated
U = unmethylated
— = not determined OBCAM and NTM are Methylated in Primary Ovarian Tumours We performed MS PCR to detect methylated and unmethylated alleles for OBCAM and NTM in 13 ovarian tumour/normal (or blood) matched pairs of DNAs. A representative set of MSP assays on 13 blood/tumour pairs including a methylated DNA (Intergen) and unmethylated DNA (HL60 cell line) control samples is shown in FIG. 3, and a summary of results is presented in FIG. 6. We observed that NTM frequently accompanies OBCAM methylation and the two may be considered to be concordant. This is in agreement with the lack of survival association with LOH at OBCAM (D11S4085), which indicates that OBCAM inactivation is an early event in this process.

Materials and Methods

Ovarian Cancer Matched Blood (Normal)/Tumour Paired Samples

DNA from 65 matched blood (or paraffin embedded normal ovarian tissue) and paraffin-embedded ovarian tumour samples was extracted using QIAamp DNA minikit as per the manufacturer's protocol (QIAGEN)

Loss of Heterozygosity Analysis

PCR products from 6 fluorescently tagged polymorphic microsatellite markers from the 11q24-q25 region were amplified from the panel of matched ovarian normal/tumour DNAs: cen-D11S910-2-D11S1320-D11S874-D11S4085-D11S969-11qter PCR products were separated and analysed on an ABI 310 Genetic Analyzer using Genescan software (PE Biosystems).

Bioinformatics Analysis of the Human Chromosome 11q24-q25 Region:

BAC clones containing the six polymorphic 11q24-q25 markers used to detect LOH were identified from the High Throughput Genomic Sequences (HTGS) database in GenBank by BLAST searching with marker sequences. The sequences from identified BAC clones were then analysed using the Nucleotide Identify X (NIX) algorithm (Human Genome Mapping Project Resource Centre, Hinxton, UK). In this way, a BAC contig map of the region was assembled detailing positions of known genes relative to microsatellite markers.

Reverse Transcriptase PCR(RT-PCR)

Total RNA extraction from cell lines was performed using TRI Reagent (Sigma, Dorset, UK). $1^{st}$ strand cDNA was prepared from 1 µg DNaseI-treated using a $1^{st}$ strand cDNA synthesis kit (Roche, UK), and 2 µl aliquots then used as template in 25 µl PCR reactions. Alternatively, for smaller cell numbers, DNaseI-treated total RNA was prepared using Absolutely RNA mini prep spin columns (Stratagene) and $1^{st}$ strand cDNA prepared as described.

Tissue Expression

Multiple Tissue Northern (MTN) blots (Human I and Human II) and Multiple Tissue cDNA panels (Human I and Human II) were purchased from BD Clontech, Basingstoke, UK. MTNs were hybridized with full length OBCAM and NTM PCR amplified cDNA probes, using ExpressHyb buffer (BD Clontech) as recommended. Blots were rehybridized with a β-Actin control probe (BD Clontech). MTC panels were screened by PCR with OBCAM and NTM primer pairs designed to amplify full-length cDNA products.

Methylation Specific PCR (MS PCR)

Genomic DNAs isolated from the normal/ovarian tumour matched pairs (above) and cell line panels (ovarian, breast, lung, colon and pancreatic cancer) were modified by bisulphite treatment using the CpG Modification kit (Intergen) as per the recommended protocol. Control methylated DNA was purchased from Intergen. The bisulphite-modified DNA was PCR amplified with primer pairs specifically recognising the methylated and unmethylated alleles, respectively, of the human NTM and OBCAM CpG islands. Primer pairs and amplification conditions were as follows.

In order to determine the extent of CpG island methylation in the OBCAM and NTM CpG islands, methylation specific PCR amplified bisulphite-treated DNA was subcloned into the pGEM-T Easy TA cloning vector (Promega). Six subclones corresponding to each PCR product were sequenced using Big Dye (PE BioSystems) chemistry following standard methods.

Azacytidine and TSA Re-Expression

In demethylation re-expression experiments, $5\times10^6$ cells (MDAMB23.1 for OBCAM; MDAMB23.1 and T47D for neurotrimin) were seeded and left to adhere for 24 hours. Cells were incubated in the presence of 10 µM azacytidine (Sigma) and 0.3 µM TSA added for the final 24 hours of the 4 days. Cells were harvested, RNA isolated, $1^{st}$ strand cDNA synthesised and RT-PCR reactions performed with OBCAM, NTM and actin PCR primers Transfection of OBCAM into SKOV-3

The full coding sequence of human OBCAM plus Kozak consensus sequence and 3'UTR overlap was PCR amplified from normal human ovarian surface epithelium RNA and subcloned into the pGEM-T Easy TA cloning vector (Promega). The PCR primer pair used for the amplification were:

OPCML F1: 5'-AGTTGTGGCTGTCGAGAATG-3' nucs 34-53 (SEQ ID NO.:71)

OPCML R1: 5'-TCAGAGGACCTAGGATTTCT-3' nucs 1110-1091 (SEQ ID No.:70)

Nucleotide numbering from Genbank accession NM_002545 mRNA (NM_002454.2 Reference Sequence). The OBCAM insert was then excised with NotI and resubcloned into NotI-digested pcDNA3.1 Zeo mammalian expression vector (Invitrogen). The insert sequence was then verified prior to use in transfection. Plasmid DNAs corresponding to OBCAM sense and antisense constructs and parental vector were prepared by standard methods (QIAGEN) and digested with PvuI. 1 µg and 0.2 µg of PvuI-linearised constructs and vector were transfected into the clonal SKOV-3 neomycin resistant cell line SKNV3.3 in the presence of lipofectin.

Selection on Zeomycin (Invitrogen)

48 hours following transfection, cells were split 1:6 and cultured in the presence of Zeomycin antibiotic selection. Individual colonies were then selected for analysis 3 weeks following imposing antibiotic selection.

Transfections indicate that OBCAM antisense and vector control transfectants grow more rapidly than OBCAM sense transfectants suggesting that there is a functionally suppressive effect on growth.

Discussion

We have performed a more refined LOH analysis in EOC of the 11q24-q25 region in 65 paired normal/tumour samples and identified a high rate 56% of LOH within the OBCAM gene at marker D11S4085. In addition, LOH of 40% within the homologous gene, neurotrimin (NTM or NTM), at markers D11S1320 and D11S874, was also detected. Analysis of clinicopathological parameters shows no association of LOH with adverse patient survival, indicating that loss of these genes is an early event in ovarian carcinogenesis. It also proves that neither is the survival gene detected in our previous LOH studies. Methylation specific PCR of DNA isolated from 43 matched normal/ovarian tumour pairs and 6 tumour-only DNAs has identified rates of CpG island methylation of 76% for both OBCAM and NTM, with 86% concordance between genes. Bisulphite sequencing confirmed the presence of extensive methylation within the CpG islands from both genes. Of 12 EOC lines, OBCAM was fully methylated in 75% of cell lines, 0% were partially methylated and 25% were unmethylated. For HNT/NTM, in 13 EOC lines, 54% were fully methylated, 23% partially methylated, 23% unmethylated. Re-expression of both genes was accomplished by azacytidine treatment with Trichostatin A (TSA), providing conclusive evidence that CpG island methylation is the mechanism underlying the lack of expression of these genes. It is apparent from the MS-PCR studies that methylation of the OBCAM CpG island is found with that of NTM, and may be a prerequisite for NTM methylation to occur. This combined with the LOH data suggests that of the two genes, OBCAM is the more important in the early events of the disease. Consequently, we have transfected OBCAM into a clonal derivative of the ovarian cancer cell line SKOV-3, under the control of the CMV promoter, and show the following effects. Three observations suggest NTM/OBCAM function as suppressors. Firstly there is evidence that some sense NTM transfected SKOV3 clones demonstrate suppression of tumorigenicity as compared with antisense clones, but clonal heterogeneity of SKOV3 made this data difficult to interpret. Furthermore, there was some evidence that morphologically there was contact inhibition associated with sense NTM transfected SKOV3 clones. Finally, we have noticed that antisense OBCAM and vector control transfected clonal derivative of SKOV3 (SKNV3.3) demonstrates faster growth compared with sense OBCAM transfected into the same SKOV3 clonal line. There is an apparent 50% reduction in growth rates of the OBCAM SKOV3 transfected clones as compared with the antisense OBCAM SKOV3 transfected clonal cell lines. By correlating the LOH and methylation studies, we provide evidence for the existence of two inactivating hits in accordance with Knudsen's classical 2-hit mechanism of tumour suppressor gene inactivation (Knudsen AG, 1971 Proc Natl Acad Sci 68(4) p 820-823). It also highlighted tumour samples in which only one inactivating mechanism (either LOH or methylation) was present, allowing us to target these samples for detection of mutations in the OBCAM gene.

This is the first description of the involvement of the IgLON family, and in particular of OBCAM and Neurotrimin, in the development of any form of cancer, or indeed, in any form of human disease.

EXAMPLE 2

SKNV3.3 is Methylated for OBCAM and does not Express OBCAM

The cell line SKNV3.3 is a neomycin resistant clonal derivative of the ovarian cancer cell lineSKOV3. We have shown by quantitative RT-PCR that it does not express OBCAM and by MS-PCR that OBCAM CpG island is methylated. Furthermore, demethylation following in vitro exposure of SKVN3.3 to 5'-aza-2'-deoxycytidine results in re-expression of OBCAM. It was therefore selected for OBCAM functional studies.

The OBCAM CpG island is fully methylated as determined in the MS-PCR assay. Consequently, OBCAM expression in SKNV3.3 is repressed by this epigenetic mechanism. In order to prove that CpG island methylation is the mechanism of repression of OBCAM expression, SKNV3.3 cells were exposed to the 5-aza-2'-deoxycytidine and assayed for OBCAM re-expression by RT-PCR, Southern blotting and hybridisation with an OBCAM specific probe.

$1 \times 10^5$ SKNV3.3 (Passage 6) cells were seeded into 25 cm$^3$ tissue culture flask in 10 ml media. The media was replaced after 24 hours and 5'-aza 2'-deoxycytidine (Sigma A3656) added to give a final concentration of 20 µM. A duplicate flask of cells received no azacytidine exposure (control). After 4 days the cells from both flasks were harvested and DNaseI-treated total RNA prepared using the Absolutely RNA Miniprep kit (Stratagene). First strand cDNA was synthesised using the $1^{st}$ Strand cDNA Syntheis Kit (Roche) and 2 µl aliquots cDNA used per RT-PCR reaction.

Actin RT-PCR was performed to confirm the integrity of the $1^{st}$ strand cDNA from control and azacytidine-treated SKVN3.3 cells. Equal aliquots of each Actin PCR reaction separated on an agarose gel confirmed the integrity of both samples and the equal concentration of cDNA per sample.

OBCAM RT-PCR Reaction:

OPCML F4/R6 RT-PCR (474 bp product) performed in a 25 µl reaction.

PCR primers used are (nucleotide numberings correspond to GenBank Accession No. NM_002545)

OPCML F4: 5'-TACCATAGATGACCGGGTAA-3' nucs: 221-240 (SEQ ID NO.:73)

OPCML R6: 5'-TTCCGCACATCGGGCGCAGC-3' nucs: 694-675 (SEQ ID NO.:74)

Products from the OBCAM PCR reactions were size separated on a 2% agarose gel, Southern blotted overnight onto MSI nylon membrane, and the DNA then UV crosslinked to the membrane.

OBCAM Exon2 F2/OPCML R6 PCR product, purified through a QIAquick PCR purification column (QIAGEN), was labelled with $\alpha^{32}$P-dCTP.PCR PCR primers were as follows (nucleotide numberings correspond to GenBank Accession No. NM_002545):

OBCAM Exon 2 F2: 5'-ATAGACCCTCGTGTGATCAT-3' nucs 300-319 (SEQ ID NO.:81)

OPCML R6: 5'-TTCCGCACATCGGGCGCAGC-3' nucs: 694-675 (SEQ ID NO.:74)

Following overnight hybridisation, the blot was washed to remove unbound probe, and the blot exposed to X-ray film for 1 hour at −70° C. and then developed.

Re-expression of OBCAM is clearly evident in SKNV3.3 cells exposed to 20 μM 5'-aza 2'-deoxycytidine for 4 days. In contrast, no OBCAM expression is detectable in control SKNV3.3 cells after 4 days with no 5'-aza 2'-deoxycytidine treatment (FIG. 13). Actin PCR product was amplified to equal intensity from both control and treated cells, confirming the integrity of the isolated RNA and synthesised $1^{st}$ strand cDNA.

EXAMPLE 3

Functional Studies of OBCAM in SKVN3.3 (SKOV3 Clonal Derivative)

OBCAM Transfection into SKNV3.3

The full coding sequence of human OBCAM plus Kozak consensus sequence and 3'UTR overlap was PCR amplified from normal human ovarian surface epithelium RNA and subcloned into the pGEM-T Easy TA cloning vector. The PCR primer pair used to amplify nucleotides 34-1110 (NM_002454.2 Reference Sequence) was:

OPCML F1: 5'-AGTTGTGGCTGTCGAGAATG-3' nucs 34-53 (SEQ ID NO.:69)

OPCML R1: 5'-TCAGAGGACCTAGGATTTCT-3' nucs 1110-1091 (SEQ ID NO.:70)

amplifying a 1077 bp PCR product. The OBCAM insert was then excised with NotI and resubcloned into NotI-digested pcDNA3.1 Zeo (zeomycin-resistant) mammalian expression vector (Invitrogen) in both the sense and antisense orientations. The insert sequence was then verified prior to use in transfection. Plasmid DNAs corresponding to OBCAM sense and antisense constructs and parental vector were prepared by standard methods (QIAGEN) and digested with PvuI.

1 μg and 2 μg PvuI-linearised constructs and vector were transfected into the neomycin-tagged SKOV-3 clonal derivative cell line, SKNV3.3.

Cell lines were maintained in RPMI 1640 with heat inactivated 10% Fetal Calf Serum (FCS) and penicillin (100 units/ml) streptomycin (100 μg/ml) and G418 and Zeocin (Invitrogen) as appropriate.

$2 \times 10^5$ SKNV3.3 cells were seeded per 60 mm dish in 4 ml of media. 24 hours later when 50% confluent, the cells were transfected separately with 2 μg of linearised constructs: OBCAM sense or antisense pcDNA3.1 zeo constructs, or pcDNA3.1 zeo vector containing no insert, using LIPOFECTIN Reagent (Life Technologies GIBCO BRL) according to the manufacturers protocol. Forty-eight hours after transfection, each plate of cells was split one in six and transfected cells were then selected with 250 μg/ml zeocin. At three weeks colonies were picked into 24 well plates and clonal cell lines established.

OBCAM Suppresses Growth In Vitro:

Transfection of OBCAM into SKNV3.3 cells results in suppressed growth compared with SKNV3.3 control cells in vitro (figure not shown).

OBCAM Suppresses Tumour Growth and Spread In Vivo:

Log phase SKNV3.3 control and OBCAM transfected cells were harvested and $5 \times 10^6$ cells injected either intraperitoneally (i.p.) or subcutaneously (s.c.) into the flanks of nude mice, with 6 s.c. and 3 i.p. injections per cell line. Size measurements of s.c. tumours were taken weekly for 4 weeks. Mice that received cells via i.p. injection were sacrificed 65 days post injection and tumours removed from the peritoneal cavity, weighed and photographed.

Transfection of OBCAM into SKNV3.3 results in markedly suppressed sub-cutaneous tumour growth (FIG. 14) comparing SKNV3.3 cells transfected with the OBCAM 'sense' expression construct (Sense transfectants) and control SKNV3.3 cells (Controls).

Transfection of OBCAM into SKNV3.3 almost completely abolished tumour growth and intra-peritoneal spread, comparison with the tumour growth and i.p. spread observed with SKNV3.3 parental cells (FIG. 21; see Example 8).

OBCAM Transfection Enhances Cell Aggregation:

Log phase SKNV3.3 control and OBCAM transfected cells were trypsinised and resuspended in media containing 10% FCS. $1 \times 10^6$ cells were resuspended in 1 ml of media and passed through a 21 gauge needle to ensure creation of a single cell suspension. Cell suspensions were then incubated in 5% $CO_2$ at 37° C. At defined time points, aliquots were removed by a wide bore pipette, and single cells were counted with a haemocytometer.

OBCAM transfection into SKNV3.3 (sense expressing construct) results in enhanced rate of aggregation of cells compared with that observed for control SKNV3.3 cells (FIG. 15). Transfection of the OBCAM anti-sense expressing construct results in a reduced rate of cell aggregation compared with the parent SKNV3.3.

EXAMPLE 4

Exon Structure of the Human OBCAM Gene

The exon structure of the human OBCAM gene was determined in a bioinformatic analysis. The Human OBCAM mRNA reference sequence NM_002545.2 was compared with available Human Genome Project sequence in the GenBank HTGS database using a BLAST2 homology search. The comparison identified that OBCAM consists of at least 7 exons. The derived exon structure with the location of intron-exon boundaries are shown in FIG. 16. The exonic sequence is highlighted in yellow and intron sequence flanking the exons is in plain text. Nucleotide numberings relate to the corresponding to the GenBank database sequence (accession numbers for which are given). The nucleotide sequence for Exon 1 is incomplete in the area encompassing the exon/ intron 1 boundary due to lack of available Human Genome Project Sequence in GenBank Accession AC027631.4.

EXAMPLE 5

OBCAM Mutation Detection by Single Strand Conformation Polymorphism Electrophoresis (SSCPE)

Following bioinformatic analysis prediction of the structure of the human OBCAM gene primers to amplify the 7 identified exons of the OBCAM gene were designed. Exon 2 was analysed with two overlapping primer sets due to size limitation of PCR product useful for SSCPE analysis. DNA samples used in SSCPE analysis were extracted from ovarian tumour and matched normal tissue paraffin-embedded archival ovarian tumours, and ovarian cancer cell lines.

OBCAM exon specific primers used were as follows. PCR product sizes are given in parentheses.

In FIG. 16, the locations of sense and antisense primers for SSCPE are highlighted in single and double underlining, respectively. Intronic and exonic sequences are non- and bold-highlighted, respectively.

Exon 1 (188 bp)

OBCAM EX1 F3: 5'-GACCAGGACTGTGCGGCTGC-3' nucs 54514-54533 AC027631.4 (SEQ ID NO.:82)

OPCML R3: 5'-CGTCACGTTGTCCATAGCTT-3' nucs: 188-169 NM_002545.2 (SEQ ID NO.:83)

Exon 2/1 (175 bp): (Nucleotide Numbering from GenBank AC012234.6)

OBCAM EX2 F1: 5'-CACCACTCCCTGCCTCACTG-3' nucs 75226-75245 (SEQ ID NO.:84)

OBCAM EX2 R1: 5'-CATCCACATTTTGGATCATG-3' nucs 75400-75381 (SEQ ID NO.:85)

Exon 2/2 (180 bp): (Nucleotide Numbering from GenBank AC012234.6)

OBCAM EX2 F2: 5'-ATAGACCCTCGTGTGATCAT-3 nucs 75331-75350 (SEQ ID NO.:86)

OBCAM EX2 R2: 5'-TGGCAACCCCAGATCCAGCT-3' nucs 75510-75491 (SEQ ID NO.:87)

Exon 3 (179 bp): (Nucleotide Numbering from GenBank AP000843.3)

OBCAM EX3 F1: 5'-CAGGTATTTCTTCTATCCTG-3' nucs 37032-37051 (SEQ ID NO.:88)

OBCAM EX3 R1: 5'-GTCCTCCAGGTCAGCACCTT-3' nucs 37210-37191 (SEQ ID NO.:89)

Exon 4 (214 bp): (Nucleotide Numbering from GenBank AP000843.3)

OBCAM EX4 F1: 5'-TGGTTACACAGTTTCCTGAT-3' nucs 2881-2900 (SEQ ID NO.:90)

OBCAM EX4 R1: 5'-AGAACCCCCTGGCTGCAGGT-3' nucs 3094-3075 (SEQ ID NO.:91)

Exon 5 (195 bp): (Nucleotide Numbering from GenBank AP000843.3)

OBCAM EX5 F1: 5'-GTGCGTGCATGCCTGTGCAT-3' nucs 3466-3485 (SEQ ID NO.:92)

OBCAM EX5 R1: 5'-CAGAACTGTCCAGGTGTCAT-3' nucs 3660-3641 (SEQ ID NO.:93)

Exon 6 (198 bp): (Nucleotide Numbering from GenBank AP000843.3)

OBCAM EX6 F1: 5'-TAGCAATGTCTTCCCTCTTG-3' nucs 4028-4047 (SEQ ID NO.:94)

OBCAM EX6 R1: 5'-GCATCCAGGCTTCCAGCACT-3' nucs 4225-4206 (SEQ ID NO.:95)

Exon 7 (176 bp): (Nucleotide Numbering from GenBank AP000843.3)

OBCAM EX7 F1: 5'-TCCTTGGGTGTATGCTAATG-3' nucs 19945-19964 (SEQ ID NO.:96)

OBCAM EX7 R1: 5'-GCGTTGCTCAGAGGACCTAG-3' nucs 20120-20101 (SEQ ID NO.:97)

SSCPE for each OBCAM exon has been performed on ovarian cancer matched normal/tumour DNAs, tumour DNAs and cell lines. In keeping with the high rate of LOH and CpG island methylation observed for OBCAM, the expected frequency of somatic mutation is low. A somatic mis-sense mutation which has been detected by SSCPE and sequencing is described below.

Somatic OBCAM Mutation in the PEO Ovarian Cancer Cell Line Series

SSCPE of OBCAM Exon2 F1/R1 PCR products identified a 'band shift' in DNA from a series of cell lines derived from an ovarian cancer patient during the course of her disease. PEO1 represents a platinum sensitive ovarian cancer cell line derived from the patient early in the course of her disease. The platinum resistant cell line PEO4 was derived from the same patient upon relapse after cisplatin chemotherapy. The cell line PEO1CDDP was derived from PEO1 by in-vitro cisplatin exposure and represents an in-vitro model of platinum resistance. Fibroblast DNA, representing normal DNA, was isolated from the patient at the same the PEO4 cell line was established (PEO4 Fibroblasts).

The Exon2 F1/R1 PCR products amplified from PEO1, PEO1CDDP, PEO4 and PEO4 Fibroblasts were sequenced with the same primers as used in the original PCR. Sequence trace files (FIG. 17) clearly indicate a heterozygous peak corresponding to the presence of both a C and a G nucleotide at position 334 (GenBank Accession No NM_002545, shown in FIG. 7) in PCR products from PEO1, PEO1CDDP, and PEO4. Position 334 (NM_002545) is homozygous for a C in the PCR product from PEO4 Fibroblast (marked by *). The wild type sequence (NM_002545 reference nucleotide sequence) contains a C residue at this position, altering a CCA codon to CGA. Translation (using ExPasy) of the nucleotide sequence encompassing this position predicts that the corresponding wild type amino acid proline (P) is altered to an arginine (R), corresponding to amino acid residue 95 of the immature OBCAM protein sequence (FIG. 18). This residue is believed to be located in the first immunoglobulin domain of OBCAM (FIG. 7 and GenBank Accession No NP_002536).

PEO4 Fibroblasts are homozygous wild type (proline) whereas PEO1, PEO1CDDP, and PEO4 are heterozygous wild type/mis-sense mutant (proline/arginine). Substitution of an arginine residue for a proline at this position may result in an altered OBCAM structural confirmation, and therefore altered OBCAM function.

As all the cell lines derived during the time course of this patient's disease contain this mis-sense mutation, we can surmise that the mutation was an early event in the course of their disease. As PEO4 Fibroblasts, corresponding to normal DNA, are wild type, this alteration is a somatic event.

This is the first somatic mutation identified for OBCAM in cancer, including ovarian cancer.

EXAMPLE 6

OBCAM is Unmethylated in Normal Human Ovary

We have extracted DNA and RNA from 5 normal human ovary specimens. OBCAM MS-PCR of these specimens shows that the OBCAM CpG island is unmethylated. The 600 bp amplified MS-PCR product contains 58 CpGs. Sequencing across the OBCAM MS-PCR product from these normal ovaries showed no evidence of methylated CpGs within the product.

In contrast, sequencing the MS-PCR product from ovarian cancer cell lines and primary tumours that are methylated in the MS-PCR assay, show extensive methylation across the region of CpG island amplified.

EXAMPLE 7

OBCAM CpG Island is Methylated in Ovarian Tumours and Unmethylated in Normal Ovary DNA from two examples of ovarian tumours and from two examples of normal ovaries were chemically modified by bisulphite treatment. Methylation specific PCR was then performed with primers designed to discriminate Methylated (M) and Unmethylated (U) OBCAM CpG island bisulphite modified DNA. A 529 bp methylated or unmethylated specific PCR product was amplified specifically from the ovarian tumour or normal ovary DNAs, respectively, using the primers detailed above (OBCAM CpG Island Sequencing). The PCR product amplified corresponds to nucleotides 25-553 of FIG. 19 (OBCAM CpG Island Bisulphite Sequencing). PCR products were then subcloned into pGEM-T Easy and individual subclones, representing individual alleles, were then sequenced and the presence or absence of methylated C nucleotides at CpGs scored. FIG. 20 represents the extent of methylated CpG Cs present in the examples of ovarian tumours and of normal ovaries. The nucleotide numbering is the location of CpG Cs as shown in FIG. 19, and the CpG number is the sequential numbering of the CpGs located within the 526 bp of the OBCAM CpG island sequenced. The results of sequencing of six alleles are shown for each of the two examples of ovarian tumour and two alleles for each of the examples of normal ovary. The black filled square represents a methylated CpG, the empty square represents an unmethylated CpG, and the square containing vertical lines represents cases where the methylation status of the CpG was not determined. FIG. 20 shows that the CpG island to be extensively methylated in ovarian tumours and unmethylated in normal ovary.

The invention claimed is:

1. A method of screening for ovarian cancer in a human patient comprising the steps of
   (i) obtaining an ovarian tissue sample containing the OBCAM gene from the patient;
   (ii) determining the degree of methylation in the CpG island of the OBCAM gene in the sample; and
   (iii) comparing the level of methylation of the CpG island of the OBCAM gene in the sample with the level of methylation in a control sample containing non-tumour ovarian cells, wherein a higher degree of methylation in the sample compared to the control sample indicates an increased likelihood of ovarian cancer.

2. A method according to claim 1 wherein the cancer exhibits methylation of the OBCAM gene.

* * * * *

SEQUENCE LISTING

```
<160> NUMBER OF SEQ ID NOS: 124

<210> SEQ ID NO 1
<211> LENGTH: 24
<212> TYPE: DNA
<213> ORGANISM: Homo sapiens

<400> SEQUENCE: 1
catcgcgctg caatcggctc cccg                                              24

<210> SEQ ID NO 2
<211> LENGTH: 25
<212> TYPE: DNA
<213> ORGANISM: Homo sapiens

<400> SEQUENCE: 2
aggcgtccag tggaggggca cgggc                                             25

<210> SEQ ID NO 3
<211> LENGTH: 25
<212> TYPE: DNA
<213> ORGANISM: Homo sapiens

<400> SEQUENCE: 3
aggcgtttag tggaggggta cgggc                                             25

<210> SEQ ID NO 4
<211> LENGTH: 24
<212> TYPE: DNA
<213> ORGANISM: Homo sapiens
```

```
<400> SEQUENCE: 4
catcgcgcta caatcgactc cccg                                          24

<210> SEQ ID NO 5
<211> LENGTH: 25
<212> TYPE: DNA
<213> ORGANISM: Homo sapiens

<400> SEQUENCE: 5
aggtgtttag tggaggggta tgggt                                         25

<210> SEQ ID NO 6
<211> LENGTH: 24
<212> TYPE: DNA
<213> ORGANISM: Homo sapiens

<400> SEQUENCE: 6
catcacacta caatcaactc ccca                                          24

<210> SEQ ID NO 7
<211> LENGTH: 22
<212> TYPE: DNA
<213> ORGANISM: Homo sapiens

<400> SEQUENCE: 7
cagcgcgatg gacacgcaca cc                                            22

<210> SEQ ID NO 8
<211> LENGTH: 21
<212> TYPE: DNA
<213> ORGANISM: Homo sapiens

<400> SEQUENCE: 8
aacgcggcgc ccctcgcagc g                                             21

<210> SEQ ID NO 9
<211> LENGTH: 22
<212> TYPE: DNA
<213> ORGANISM: Homo sapiens

<400> SEQUENCE: 9
tagcgcgatg gatacgtata tc                                            22

<210> SEQ ID NO 10
<211> LENGTH: 21
<212> TYPE: DNA
<213> ORGANISM: Homo sapiens

<400> SEQUENCE: 10
aacgcgacgc ccctcgcaac g                                             21

<210> SEQ ID NO 11
<211> LENGTH: 22
<212> TYPE: DNA
<213> ORGANISM: Homo sapiens

<400> SEQUENCE: 11
tagtgtgatg gatatgtata tt                                            22

<210> SEQ ID NO 12
<211> LENGTH: 21
<212> TYPE: DNA
<213> ORGANISM: Homo sapiens
```

-continued

```
<400> SEQUENCE: 12
aacacaacac ccctcacaac a                                        21

<210> SEQ ID NO 13
<211> LENGTH: 22
<212> TYPE: DNA
<213> ORGANISM: Homo sapiens

<400> SEQUENCE: 13
caacttctgc gctggcatcg gc                                       22

<210> SEQ ID NO 14
<211> LENGTH: 21
<212> TYPE: DNA
<213> ORGANISM: Homo sapiens

<400> SEQUENCE: 14
aacgcggcgc ccctcgcagc g                                        21

<210> SEQ ID NO 15
<211> LENGTH: 22
<212> TYPE: DNA
<213> ORGANISM: Homo sapiens

<400> SEQUENCE: 15 taattttgc gttggtatcg gc                                        22

<210> SEQ ID NO 16
<211> LENGTH: 21
<212> TYPE: DNA
<213> ORGANISM: Homo sapiens

<400> SEQUENCE: 16
aacgcgacgc ccctcgcaac g                                        21

<210> SEQ ID NO 17
<211> LENGTH: 22
<212> TYPE: DNA
<213> ORGANISM: Homo sapiens

<400> SEQUENCE: 17
taatttttgt gttggtattg gt                                       22

<210> SEQ ID NO 18
<211> LENGTH: 21
<212> TYPE: DNA
<213> ORGANISM: Homo sapiens

<400> SEQUENCE: 18
aacacaacac ccctcacaac a                                        21

<210> SEQ ID NO 19
<211> LENGTH: 24
<212> TYPE: DNA
<213> ORGANISM: Homo sapiens

<400> SEQUENCE: 19
gcgccgcgtt ctctccgctg gcgc                                     24

<210> SEQ ID NO 20
<211> LENGTH: 25
<212> TYPE: DNA
```

<213> ORGANISM: Homo sapiens

<400> SEQUENCE: 20
tcccggtgcc gcctcggagc gagcg    25

<210> SEQ ID NO 21
<211> LENGTH: 24
<212> TYPE: DNA
<213> ORGANISM: Homo sapiens

<400> SEQUENCE: 21
gcgtcgcgtt ttttcgttg gcgc    24

<210> SEQ ID NO 22
<211> LENGTH: 25
<212> TYPE: DNA
<213> ORGANISM: Homo sapiens

<400> SEQUENCE: 22
tcccgatacc gcctcgaaac gaacg    25

<210> SEQ ID NO 23
<211> LENGTH: 24
<212> TYPE: DNA
<213> ORGANISM: Homo sapiens

<400> SEQUENCE: 23
gtgttgtgtt tttttgttg gtgt    24

<210> SEQ ID NO 24
<211> LENGTH: 25
<212> TYPE: DNA
<213> ORGANISM: Homo sapiens

<400> SEQUENCE: 24
tcccaatacc acctcaaaac aaaca    25

<210> SEQ ID NO 25
<211> LENGTH: 21
<212> TYPE: DNA
<213> ORGANISM: Homo sapiens

<400> SEQUENCE: 25
gcgcggtgcg ggctcatccc c    21

<210> SEQ ID NO 26
<211> LENGTH: 25
<212> TYPE: DNA
<213> ORGANISM: Homo sapiens

<400> SEQUENCE: 26
tcccggtgcc gcctcggagc gagcg    25

<210> SEQ ID NO 27
<211> LENGTH: 21
<212> TYPE: DNA
<213> ORGANISM: Homo sapiens

<400> SEQUENCE: 27
gcgcggtgcg ggtttatttt c    21

<210> SEQ ID NO 28
<211> LENGTH: 25

<212> TYPE: DNA
<213> ORGANISM: Homo sapiens

<400> SEQUENCE: 28
tcccgatacc gcctcgaaac gaacg                                    25

<210> SEQ ID NO 29
<211> LENGTH: 21
<212> TYPE: DNA
<213> ORGANISM: Homo sapiens

<400> SEQUENCE: 29
gtgtggtgtg ggtttatttt t                                        21

<210> SEQ ID NO 30
<211> LENGTH: 25
<212> TYPE: DNA
<213> ORGANISM: Homo sapiens

<400> SEQUENCE: 30
tcccaatacc acctcaaaac aaaca                                    25

<210> SEQ ID NO 31
<211> LENGTH: 22
<212> TYPE: DNA
<213> ORGANISM: Homo sapiens

<400> SEQUENCE: 31
cacagcctgg gcccggcgcg gc                                       22

<210> SEQ ID NO 32
<211> LENGTH: 24
<212> TYPE: DNA
<213> ORGANISM: Homo sapiens

<400> SEQUENCE: 32
tggcagcagc tccatccctg accg                                     24

<210> SEQ ID NO 33
<211> LENGTH: 22
<212> TYPE: DNA
<213> ORGANISM: Homo sapiens

<400> SEQUENCE: 33
tatagtttgg gttcggcgcg gc                                       22

<210> SEQ ID NO 34
<211> LENGTH: 24
<212> TYPE: DNA
<213> ORGANISM: Homo sapiens

<400> SEQUENCE: 34
taacaacaac tccatcccta accg                                     24

<210> SEQ ID NO 35
<211> LENGTH: 22
<212> TYPE: DNA
<213> ORGANISM: Homo sapiens

<400> SEQUENCE: 35
tatagtttgg gtttggtgtg gt                                       22

<210> SEQ ID NO 36

-continued

```
<211> LENGTH: 24
<212> TYPE: DNA
<213> ORGANISM: Homo sapiens

<400> SEQUENCE: 36
taacaacaac tccatcccta acca                                          24

<210> SEQ ID NO 37
<211> LENGTH: 22
<212> TYPE: DNA
<213> ORGANISM: Homo sapiens

<400> SEQUENCE: 37
cacagcctgg gcccggcgcg gc                                            22

<210> SEQ ID NO 38
<211> LENGTH: 23
<212> TYPE: DNA
<213> ORGANISM: Homo sapiens

<400> SEQUENCE: 38
agcgagcggg cgggctggcg gcg                                           23

<210> SEQ ID NO 39
<211> LENGTH: 22
<212> TYPE: DNA
<213> ORGANISM: Homo sapiens

<400> SEQUENCE: 39
tatagtttgg gttcggcgcg gc                                            22

<210> SEQ ID NO 40
<211> LENGTH: 23
<212> TYPE: DNA
<213> ORGANISM: Homo sapiens

<400> SEQUENCE: 40
aacgaacgaa cgaactaacg acg                                           23

<210> SEQ ID NO 41
<211> LENGTH: 22
<212> TYPE: DNA
<213> ORGANISM: Homo sapiens

<400> SEQUENCE: 41
tatagtttgg gtttggtgtg gt                                            22

<210> SEQ ID NO 42
<211> LENGTH: 23
<212> TYPE: DNA
<213> ORGANISM: Homo sapiens

<400> SEQUENCE: 42
aacaaacaaa caaactaaca aca                                           23

<210> SEQ ID NO 43
<211> LENGTH: 23
<212> TYPE: DNA
<213> ORGANISM: Homo sapiens

<400> SEQUENCE: 43
ggccgctgag cttggcgtcc gcg                                           23
```

-continued

```
<210> SEQ ID NO 44
<211> LENGTH: 25
<212> TYPE: DNA
<213> ORGANISM: Homo sapiens

<400> SEQUENCE: 44
tggccgagga gggagaggcc gggcg                                          25

<210> SEQ ID NO 45
<211> LENGTH: 23
<212> TYPE: DNA
<213> ORGANISM: Homo sapiens

<400> SEQUENCE: 45
ggtcgttgag tttggcgttt gcg                                            23

<210> SEQ ID NO 46
<211> LENGTH: 25
<212> TYPE: DNA
<213> ORGANISM: Homo sapiens

<400> SEQUENCE: 46
taaccgaaaa aaaaaaaacc gaacg                                          25

<210> SEQ ID NO 47
<211> LENGTH: 23
<212> TYPE: DNA
<213> ORGANISM: Homo sapiens

<400> SEQUENCE: 47
ggttgttgag tttggtgttt gtg                                            23

<210> SEQ ID NO 48
<211> LENGTH: 25
<212> TYPE: DNA
<213> ORGANISM: Homo sapiens

<400> SEQUENCE: 48
taaccaaaaa aaaaaaaacc aaaca                                          25

<210> SEQ ID NO 49
<211> LENGTH: 28
<212> TYPE: DNA
<213> ORGANISM: Homo sapiens

<400> SEQUENCE: 49
agcgagctac cgagcttggg gccgccgg                                       28

<210> SEQ ID NO 50
<211> LENGTH: 25
<212> TYPE: DNA
<213> ORGANISM: Homo sapiens

<400> SEQUENCE: 50
tggccgagga gggagaggcc gggcg                                          25

<210> SEQ ID NO 51
<211> LENGTH: 27
<212> TYPE: DNA
<213> ORGANISM: Homo sapiens

<400> SEQUENCE: 51
aacgaactac cgaacttaaa accgccg                                        27
```

<210> SEQ ID NO 52
<211> LENGTH: 25
<212> TYPE: DNA
<213> ORGANISM: Homo sapiens

<400> SEQUENCE: 52
taaccgaaaa aaaaaaaacc gaacg                                              25

<210> SEQ ID NO 53
<211> LENGTH: 27
<212> TYPE: DNA
<213> ORGANISM: Homo sapiens

<400> SEQUENCE: 53
aacaaactac caaacttaaa accacca                                            27

<210> SEQ ID NO 54
<211> LENGTH: 25
<212> TYPE: DNA
<213> ORGANISM: Homo sapiens

<400> SEQUENCE: 54
taaccaaaaa aaaaaaaacc aaaca                                              25

<210> SEQ ID NO 55
<211> LENGTH: 20
<212> TYPE: DNA
<213> ORGANISM: Homo sapiens

<400> SEQUENCE: 55
agactcggag gagtctgcgc                                                    20

<210> SEQ ID NO 56
<211> LENGTH: 23
<212> TYPE: DNA
<213> ORGANISM: Homo sapiens

<400> SEQUENCE: 56
acttccccga actccggcag ccg                                                23

<210> SEQ ID NO 57
<211> LENGTH: 20
<212> TYPE: DNA
<213> ORGANISM: Homo sapiens

<400> SEQUENCE: 57
agattcggag gagtttgcgc                                                    20

<210> SEQ ID NO 58
<211> LENGTH: 23
<212> TYPE: DNA
<213> ORGANISM: Homo sapiens

<400> SEQUENCE: 58
acttccccga actccgacaa ccg                                                23

<210> SEQ ID NO 59
<211> LENGTH: 20
<212> TYPE: DNA
<213> ORGANISM: Homo sapiens

<400> SEQUENCE: 59
agatttggag gagtttgtgt                                                    20

<210> SEQ ID NO 60
<211> LENGTH: 23
<212> TYPE: DNA
<213> ORGANISM: Homo sapiens

<400> SEQUENCE: 60
acttccccaa actccaacaa cca                                          23

<210> SEQ ID NO 61
<211> LENGTH: 23
<212> TYPE: DNA
<213> ORGANISM: Homo sapiens

<400> SEQUENCE: 61
tccccgcgcc tcccggtcgc cgc                                          23

<210> SEQ ID NO 62
<211> LENGTH: 23
<212> TYPE: DNA
<213> ORGANISM: Homo sapiens

<400> SEQUENCE: 62
acttccccga actccggcag ccg                                          23

<210> SEQ ID NO 63
<211> LENGTH: 23
<212> TYPE: DNA
<213> ORGANISM: Homo sapiens

<400> SEQUENCE: 63
ttttcgcgtt tttcggtcgt cgc                                          23

<210> SEQ ID NO 64
<211> LENGTH: 23
<212> TYPE: DNA
<213> ORGANISM: Homo sapiens

<400> SEQUENCE: 64
acttccccga actccgacaa ccg                                          23

<210> SEQ ID NO 65
<211> LENGTH: 23
<212> TYPE: DNA
<213> ORGANISM: Homo sapiens

<400> SEQUENCE: 65
tttttgtgtt ttttggttgt tgt                                          23

<210> SEQ ID NO 66
<211> LENGTH: 23
<212> TYPE: DNA
<213> ORGANISM: Homo sapiens

<400> SEQUENCE: 66
acttccccaa actccaacaa cca                                          23

<210> SEQ ID NO 67
<211> LENGTH: 11
<212> TYPE: PRT
<213> ORGANISM: Homo sapiens

<400> SEQUENCE: 67

```
Glu Val Lys Thr Thr Ala Leu Thr Pro Trp Lys
1               5                  10
```

<210> SEQ ID NO 68
<211> LENGTH: 23
<212> TYPE: PRT
<213> ORGANISM: Homo sapiens

<400> SEQUENCE: 68

```
Glu Leu Asn Glu Pro Thr Ser Ser Thr Leu Gln Glu Val Lys Thr
1               5                  10                  15

Thr Ala Leu Thr Pro Trp Lys
            20
```

<210> SEQ ID NO 69
<211> LENGTH: 20
<212> TYPE: DNA
<213> ORGANISM: Homo sapiens

<400> SEQUENCE: 69
agttgtggct gtcgagaatg                                                   20

<210> SEQ ID NO 70
<211> LENGTH: 20
<212> TYPE: DNA
<213> ORGANISM: Homo sapiens

<400> SEQUENCE: 70
tcagaggacc taggatttct                                                   20

<210> SEQ ID NO 71
<211> LENGTH: 20
<212> TYPE: DNA
<213> ORGANISM: Homo sapiens

<400> SEQUENCE: 71
agttgtggct gtcgagaatg                                                   20

<210> SEQ ID NO 72
<211> LENGTH: 20
<212> TYPE: DNA
<213> ORGANISM: Homo sapiens

<400> SEQUENCE: 72
agaggttgca cgatgcagct                                                   20

<210> SEQ ID NO 73
<211> LENGTH: 20
<212> TYPE: DNA
<213> ORGANISM: Homo sapiens

<400> SEQUENCE: 73
taccatagat gaccgggtaa                                                   20

<210> SEQ ID NO 74
<211> LENGTH: 20
<212> TYPE: DNA
<213> ORGANISM: Homo sapiens

<400> SEQUENCE: 74
ttccgcacat cgggcgcagc                                                   20

<210> SEQ ID NO 75

```
<211> LENGTH: 20
<212> TYPE: DNA
<213> ORGANISM: Homo sapiens

<400> SEQUENCE: 75
acatgactat gggaactaca                                              20

<210> SEQ ID NO 76
<211> LENGTH: 20
<212> TYPE: DNA
<213> ORGANISM: Homo sapiens

<400> SEQUENCE: 76
ggaagtggca ctcacatcaa                                              20

<210> SEQ ID NO 77
<211> LENGTH: 25
<212> TYPE: DNA
<213> ORGANISM: Homo sapiens

<400> SEQUENCE: 77
aggcgtttag tggaggggta cgggc                                        25

<210> SEQ ID NO 78
<211> LENGTH: 25
<212> TYPE: DNA
<213> ORGANISM: Homo sapiens

<400> SEQUENCE: 78
tcccgatacc gcctcgaaac gaacg                                        25

<210> SEQ ID NO 79
<211> LENGTH: 25
<212> TYPE: DNA
<213> ORGANISM: Homo sapiens

<400> SEQUENCE: 79
aggtgtttag tggaggggta tgggt                                        25

<210> SEQ ID NO 80
<211> LENGTH: 25
<212> TYPE: DNA
<213> ORGANISM: Homo sapiens

<400> SEQUENCE: 80
tcccaatacc acctcaaaac aaaca                                        25

<210> SEQ ID NO 81
<211> LENGTH: 20
<212> TYPE: DNA
<213> ORGANISM: Homo sapiens

<400> SEQUENCE: 81
atagaccctc gtgtgatcat                                              20

<210> SEQ ID NO 82
<211> LENGTH: 20
<212> TYPE: DNA
<213> ORGANISM: Homo sapiens

<400> SEQUENCE: 82
gaccaggact gtgcggctgc                                              20
```

<210> SEQ ID NO 83
<211> LENGTH: 20
<212> TYPE: DNA
<213> ORGANISM: Homo sapiens

<400> SEQUENCE: 83
cgtcacgttg tccatagctt                                              20

<210> SEQ ID NO 84
<211> LENGTH: 20
<212> TYPE: DNA
<213> ORGANISM: Homo sapiens

<400> SEQUENCE: 84
caccactccc tgcctcactg                                              20

<210> SEQ ID NO 85
<211> LENGTH: 20
<212> TYPE: DNA
<213> ORGANISM: Homo sapiens

<400> SEQUENCE: 85
catccacatt ttggatcatg                                              20

<210> SEQ ID NO 86
<211> LENGTH: 20
<212> TYPE: DNA
<213> ORGANISM: Homo sapiens

<400> SEQUENCE: 86
atagaccctc gtgtgatcat                                              20

<210> SEQ ID NO 87
<211> LENGTH: 20
<212> TYPE: DNA
<213> ORGANISM: Homo sapiens

<400> SEQUENCE: 87
tggcaacccc agatccagct                                              20

<210> SEQ ID NO 88
<211> LENGTH: 20
<212> TYPE: DNA
<213> ORGANISM: Homo sapiens

<400> SEQUENCE: 88
caggtatttc ttctatcctg                                              20

<210> SEQ ID NO 89
<211> LENGTH: 20
<212> TYPE: DNA
<213> ORGANISM: Homo sapiens

<400> SEQUENCE: 89
gtcctccagg tcagcacctt                                              20

<210> SEQ ID NO 90
<211> LENGTH: 20
<212> TYPE: DNA
<213> ORGANISM: Homo sapiens

<400> SEQUENCE: 90
tggttacaca gtttcctgat                                              20

```
<210> SEQ ID NO 91
<211> LENGTH: 20
<212> TYPE: DNA
<213> ORGANISM: Homo sapiens

<400> SEQUENCE: 91
agaaccccct ggctgcaggt                                              20

<210> SEQ ID NO 92
<211> LENGTH: 20
<212> TYPE: DNA
<213> ORGANISM: Homo sapiens

<400> SEQUENCE: 92
gtgcgtgcat gcctgtgcat                                              20

<210> SEQ ID NO 93
<211> LENGTH: 20
<212> TYPE: DNA
<213> ORGANISM: Homo sapiens

<400> SEQUENCE: 93
cagaactgtc caggtgtcat                                              20

<210> SEQ ID NO 94
<211> LENGTH: 20
<212> TYPE: DNA
<213> ORGANISM: Homo sapiens

<400> SEQUENCE: 94
tagcaatgtc ttccctcttg                                              20

<210> SEQ ID NO 95
<211> LENGTH: 20
<212> TYPE: DNA
<213> ORGANISM: Homo sapiens

<400> SEQUENCE: 95
gcatccaggc ttccagcact                                              20

<210> SEQ ID NO 96
<211> LENGTH: 20
<212> TYPE: DNA
<213> ORGANISM: Homo sapiens

<400> SEQUENCE: 96
tccttgggtg tatgctaatg                                              20

<210> SEQ ID NO 97
<211> LENGTH: 20
<212> TYPE: DNA
<213> ORGANISM: Homo sapiens

<400> SEQUENCE: 97
gcgttgctca gaggacctag                                              20

<210> SEQ ID NO 98
<211> LENGTH: 3110
<212> TYPE: DNA
<213> ORGANISM: Homo sapiens

<400> SEQUENCE: 98
gaccaggact gtgcggctgc cggagtcctg ggaagttgtg gctgtcgaga atgggggtct    60
```

```
gtgggtacct gttcctgccc tggaagtgcc tcgtggtcgt gtctctcagg ctgctgttcc    120
ttgtacccac aggagtgccc gtgcgcagcg gagatgccac cttccccaaa gctatggaca    180
acgtgacggt ccggcagggg gagagcgcca ccctcaggtg taccatagat gaccgggtaa    240
cccgggtggc ctggctaaac cgcagcacca tcctctacgc tgggaatgac aagtggtcca    300
tagaccctcg tgtgatcatc ctggtcaata caccaaccca gtacagcatc atgatccaaa    360
atgtggatgt gtatgacgaa ggtccgtaca cctgctctgt gcagacagac aatcatccca    420
aaacgtcccg ggttcaccta atagtgcaag ttcctcctca gatcatgaat atctcctcag    480
acatcactgt gaatgaggga agcagtgtga ccctgctgtg tcttgctatt ggcagaccag    540
agccaactgt gacatggaga cacctgtcag tcaaggaagg ccagggcttt gtaagtgagg    600
atgagtacct ggagatctct gacatcaagc gagaccagtc cggggagtac gaatgcagcg    660
cgttgaacga tgtcgctgcg cccgatgtgc ggaaagtaaa aatcactgta aactatcctc    720
cctatatctc aaaagccaag aacactggtg tttcagtcgg tcagaagggc atcctgagct    780
gtgaagcctc tgcagtcccc atggctgaat tccagtggtt caaggaagaa accaggttag    840
ccactggtct ggatggaatg aggattgaaa acaaaggccg catgtccact ctgactttct    900
tcaatgtttc tgaaaaggat tatgggaact atacttgtgt ggccacgaac aagcttggga    960
acaccaatgc cagcatcaca ttgtatgggc ctggagcagt cattgatggt gtaaactcgg   1020
cctccagagc actggcttgt ctctggctat cagggaccct cttagcccac ttcttcatca   1080
agttttgata agaaatccta ggtcctctga gcaacgcctg cttctcatat cacagacttt   1140
aatctacact gcggagagca aaccagcttg ggcttctttt tgttttttc tgttattcta   1200 gatttgtttt cttttgttt tgtttattt gtttgtttgc ttttatttcc agcttgaatg   1260 agtgggttg ggggcgggt gggcagggtt ctaccacgtg taggataatc attcattggt   1320
gtgtccaaaa atgggtctg ctcctgctac cttgacccct ccctttcctc tgcttctctc   1380
ctcatcatca ttcccaacaa catcctctgc cacacacaac aaaacgtaag tttcatttgg   1440
gcaaaaattg agcctcacaa taaacaccct gaagacacaa cttgacttat aacatagtgc   1500
acagcaagag ctacatccaa gtgtcctatt atctgtgatt attttcttaa tgacaatgta   1560
catatgcccc catccatgtt aattattatc taattccatt agggttcacg tcttttcttt   1620
ctgggacact atcctactat atccatatct atagatttca atatagatga ttgtgccatc   1680
ttctgtagcc cctccgctct actcattcct tccaccatct gcagagattt gaagtttggg   1740
gctatgcatg aaacccaaca ctaaattttg caagtcaagt gaccaaaaaa ggggaggca   1800 ttttgaagat agaacctcta ttttaaaaag agaagttcaa ctcataaacg tgattgatag   1860
gtggctgatt tatttaggtt ttgtcaagct atctatcaaa gtaatggtac agttacccat   1920
ctactcaaat atctgattta tctcaccatc caattatcta cccacctgtc ttcctctcta   1980
gcaatctatt tactgtttat caatctatca atgtaattgt ctaacactcc tttctattct   2040
ctccctacta ctcactatca attcatcccc atatgaatct ctaaccatat tgtatctctc   2100
ccactgtatt catttataca ccatcagcag acattggcat cttcaaaatt atcttttcaac   2160 ttctgtgaaa gccaacgatc tcacaggtta acaaaataca aaagcaatac cctgtgttgt   2220
ggactcttta aaatctggta tcctatccac ccaagggaga cactaacaga taggccaaag   2280
tagcaagcta atgatcagtc actcactatt cccggaagag cctgtgtttt ctaaaacact   2340
ttcttgggaa gcagatcagc ctagaaaagt tttgattagc actgtggttt tccttttgca   2400
```

-continued

```
cttgaaggac aaaggtgcca gcctttatgc ttctctcaac ccttcaagaa agtacatgtc    2460
aggaacctat ggctggcttt ccttagcagc aagaacttga gagaaaaaca catctgtctc    2520
tgcaatgcaa agtgaagagt ccacccgcct gagtgggatg acttcagcta gagtctcctt    2580
tctgctccag ttctggttta atctgtttga aaactatcca gtaaaaagct gatggaggcc    2640
aattacatgg cggtgtatt gacaactctg gtatttgttt caggaagctc ttctaagctg    2700
agggcacttg agcaactgac ttaattttca agcacttgat taacaacaa ctgcaaacag    2760 aagggagaaa gtgtcagtga cacagtttcc tctgatgcag ctgcttctcc aatggctttg    2820
gggaagaact tcaccagctc ttcaggttca agcagaccc agcatacaaa caagagctga    2880
gccacctttg ctgtcttgtc tcctgggacg agaaggactc atccagcaaa gttgcctggg    2940
attcaaaata aaggcattgc agaccgcaca ggtgtgctgc agggactgat ccacagagag    3000
gatgagaatg cagcatcaat cgcagacctg ccctgcctca gttggaaaac cttttcaggc    3060
cctcagtcta aaaataaaa aatatgagca ccaaaaaaaa aaaaaaaaa                 3110
```

<210> SEQ ID NO 99
<211> LENGTH: 345
<212> TYPE: PRT
<213> ORGANISM: Homo sapiens

<400> SEQUENCE: 99

```
Met Gly Val Cys Gly Tyr Leu Phe Leu Pro Trp Lys Cys Leu Val Val
 1               5                  10                  15

Val Ser Leu Arg Leu Leu Phe Leu Val Pro Thr Gly Val Pro Val Arg
             20                  25                  30

Ser Gly Asp Ala Thr Phe Pro Lys Ala Met Asp Asn Val Thr Val Arg
         35                  40                  45

Gln Gly Glu Ser Ala Thr Leu Arg Cys Thr Ile Asp Asp Arg Val Thr
     50                  55                  60

Arg Val Ala Trp Leu Asn Arg Ser Thr Ile Leu Tyr Ala Gly Asn Asp
 65                  70                  75                  80

Lys Trp Ser Ile Asp Pro Arg Val Ile Leu Val Asn Thr Pro Thr
                 85                  90                  95

Gln Tyr Ser Ile Met Ile Gln Asn Val Asp Val Tyr Asp Glu Gly Pro
            100                 105                 110

Tyr Thr Cys Ser Val Gln Thr Asp Asn His Pro Lys Thr Ser Arg Val
        115                 120                 125

His Leu Ile Val Gln Val Pro Pro Gln Ile Met Asn Ile Ser Ser Asp
    130                 135                 140

Ile Thr Val Asn Glu Gly Ser Ser Val Thr Leu Leu Cys Leu Ala Ile
145                 150                 155                 160

Gly Arg Pro Glu Pro Thr Val Thr Trp Arg His Leu Ser Val Lys Glu
                165                 170                 175

Gly Gln Gly Phe Val Ser Glu Asp Glu Tyr Leu Glu Ile Ser Asp Ile
            180                 185                 190

Lys Arg Asp Gln Ser Gly Glu Tyr Glu Cys Ser Ala Leu Asn Asp Val
        195                 200                 205

Ala Ala Pro Asp Val Arg Lys Val Lys Ile Thr Val Asn Tyr Pro Pro
    210                 215                 220

Tyr Ile Ser Lys Ala Lys Asn Thr Gly Val Ser Val Gly Gln Lys Gly
225                 230                 235                 240

Ile Leu Ser Cys Glu Ala Ser Ala Val Pro Met Ala Glu Phe Gln Trp
                245                 250                 255
```

```
Phe Lys Glu Glu Thr Arg Leu Ala Thr Gly Leu Asp Gly Met Arg Ile
            260                 265                 270
Glu Asn Lys Gly Arg Met Ser Thr Leu Thr Phe Phe Asn Val Ser Glu
        275                 280                 285
Lys Asp Tyr Gly Asn Tyr Thr Cys Val Ala Thr Asn Lys Leu Gly Asn
    290                 295                 300
Thr Asn Ala Ser Ile Thr Leu Tyr Gly Pro Gly Ala Val Ile Asp Gly
305                 310                 315                 320
Val Asn Ser Ala Ser Arg Ala Leu Ala Cys Leu Trp Leu Ser Gly Thr
                325                 330                 335
Leu Leu Ala His Phe Phe Ile Lys Phe
                340                 345

<210> SEQ ID NO 100
<211> LENGTH: 1839
<212> TYPE: DNA
<213> ORGANISM: Homo sapiens

<400> SEQUENCE: 100
gcggaagcag cgaggaggga gcccccttg gccgtcctcc gtggaaccgg ttttccgagg      60
ctggcaaaag ccgaggctgg atttggggga ggaatattag actcggagga gtctgcgcgc    120
ttttctcctc cccgcgcctc ccggtcgccg cgggttcacc gctcagtccc cgcgctcgct    180
ccgcacccca cccacttcct gtgctcgccc ggggggcgtg tgccgtgcgg ctgccggagt    240
tcggggaagt tgtggctgtc gagaatgggg gtctgtgggt acctgttcct gccctggaag    300
tgcctcgtgg tcgtgtctct caggctgctg ttccttgtac ccacaggagt gcccgtgcgc    360
agcggagatg ccaccttccc caaagctatg acaacgtga cggtccggca ggggagagc    420 gccacgctca ggtgcactat tgacaaccgg gtcacccggg tggcctggct aaaccgcagc    480
accatcctct atgctgggaa tgacaagtgg tgcctggatc ctcgcgtggt ccttctgagc    540
aacacccaaa cgcagtacag catcgagatc agaacgtgg atgtgtatga cgagggccct    600
tacacctgct cggtgcagac agacaaccac ccaaagacct ctagggtcca cctcattgtg    660
caagtatctc ccaaaattgt agagatttct tcagatatct ccattaatga agggaacaat    720
attagcctca cctgcatagc aactggtaga ccagagccta cggttacttg agacacatc    780 tctcccaaag cggttggctt tgtgagtgaa gacgaatact ggaaattca gggcatcacc    840 cgggaacagt caggggacta cgagtgcagt gcctccaatg acgtggccgc gcccgtggta    900
cggagagtaa aggtcaccgt gaactatcca ccatacattt cagaagccaa gggtacaggt    960
gtccccgtgg gacaaaaggg gacactgcag tgtgaagcct cagcagtccc ctcagcagaa   1020
ttccagtggt acaaggatga caaaagactg attgaaggaa agaaaggggt gaagtggaa    1080 aacagacctt tcctctcaaa actcatcttc ttcaatgtct ctgaacatga ctatgggaac    1140
tacacttgcg tggcctccaa caagctgggc cacaccaatg ccagcatcat gctatttggt    1200
ccaggcgccg tcagcgaggt gagcaacggc acgtcgagga gggcaggctg cgtctggctg    1260
ctgcctcttc tggtcttgca cctgcttctc aaattttgat gtgagtgcca cttccccacc    1320
cgggaaaggc tgccgccacc accaccacca acacaacagc aatggcaaca ccgcacagcaa   1380 ccaatcagat atatacaaat gaaattagaa gaaacacagc ctcatgggac agaaatttga    1440
gggaggggaa caagaatac tttgggggga aagagttttt aaaaagaaa ttgaaaattg     1500 ccttgcagat atttaggtac aatggagttt tcttttccca acgggaaga acacagcaca    1560
```

```
cccggcttgg acccactgca agctgcatcg tgcaacctct ttggtgccag tgtgggcaag    1620
ggctcagcct ctctgcccac agactgcccc cacgtggaac attctggagc tggccatccc    1680
aaattcaatc agtccataga gacgaacaga atgagacctt ccggcccaag cgtggcgctt    1740
ccggcccaag cgtggcgctg cgggcacttt ggtagactgt gccaccacgg cgtgtgttgt    1800
gaaacgtgaa ataaaagag caaaaaaaaa aaaaaaaa                             1839

<210> SEQ ID NO 101
<211> LENGTH: 344
<212> TYPE: PRT
<213> ORGANISM: Homo sapiens

<400> SEQUENCE: 101

Met Gly Val Cys Gly Tyr Leu Phe Leu Pro Trp Lys Cys Leu Val Val
1               5                   10                  15

Val Ser Leu Arg Leu Leu Phe Leu Val Pro Thr Gly Val Pro Val Arg
            20                  25                  30

Ser Gly Asp Ala Thr Phe Pro Lys Ala Met Asp Asn Val Thr Val Arg
        35                  40                  45

Gln Gly Glu Ser Ala Thr Leu Arg Cys Thr Ile Asp Asn Arg Val Thr
    50                  55                  60

Arg Val Ala Trp Leu Asn Arg Ser Thr Ile Leu Tyr Ala Gly Asn Asp
65                  70                  75                  80

Lys Trp Cys Leu Asp Pro Arg Val Val Leu Leu Ser Asn Thr Gln Thr
                85                  90                  95

Gln Tyr Ser Ile Glu Ile Gln Asn Val Asp Val Tyr Asp Glu Gly Pro
            100                 105                 110

Tyr Thr Cys Ser Val Gln Thr Asp Asn His Pro Lys Thr Ser Arg Val
        115                 120                 125

His Leu Ile Val Gln Val Ser Pro Lys Ile Val Glu Ile Ser Ser Asp
    130                 135                 140

Ile Ser Ile Asn Glu Gly Asn Asn Ile Ser Leu Thr Cys Ile Ala Thr
145                 150                 155                 160

Gly Arg Pro Glu Pro Thr Val Thr Trp Arg His Ile Ser Pro Lys Ala
                165                 170                 175

Val Gly Phe Val Ser Glu Asp Glu Tyr Leu Glu Ile Gln Gly Ile Thr
            180                 185                 190

Arg Glu Gln Ser Gly Asp Tyr Glu Cys Ser Ala Ser Asn Asp Val Ala
        195                 200                 205

Ala Pro Val Val Arg Arg Val Lys Val Thr Val Asn Tyr Pro Pro Tyr
    210                 215                 220

Ile Ser Glu Ala Lys Gly Thr Gly Val Pro Val Gly Gln Lys Gly Thr
225                 230                 235                 240

Leu Gln Cys Glu Ala Ser Ala Val Pro Ser Ala Glu Phe Gln Trp Tyr
                245                 250                 255

Lys Asp Asp Lys Arg Leu Ile Glu Gly Lys Lys Gly Val Lys Val Glu
            260                 265                 270

Asn Arg Pro Phe Leu Ser Lys Leu Ile Phe Phe Asn Val Ser Glu His
        275                 280                 285

Asp Tyr Gly Asn Tyr Thr Cys Val Ala Ser Asn Lys Leu Gly His Thr
    290                 295                 300

Asn Ala Ser Ile Met Leu Phe Gly Pro Gly Ala Val Ser Glu Val Ser
305                 310                 315                 320

Asn Gly Thr Ser Arg Arg Ala Gly Cys Val Trp Leu Leu Pro Leu Leu
```

```
                    325                 330                 335
Val Leu His Leu Leu Leu Lys Phe
            340

<210> SEQ ID NO 102
<211> LENGTH: 1068
<212> TYPE: DNA
<213> ORGANISM: Homo sapiens

<400> SEQUENCE: 102 atggggggtct gtgggtacct gttcctgccc tggaagtgcc tcgtggtcgt gtctctcagg     60
ctgctgttcc ttgtacccac aggagtgccc gtgcgcagcg gagatgccac cttccccaaa    120
gctatggaca cgtgacggt ccggcagggg gagagcgcca ccctcaggtg cactattgac     180
aaccgggtca cccgggtggc ctggctaaac cgcagcacca tcctctatgc tgggaatgac    240
aagtggtgcc tggatcctcg cgtggtcctt ctgagcaaca cccaaacgca gtacagcatc    300
gagatccaga acgtggatgt gtatgacgag ggcccttaca cctgctcggt gcagacagac    360
aaccacccaa agacctctag ggtccacctc attgtgcaag tatctcccaa aattgtagag    420
atttcttcag atatctccat taatgaaggg aacaatatta gcctcacctg catagcaact    480
ggtagaccag agcctacggt tacttggaga cacatctctc ccaaagcggt tggctttgtg    540
agtgaagacg aatacttgga aattcagggc atcacccggg aacagtcagg ggactacgag    600
tgcagtgcct ccaatgacgt ggccgcgccc gtggtacgga gagtaaaggt caccgtgaac    660
tatccaccat acatttcaga agccaagggt acaggtgtcc ccgtgggaca aaaggggaca    720
ctgcagtgtg aagcctcagc agtccctca gcagaattcc agtggtacaa ggatgacaaa    780
agactgattg aaggaaagaa agggggtgaaa gtggaaaaca gacctttcct ctcaaaactc    840
atcttcttca atgtctctga acatgactat gggaactaca cttgcgtggc ctccaacaag    900
ctgggccaca ccaatgccag catcatgcta tttgaagtaa aaactacagc cctgaccect    960 tggaaaggtc aggcgccgt cagcgaggtg agcaacggca cgtcgaggag ggcaggctgc   1020
gtctggctgc tgcctcttct ggtcttgcac ctgcttctca aattttga                1068

<210> SEQ ID NO 103
<211> LENGTH: 355
<212> TYPE: PRT
<213> ORGANISM: Homo sapiens

<400> SEQUENCE: 103

Met Gly Val Cys Gly Tyr Leu Phe Leu Pro Trp Lys Cys Leu Val Val
1               5                   10                  15

Val Ser Leu Arg Leu Leu Phe Leu Val Pro Thr Gly Val Pro Val Arg
            20                  25                  30

Ser Gly Asp Ala Thr Phe Pro Lys Ala Met Asp Asn Val Thr Val Arg
        35                  40                  45

Gln Gly Glu Ser Ala Thr Leu Arg Cys Thr Ile Asp Asn Arg Val Thr
    50                  55                  60

Arg Val Ala Trp Leu Asn Arg Ser Thr Ile Leu Tyr Ala Gly Asn Asp
65                  70                  75                  80

Lys Trp Cys Leu Asp Pro Arg Val Val Leu Leu Ser Asn Thr Gln Thr
                85                  90                  95

Gln Tyr Ser Ile Glu Ile Gln Asn Val Asp Val Tyr Asp Glu Gly Pro
            100                 105                 110

Tyr Thr Cys Ser Val Gln Thr Asp Asn His Pro Lys Thr Ser Arg Val
```

-continued

```
                  115                 120                 125
His Leu Ile Val Gln Val Ser Pro Lys Ile Val Glu Ile Ser Ser Asp
    130                 135                 140

Ile Ser Ile Asn Glu Gly Asn Asn Ile Ser Leu Thr Cys Ile Ala Thr
145                 150                 155                 160

Gly Arg Pro Glu Pro Thr Val Thr Trp Arg His Ile Ser Pro Lys Ala
                165                 170                 175

Val Gly Phe Val Ser Glu Asp Glu Tyr Leu Glu Ile Gln Gly Ile Thr
            180                 185                 190

Arg Glu Gln Ser Gly Asp Tyr Glu Cys Ser Ala Ser Asn Asp Val Ala
        195                 200                 205

Ala Pro Val Val Arg Arg Val Lys Val Thr Val Asn Tyr Pro Pro Tyr
    210                 215                 220

Ile Ser Glu Ala Lys Gly Thr Gly Val Pro Val Gly Gln Lys Gly Thr
225                 230                 235                 240

Leu Gln Cys Glu Ala Ser Ala Val Pro Ser Ala Glu Phe Gln Trp Tyr
                245                 250                 255

Lys Asp Asp Lys Arg Leu Ile Glu Gly Lys Lys Gly Val Lys Val Glu
            260                 265                 270

Asn Arg Pro Phe Leu Ser Lys Leu Ile Phe Phe Asn Val Ser Glu His
        275                 280                 285

Asp Tyr Gly Asn Tyr Thr Cys Val Ala Ser Asn Lys Leu Gly His Thr
    290                 295                 300

Asn Ala Ser Ile Met Leu Phe Glu Val Lys Thr Thr Ala Leu Thr Pro
305                 310                 315                 320

Trp Lys Gly Pro Gly Ala Val Ser Glu Val Ser Asn Gly Thr Ser Arg
                325                 330                 335

Arg Ala Gly Cys Val Trp Leu Leu Pro Leu Leu Val Leu His Leu Leu
            340                 345                 350

Leu Lys Phe
        355

<210> SEQ ID NO 104
<211> LENGTH: 1104
<212> TYPE: DNA
<213> ORGANISM: Homo sapiens

<400> SEQUENCE: 104
atgggggtct gtgggtacct gttcctgccc tggaagtgcc tcgtggtcgt gtctctcagg      60
ctgctgttcc ttgtacccac aggagtgccc gtgcgcagcg gagatgccac cttccccaaa     120
gctatggaca cgtgacggt ccggcagggg gagagcgcca ccctcaggtg cactattgac      180
aaccgggtca cccgggtggc ctggctaaac cgcagcacca tcctctatgc tgggaatgac     240
aagtggtgcc tggatcctcg cgtggtcctt ctgagcaaca cccaaacgca gtacagcatc     300
gagatccaga acgtggatgt gtatgacgag ggcccttaca cctgctcggt gcagacagac     360
aaccacccaa agacctctag ggtccacctc attgtgcaag tatctcccaa aattgtagag     420
atttcttcag atatctccat taatgaaggg aacaatatta gcctcacctg catagcaact     480
ggtagaccag agcctacggt tacttggaga cacatctctc ccaaagcggt tggctttgtg     540
agtgaagacg aatacttgga aattcagggc atcacccggg aacagtcagg ggactacgag     600
tgcagtgcct ccaatgacgt ggccgcgccc gtgtacggag gagtaaaggt caccgtgaac     660
tatccaccat acatttcaga agccaagggt acaggtgtcc ccgtgggaca aaaggggaca     720
```

```
ctgcagtgtg aagcctcagc agtcccctca gcagaattcc agtggtacaa ggatgacaaa    780
agactgattg aaggaaagaa agggqtgaaa gtggaaaaca gacctttcct ctcaaaactc    840
atcttcttca atgtctctga acatgactat gggaactaca cttgcgtggc ctccaacaag    900
ctgggccaca ccaatgccag catcatgcta tttgaactaa atgagcctac gagctcaact    960
ttgttgcaag aagtgaaaac tacagccctg accccttgga aagtccaggc gccgtcagc   1020 gaggtgagca acggcacgtc gaggagggca ggctgcgtct ggctgctgcc tcttctggtc   1080
ttgcacctgc ttctcaaatt ttga                                          1104
```

<210> SEQ ID NO 105
<211> LENGTH: 367
<212> TYPE: PRT
<213> ORGANISM: Homo sapiens

<400> SEQUENCE: 105

```
Met Gly Val Cys Gly Tyr Leu Phe Leu Pro Trp Lys Cys Leu Val Val
 1               5                   10                  15

Val Ser Leu Arg Leu Leu Phe Leu Val Pro Thr Gly Val Pro Val Arg
                20                  25                  30

Ser Gly Asp Ala Thr Phe Pro Lys Ala Met Asp Asn Val Thr Val Arg
            35                  40                  45

Gln Gly Glu Ser Ala Thr Leu Arg Cys Thr Ile Asp Asn Arg Val Thr
        50                  55                  60

Arg Val Ala Trp Leu Asn Arg Ser Thr Ile Leu Tyr Ala Gly Asn Asp
 65                  70                  75                   80

Lys Trp Cys Leu Asp Pro Arg Val Val Leu Leu Ser Asn Thr Gln Thr
                85                  90                  95

Gln Tyr Ser Ile Glu Ile Gln Asn Val Asp Val Tyr Asp Glu Gly Pro
           100                 105                 110

Tyr Thr Cys Ser Val Gln Thr Asp Asn His Pro Lys Thr Ser Arg Val
        115                 120                 125

His Leu Ile Val Gln Val Ser Pro Lys Ile Val Glu Ile Ser Ser Asp
    130                 135                 140

Ile Ser Ile Asn Glu Gly Asn Asn Ile Ser Leu Thr Cys Ile Ala Thr
145                 150                 155                 160

Gly Arg Pro Glu Pro Thr Val Thr Trp Arg His Ile Ser Pro Lys Ala
                165                 170                 175

Val Gly Phe Val Ser Glu Asp Glu Tyr Leu Glu Ile Gln Gly Ile Thr
            180                 185                 190

Arg Glu Gln Ser Gly Asp Tyr Glu Cys Ser Ala Ser Asn Asp Val Ala
        195                 200                 205

Ala Pro Val Val Arg Arg Val Lys Val Thr Val Asn Tyr Pro Pro Tyr
    210                 215                 220

Ile Ser Glu Ala Lys Gly Thr Gly Val Pro Val Gly Gln Lys Gly Thr
225                 230                 235                 240

Leu Gln Cys Glu Ala Ser Ala Val Pro Ser Ala Glu Phe Gln Trp Tyr
                245                 250                 255

Lys Asp Asp Lys Arg Leu Ile Glu Gly Lys Lys Gly Val Lys Val Glu
            260                 265                 270

Asn Arg Pro Phe Leu Ser Lys Leu Ile Phe Phe Asn Val Ser Glu His
        275                 280                 285

Asp Tyr Gly Asn Tyr Thr Cys Val Ala Ser Asn Lys Leu Gly His Thr
    290                 295                 300
```

```
Asn Ala Ser Ile Met Leu Phe Glu Leu Asn Glu Pro Thr Ser Ser Thr
305                 310                 315                 320

Leu Leu Gln Glu Val Lys Thr Thr Ala Leu Thr Pro Trp Lys Gly Pro
                325                 330                 335

Gly Ala Val Ser Glu Val Ser Asn Gly Thr Ser Arg Arg Ala Gly Cys
            340                 345                 350

Val Trp Leu Leu Pro Leu Leu Val Leu His Leu Leu Lys Phe
        355                 360                 365

<210> SEQ ID NO 106
<211> LENGTH: 1140
<212> TYPE: DNA
<213> ORGANISM: Homo sapiens

<400> SEQUENCE: 106
atgggggtct gtgggtacct gttcctgccc tggaagtgcc tcgtggtcgt gtctctcagg      60
ctgctgttcc ttgtacccac aggagtgccc gtgcgcagcg gagatgccac cttcccaaa     120 gctatggaca acgtgacggt ccggcagggg gagagcgcca ccctcaggtg cactattgac    180
aaccgggtca cccgggtggc ctggctaaac cgcagcacca tcctctatgc tgggaatgac    240
aagtggtgcc tggatcctcg cgtggtcctt ctgagcaaca cccaaacgca gtacagcatc    300
gagatccaga acgtggatgt gtatgacgag ggccccttaca cctgctcggt gcagacagac    360
aaccacccaa agacctctag ggtccacctc attgtgcaag tatctcccaa aattgtagag    420
atttcttcag atatctccat taatgaaggg aacaatatta gcctcacctg catagcaact    480
ggtagaccag agcctacggt tacttggaga cacatctctc ccaaagcggt tggctttgtg    540
agtgaagacg aatacttgga aattcagggc atcacccggg aacagtcagg ggactacgag    600
tgcagtgcct ccaatgacgt ggccgcgccc gtggtacgga gagtaaaggt caccgtgaac    660
tatccaccat acatttcaga agccaagggt acaggtgtcc ccgtgggaca aaaggggaca    720
ctgcagtgtg aagcctcagc agtcccctca gcagaattcc agtggtacaa ggatgacaaa    780
agactgattg aaggaaagaa agggggtgaaa gtggaaaaca gacctttcct ctcaaaactc    840
atcttcttca atgtctctga acatgactat gggaactaca cttgcgtggc ctccaacaag    900
ctgggccaca ccaatgccag catcatgcta ttttgatggc tcctaagctg actgtgggaa    960
tcataattgg aactaaatga gcctacgagc tcaactttgt tgcaagaagt gaaaactaca   1020
gccctgaccc cttggaaagg tccaggcgcc gtcagcgagg tgagcaacgg cacgtcgagg   1080
agggcaggct gcgtctggct gctgcctctt ctggtcttgc acctgcttct caaatttga   1140

<210> SEQ ID NO 107
<211> LENGTH: 311
<212> TYPE: PRT
<213> ORGANISM: Homo sapiens

<400> SEQUENCE: 107

Met Gly Val Cys Gly Tyr Leu Phe Leu Pro Trp Lys Cys Leu Val Val
1               5                   10                  15

Val Ser Leu Arg Leu Leu Phe Leu Val Pro Thr Gly Val Pro Val Arg
                20                  25                  30

Ser Gly Asp Ala Thr Phe Pro Lys Ala Met Asp Asn Val Thr Val Arg
            35                  40                  45

Gln Gly Glu Ser Ala Thr Leu Arg Cys Thr Ile Asp Asn Arg Val Thr
        50                  55                  60

Arg Val Ala Trp Leu Asn Arg Ser Thr Ile Leu Tyr Ala Gly Asn Asp
```

```
                65                  70                  75                  80
Lys Trp Cys Leu Asp Pro Arg Val Val Leu Ser Asn Thr Gln Thr
                    85                  90                  95
Gln Tyr Ser Ile Glu Ile Gln Asn Val Asp Val Tyr Asp Glu Gly Pro
                100                 105                 110
Tyr Thr Cys Ser Val Gln Thr Asp Asn His Pro Lys Thr Ser Arg Val
                115                 120                 125
His Leu Ile Val Gln Val Ser Pro Lys Ile Val Glu Ile Ser Ser Asp
            130                 135                 140
Ile Ser Ile Asn Glu Gly Asn Asn Ile Ser Leu Thr Cys Ile Ala Thr
145                 150                 155                 160
Gly Arg Pro Glu Pro Thr Val Thr Trp Arg His Ile Ser Pro Lys Ala
                165                 170                 175
Val Gly Phe Val Ser Glu Asp Glu Tyr Leu Glu Ile Gln Gly Ile Thr
            180                 185                 190
Arg Glu Gln Ser Gly Asp Tyr Glu Cys Ser Ala Ser Asn Asp Val Ala
                195                 200                 205
Ala Pro Val Val Arg Arg Val Lys Val Thr Val Asn Tyr Pro Pro Tyr
        210                 215                 220
Ile Ser Glu Ala Lys Gly Thr Gly Val Pro Val Gly Gln Lys Gly Thr
225                 230                 235                 240
Leu Gln Cys Glu Ala Ser Ala Val Pro Ser Ala Glu Phe Gln Trp Tyr
                245                 250                 255
Lys Asp Asp Lys Arg Leu Ile Glu Gly Lys Lys Gly Val Lys Val Glu
                260                 265                 270
Asn Arg Pro Phe Leu Ser Lys Leu Ile Phe Phe Asn Val Ser Glu His
            275                 280                 285
Asp Tyr Gly Asn Tyr Thr Cys Val Ala Ser Asn Lys Leu Gly His Thr
        290                 295                 300
Asn Ala Ser Ile Met Leu Phe
305                 310

<210> SEQ ID NO 108
<211> LENGTH: 4
<212> TYPE: PRT
<213> ORGANISM: Homo sapiens

<400> SEQUENCE: 108

Trp Leu Leu Ser
1

<210> SEQ ID NO 109
<211> LENGTH: 4
<212> TYPE: PRT
<213> ORGANISM: Homo sapiens

<400> SEQUENCE: 109

Leu Trp Glu Ser
1

<210> SEQ ID NO 110
<211> LENGTH: 57
<212> TYPE: PRT
<213> ORGANISM: Homo sapiens

<400> SEQUENCE: 110

Leu Glu Leu Asn Glu Pro Thr Ser Ser Thr Leu Leu Gln Glu Val Lys
1               5                   10                  15
```

```
Thr Thr Ala Leu Thr Pro Trp Lys Gly Pro Gly Ala Val Ser Glu Val
         20                  25                  30

Ser Asn Gly Thr Ser Arg Arg Ala Gly Cys Val Trp Leu Leu Pro Leu
         35                  40                  45

Leu Val Leu His Leu Leu Lys Phe
         50              55
```

```
<210> SEQ ID NO 111
<211> LENGTH: 270
<212> TYPE: DNA
<213> ORGANISM: Homo sapiens
<220> FEATURE:
<221> NAME/KEY: misc_feature
<222> LOCATION: (250)..(270)
<223> OTHER INFORMATION: unknown

<400> SEQUENCE: 111
cgcttcccga gcccgctggt gcgcggggcg ggggaccagg actgtgcggc tgccggagtc      60
ctgggaagtt gtggctgtcg agaatggggg tctgtgggta cctgttcctg ccctggaagt     120
gcctcgtggt cgtgtctctc aggctgctgt tccttgtacc cacaggagct gcccgtgcgc     180
aggaagatgc caccttcccc aaagctatgg acaacgtgac ggtccggcac cggcagagcg     240
ccactctcan nnnnnnnnnn nnnnnnnnnn                                      270

<210> SEQ ID NO 112
<211> LENGTH: 540
<212> TYPE: DNA
<213> ORGANISM: Homo sapiens

<400> SEQUENCE: 112
ttttagcact gtgttttgtt gtttcattta ctcctcaaaa tgcaacgtct tatttaccat      60
attatataat ctctccactc tctctctttc ccttcttcct ccctccacca ctccctgcct     120
cactgcaggt gtaccataga tgaccgggta acccgggtgg cctggctaaa ccgcagcacc     180
atcctctacg ctgggaatga caagtggtcc atagaccctc gtgtgatcat cctggtcaat     240
acaccaaccc agtacagcat catgatccaa aatgtggatg tgtatgacga aggtccgtac     300
acctgctctg tgcagacaga caatcatccc aaaacgtccc gggttcacct aatagtgcaa     360
ggtaagtccc agctggatct ggggttgcca ttcccgtcag tgatggaggg gaagaacagt     420
gttggtgttt gttctacctg tgtgcgaaga cacaaaagtc atcttcctct actgaatcca     480
gagtttgact atatgtcttg gaatgtttcc catcgaatgg gtacttaact aagtgctgaa     540

<210> SEQ ID NO 113
<211> LENGTH: 420
<212> TYPE: DNA
<213> ORGANISM: Homo sapiens

<400> SEQUENCE: 113
atttattata aaaacatgct atacaaaaat ttgtaggcta cacctcctt ttaagtgcaa       60 agaattattc tcaggtattt cttctatcct gtttccttac agttcctcct cagatcatga     120
atatctcctc agacatcact gtgaatgagg gaagcagtgt gaccctgctg tgtcttgcta     180
ttggcagacc agagccaact gtgacatgga gacacctgtc agtcaagggt aaggtgctga     240
cctggaggac gttttcagag gtagtatgtt aaagtcttgg ctcttatgca caacagagct     300
tcaggaatca gaaaacattt tgtaatccag tcatagaaaa tcaaacaggc aatatgcacc     360
aattgctggc tatttcattt caaaagaagg attcatagag gaaatttgct aaatgatggt     420
```

<210> SEQ ID NO 114
<211> LENGTH: 420
<212> TYPE: DNA
<213> ORGANISM: Homo sapiens

<400> SEQUENCE: 114

```
tctgatggct ttttctcttc ctcctcctac aatctctaga tgtgaatatg gttctgtccc    60
tggttacaca gtttcctgat tgtttcctgt ctgcttcttt cttcccagaa ggccagggct   120
ttgtaagtga ggatgagtac ctggagatct ctgacatcaa gcgagaccag tccggggagt   180
acgaatgcag cgcgttgaac gatgtcgctg cgcccgatgt gcggaaagta aaaatcactg   240
taaactgtga gtggacctgc agccagggg ttctggggaa aagacggcac agggagtagg   300
tggacaatct ggtaatggca gtgccatttt ccaaaggacc caggttcctg ccaacaggaa   360
aatacttcat cagatggctt tgcccaccat ggcctccgtg ccatttgtcc ctggaatctt   420
```

<210> SEQ ID NO 115
<211> LENGTH: 480
<212> TYPE: DNA
<213> ORGANISM: Homo sapiens

<400> SEQUENCE: 115

```
aaatgattat tttactggga agagggttg tcacaagaaa tccatttaca tagcaaatgg    60
ctggatgtgc ccttcatctc tttcacgaaa tcactctgtg tgtgcgtgcg tgcatgcctg   120
tgcatgtgtg tgtgtgtgtt tcccacagat cctcccctata tctcaaaagc caagaacact   180
ggtgtttcag tcggtcagaa gggcatcctg agctgtgaag cctctgcagt ccccatggct   240
gaattccagt ggttcaagga agaaaccagg tacctttaa atgacacctg gacagttctg   300
aagcagagct gatggtctat ccccacatgg gagaaggatg aggatgaaga aaagggaaa   360
gataaggcaa aacagaaata tactatgccc tcttttgtaa caaagtctat ttttacaacg   420
agaaaaaaaa tggaggaggc tgggaagtgg agaaaatgaa ctgaccatga ttctgaatct   480
```

<210> SEQ ID NO 116
<211> LENGTH: 479
<212> TYPE: DNA
<213> ORGANISM: Homo sapiens

<400> SEQUENCE: 116

```
ggcaagagca tcatttccct tctcctcctg ttggacactg aagtgcttag ggtttgagtt    60
tgaaggacga gattagttgg agaaaagagt ttggtgagga ggagggcctc tttgtagaat   120
aattgatagc aatgtcttcc ctcttgcagg ttagccactg gtctggatgg aatgaggatt   180
gaaaacaaag gccgcatgtc cactctgact ttcttcaatg tttcagaaaa ggattatggg   240
aactatactt gtgtggccac gaacaagctt gggaacacca atgccagcat cacattgtat   300
ggtgagtgct ggaagcctgg atgcagtggg ctcagccaca tggggaagct tgagggactc   360
aggagggagg aagttgcaat ctgcttggcc tgtgtccatc catcctactc aacccaccac   420
ctgtagataa gacatacttc tccctgccat tcccctagca tgccatgcag agatagtta   479
```

<210> SEQ ID NO 117
<211> LENGTH: 420
<212> TYPE: DNA
<213> ORGANISM: Homo sapiens

<400> SEQUENCE: 117

```
ttgtttagac ttggaatggt cagcggaagg gtggaaggtg ggaagcatgt atgtgtattt      60
gcttgtcagg gaagaactat ggtgtccttg ggtgtatgct aatgggtctg tctctctctc     120
ccctacacag ggcctggagc agtcattgat ggtgtaaact cggcctccag agcactggct     180
tgtctctggc tatcagggac cctcttagcc cacttcttca tcaagttttg ataagaaatc     240
ctaggtcctc tgagcaacgc ctgcttctcc atatcacaga ctttaatcta cactgcggag     300
agcaaaccag cttgggcttc ttttttgttt tttctgttat tctagatttg ttttcttttt     360
gtttttgttt atttgtttgt ttgcttttat ttccagcttg aatgagtggg gttgggggcg     420
```

<210> SEQ ID NO 118
<211> LENGTH: 51
<212> TYPE: DNA
<213> ORGANISM: Homo sapiens

<400> SEQUENCE: 118

```
gtgtgatcat cctggtcaat acaccaaccc agtacagcat catgatccaa a              51
```

<210> SEQ ID NO 119
<211> LENGTH: 16
<212> TYPE: PRT
<213> ORGANISM: Homo sapiens

<400> SEQUENCE: 119

```
Val Ile Ile Leu Val Asn Thr Pro Thr Gln Tyr Ser Ile Met Ile Gln
1               5                   10                  15
```

<210> SEQ ID NO 120
<211> LENGTH: 51
<212> TYPE: DNA
<213> ORGANISM: Homo sapiens

<400> SEQUENCE: 120

```
gtgtgatcat cctggtcaat acacgaaccc agtacagcat catgatccaa a              51
```

<210> SEQ ID NO 121
<211> LENGTH: 16
<212> TYPE: PRT
<213> ORGANISM: Homosapiens

<400> SEQUENCE: 121

```
Val Ile Ile Leu Val Asn Thr Arg Thr Gln Tyr Ser Ile Met Ile Gln
1               5                   10                  15
```

<210> SEQ ID NO 122
<211> LENGTH: 899
<212> TYPE: DNA
<213> ORGANISM: Homosapiens

<400> SEQUENCE: 122

```
attgagattt gccactttgg ggacaggcgt ccagtggagg ggcacgggcg tttccgaggt      60
gggtcctcgg aggtgggtgc actccacctc tgcgcgggcc caggacagcg cgccgtcagg     120
gctggacttg gctgggcggg gagccgattg cagcgcgatg gacacgcaca ccggtgcccc     180
atctggcgtg ggcagggtag ttcagctctc cagggcgggg tttgtcaact tctgcgctgg     240
catcggcgag ggaaggtgcc agtgtcagtt ttcagttttgc tgctttcccc agaactccct    300
ctcccgccct cccctctccc tcccgctcc cccaccccg cccctctgt agggaagcc         360 gctgcgaggg gcgccgcgtt ctctccgctg gcgcgggtgt cggacgcgag cgaagtgggc     420
gcggtgcggg ctcatccccg caggcatccc cagcccggtg ggcgcggcgg aggttaaggt     480
```

```
gggcgcccgc cgtcgggatg agcgcgcagt ccgcgccgcc cgccagcccg ctcgctccga      540
ggcggcaccg ggagaaagtg gcggtcaggg atggagctgc tgccatgaca accccggcgg      600
tccgggcccg cgcgcgtcgg ggctgctccc gggaggaagg cggcgcggag ccggggggcgg    660 ccgctgagcg tggcgtccgc gcgtccccgc gtctcgtgcc gcgtccccgg aggaagcggg      720
ggccgccgtc cgcccagctc cccgtgcgcc cggagttccc cgcgggcggc gctcccccgg      780
ctggccgcga gtcgccgacc gggctgcaga ggacggccac cgaccggacg accctgctgc      840
gccggtgcgg tccccgcctt ggaactttt gccgccttgg ggttccagat gcgagacct        899

<210> SEQ ID NO 123
<211> LENGTH: 46
<212> TYPE: DNA
<213> ORGANISM: Homo sapiens

<400> SEQUENCE: 123
gatcatcctg gtcaatacac caacccagta cagcatcatg atccaa                      46

<210> SEQ ID NO 124
<211> LENGTH: 46
<212> TYPE: DNA
<213> ORGANISM: Homo sapiens

<400> SEQUENCE: 124
tgatcatcct ggtcaataca ccaacccagt acagcatcat gatcca                      46
```